(12) United States Patent
Nakatsuji et al.

(10) Patent No.: US 10,233,426 B2
(45) Date of Patent: Mar. 19, 2019

(54) METHOD FOR INDUCING CARDIAC DIFFERENTIATION OF PLURIPOTENT STEM CELL WITH LOW-MOLECULAR COMPOUNDS

(71) Applicant: KYOTO UNIVERSITY, Kyoto-shi (JP)

(72) Inventors: Norio Nakatsuji, Kyoto (JP); Itsunari Minami, Kyoto (JP)

(73) Assignee: KYOTO UNIVERSITY, Kyoto-Shi, Kyoto (JP)

( * ) Notice: Subject to any disclaimer, the term of this patent is extended or adjusted under 35 U.S.C. 154(b) by 0 days.

(21) Appl. No.: 15/314,409

(22) PCT Filed: May 29, 2015

(86) PCT No.: PCT/JP2015/065643
§ 371 (c)(1),
(2) Date: Nov. 28, 2016

(87) PCT Pub. No.: WO2015/182765
PCT Pub. Date: Dec. 3, 2015

(65) Prior Publication Data
US 2017/0152485 A1 Jun. 1, 2017

(30) Foreign Application Priority Data

May 30, 2014 (JP) ................. 2014-113325

(51) Int. Cl.
| A61K 35/12 | (2015.01) |
| C12N 5/077 | (2010.01) |
| C12N 5/10 | (2006.01) |
| C07D 277/82 | (2006.01) |
| C07D 513/04 | (2006.01) |

(52) U.S. Cl.
CPC ............ *C12N 5/0657* (2013.01); *C12N 5/10* (2013.01); *C07D 277/82* (2013.01); *C07D 513/04* (2013.01); *C12N 2501/11* (2013.01); *C12N 2501/415* (2013.01); *C12N 2501/727* (2013.01); *C12N 2506/45* (2013.01)

(58) Field of Classification Search
CPC ............ C12N 2500/95; C12N 2501/11; C12N 2501/415; C12N 2501/727; C12N 2506/02; C12N 2506/45; C12N 5/0657
USPC .................................. 435/375, 377
See application file for complete search history.

(56) References Cited

U.S. PATENT DOCUMENTS

| 4,970,318 | A  | 11/1990 | Schnur et al. |
| 8,658,425 | B2 | 2/2014  | Nakatsuji et al. |
| 2003/0134859 | A1 | 7/2003 | Amemiya et al. |
| 2006/0276393 | A1 | 12/2006 | Milburn et al. |
| 2007/0134215 | A1 | 6/2007 | Fukuda et al. |
| 2007/0148185 | A1 | 6/2007 | Rathore et al. |
| 2007/0149466 | A1 | 6/2007 | Milburn et al. |
| 2009/0068742 | A1 | 3/2009 | Yamanaka |
| 2009/0170914 | A1 | 7/2009 | Bomancin et al. |
| 2010/0183565 | A1 | 7/2010 | Laflamme et al. |
| 2012/0244619 | A1 | 9/2012 | Nakatsuji et al. |
| 2013/0183753 | A1 | 7/2013 | Nakatsuji et al. |
| 2013/0274215 | A1 | 10/2013 | Thies et al. |
| 2014/0127807 | A1 | 5/2014 | Nakatsuji et al. |
| 2015/0017718 | A1 | 1/2015 | Nakatsuji et al. |
| 2015/0284683 | A1 | 10/2015 | Shim et al. |
| 2016/0002600 | A1 | 1/2016 | Nakatsuji et al. |

FOREIGN PATENT DOCUMENTS

| EP | 2014766 A1 | 1/2009 |
| JP | S63-190880 A | 8/1988 |
| JP | H02-017181 A | 1/1990 |
| JP | 2000-508919 A | 7/2000 |
| JP | 2001-510450 A | 7/2001 |
| JP | 2004-535199 A | 11/2004 |
| JP | 2005-330443 A | 12/2005 |
| JP | 2006-218035 A | 8/2006 |
| JP | 2007-252220 A | 10/2007 |
| JP | 2009-500357 A | 1/2009 |
| JP | 2009-531365 A | 9/2009 |
| WO | 1997/41209 A1 | 11/1997 |
| WO | 98/17267 | 4/1998 |
| WO | 1998/017267 A1 | 4/1998 |
| WO | 01/83427 A1 | 11/2001 |
| WO | 2001/83427 A1 | 11/2001 |
| WO | 03/006950 A2 | 1/2003 |
| WO | 2003/006950 A2 | 1/2003 |
| WO | 2005/037845 A1 | 4/2005 |
| WO | 2007/069666 A1 | 6/2007 |
| WO | 2007/070964 A1 | 6/2007 |
| WO | 2008/118820 A2 | 10/2008 |
| WO | 2009/006930 A1 | 1/2009 |
| WO | 2009/006997 A1 | 1/2009 |

(Continued)

OTHER PUBLICATIONS

Yuasa, S., "ES saibo, iPS saibo karano shinkinbunka", Japanese Circulation Society, vol. 17, No. 2, Sep. 2009, pp. 223-229.

Fukuda, K., "Hito iPS saibo yurai saiseishinkin wo mochiita shinfuzen chiryoho no kakuritsu", May 15, 2012, 42(5), pp. 559-563.

Haraguchi, Y., "O-33-6 Hito iPS saibo no fuyubaiyohou oyobi shinkinsaibo heno bunkayudohou no kentou", Saiseiiryo, vol. 11, suppl Jun. 1, 2012, p. 211.

(Continued)

*Primary Examiner* — Janet L Epps-Smith
(74) *Attorney, Agent, or Firm* — K&L Gates LLP

(57) ABSTRACT

The present invention provides a method for inducing cardiac differentiation of a pluripotent stem cell, which comprises the steps of (1) culturing a pluripotent stem cell in a medium containing a WNT signaling activator and a PKC activator and (2) culturing the cell after the step (1) in a medium containing a WNT signaling inhibitor, a Src inhibitor, and an EGFR inhibitor.

18 Claims, 19 Drawing Sheets

(56) References Cited

FOREIGN PATENT DOCUMENTS

| WO | 2009/007852 A2 | 1/2009 |
|---|---|---|
| WO | 2011/002950 A1 | 1/2011 |
| WO | 2011/071118 A1 | 6/2011 |
| WO | 2011/127164 A2 | 10/2011 |
| WO | 2012/026491 A1 | 3/2012 |
| WO | 2013/111875 A1 | 8/2013 |
| WO | 2014/136519 A1 | 9/2014 |
| WO | 2015/037706 A1 | 3/2015 |

OTHER PUBLICATIONS

Yamauchi, K., et al., "Cardiomyocytes develop from anterior primitive streak cells induced by b-catenin activation and the blockage of BMP signaling in hESCs", Genes to Cells, 2010, 15, pp. 1216-1227.
Translation of Internal Search Report issued in PCT/JP2014/052673, dated Apr. 28, 2014.
Translation of International Preliminary Report on Patentability issued in PCT/JP2014/052673, dated Dec. 2, 2014.
PubChem CID 2694580—National Center for Biotechnology Information, PubChem Compound Database; CID=2694580, http://pubchem.ncbi.nlm.nih.gov/summary/summary.cgi?cid=2694580 (accessed Dec. 21, 2015), create date Jul. 16, 2005.
PubChem CID 2641096—National Center for Biotechnology Information, PubChem Compound Database; CID=2641096, http://pubchem.ncbi.nlm.nih.gov/summary/summary.cgi?cid=2641096 (accessed Dec. 21, 2015), create date Jul. 16, 2005.
PubChem CID 1358256—National Center for Biotechnology Information, PubChem Compound Database; CID=1358256, http://pubchem.ncbi.nlm.nih.gov/summary/summary.cgi?cid=1358256 (accessed Dec. 21, 2015), create date Jul. 11, 2005.
PubChem CID 1220560—National Center for Biotechnology Information, PubChem Compound Database; CID=1220560, http://pubchem.ncbi.nlm.nih.gov/summary/summary.cgi?cid=1220560 (accessed Dec. 21, 2015), create date Jul. 10, 2005.
PubChem CID 8582409—National Center for Biotechnology Information, PubChem Compound Database; CID=8582409, http://pubchem.ncbi.nlm.nih.gov/summary/summary.cgi?cid=8582409 (accessed Dec. 21, 2015), create date Jul. 30, 2006.
Lian, X., et al., "Robust cardiomyocyte differentiation from human pluripotent stem cells via temporal modulation of canonical Wnt signaling", Proc. Natl. Acad. Sci. USA 109, E1848-E1857, 2012.
International Search Report and Written Opinion dated Dec. 9, 2014 issued in International Application No. PCT/JP2014/074233.
English translation of International Preliminary Report on Patentability dated Mar. 15, 2016 issued in International Application No. PCT/JP2014/074233.
Hu and Li, "Convergence between Wnt-b-catenin and EGFR signaling in cancer"; Molecular Cancer 2010, 9:236.
Ronca, R. et al., "Fibroblast growth factor receptor-1 phosphorylation requirement for cardiomyocyte differentiation in murine embryonic stem cells", J. Cell. Mol. Met vol. 13, No. 8A, 2009 pp. 1489-1498.
Zhou, X. et al., "Differentiation of nonbeating embryonic stem cells into beating cardiomyocytes is dependent on downregulation of PKCb and z in concert with upregulation of PKCe", Developmental Biology 255 (2003) 407-422.
Ventura, C. et al., "Protein Kinase C Signaling Transduces Endorphin-Primed Cardiogenesis in GTR1 Embryonic Stem Cells", Circulation Research, 2003, 92, pp. 617-622.
Hakuno, D. et al., "Focal Adhesion Kinase Signaling Regulates Cardiogenesis of Embryonic Stem Cells", Journal of Biological Chemistry, V. 280, No. 47, Nov. 25, 2005, pp. 39534-39544.
Shen, G. et al., "A 2,6-Disubstituted 4-Anilinoquinazoline Derivative Facilitates Cardiomyogenesis of Embryonic Stem Cells", ChemMedChem, 2012, 7, pp. 733-740.
Morisaki, Takayuki, "Shinkinbunka ni okeru bunshikaibogakutekiseigyokiko no kaimeinikansuru kenkyu", Annual Report of the Research on Cardiovascular Diseases (Heisei 15 Nendo), National Cardiovascular Center, Jan. 2005, p. 177.

English Translation of International Preliminary Report on Patentability Chapter I, issued in the corresponding international application No. PCT/JP2015/065643 dated Dec. 6, 2016.
International Search Report issued in the corresponding international application No. PCT/JP2015/065643 dated Aug. 25, 2015.
U.S. Appl. No. 13/777,765, filed Feb. 26, 2013, Method for Promoting Differentiation of Pluripotent Stem Cells Into Cardiac Muscle Cells.
U.S. Appl. No. 14/154,765, filed Jan. 14, 2014, Method for Promoting Differentiation of Pluripotent Stem Cells Into Cardiac Muscle Cells.
U.S. Appl. No. 14/374,453, filed Jul. 24, 2014, Method for Inducing Cardiac Differentiation of Pluripotent Stem Cell.
U.S. Appl. No. 14/772,991, filed Sep. 4, 2015, Composition for Promoting Cardiac Differentiation of Pluripotent Stem Cell Comprising EGFR Inhibitor.
Database Registry[Online]: Chemical Abstracts Service, Columbus, Ohio, USA. [retrieved on Oct. 7, 2011] Retrieved from STN, Registry No. (Entry Date): 1177562-46-7(Aug. 30, 2009), 1147532-35-1(May 19, 2009), 1147404-38-3(May 19, 2009) ,1147337-80-1 (May 19, 2009) , 1136531-24-2 (Apr. 19, 2009), 1136432-34-2(Apr. 19, 2009), 1090781-93-3(Dec. 28, 2008), 1061194-02-2(Oct. 14, 2008), 1061020-56-1 (Oct. 14, 2008), 1031144-38-3 (Jun. 27, 2008), 1031127-32-8(Jun. 27, 2008), 1023259-74-6(May 28, 2008), 1017145-50-4(Apr. 25, 2008), 941864-24-0 (Jul. 10, 2007), 941861-12-7 (Jul. 10, 2007), 940726-30-7 (Jul. 2, 2007), 940660-05-9 (Jul. 2, 2007), 930893-80-4 (Apr. 19, 2007), 930520-52-8(Apr. 17, 2007), 930496-97-2(Apr. 17, 2007), 930025-45-9 (Apr. 13, 2007).
Yang, L., et al., "Human cardiovascular progenitor cells develop from a KDR+ embryonic-stem-cell-derived population", Nature, vol. 453(7194), pp. 524-528 (2008).
Leschik J., et al., "Cardiac commitment of primate embryonic stem cells", Nature Protocol, vol. 3, No. 9, pp. 1381-1387 (2008).
Paul W. Burridge, et al., "A Universal System for Highly Efficient Cardiac Differentiation of Human Induced Pluripotent Stem Cells That Eliminates Interline Variability", PLos ONE, vol. 6, Issue 4, e18293 (2011).
Wang, H., et al., "Cardiac Induction of Embryonic Stem Cells by a Small Molecule Inhibitor of Wnt/b-Catenin Signaling", ACS Chemical Biology, 6(2), pp. 192-197 (2011).
Iwamoto, R., et al., "Heparin-binding EGF-like growth factor and ErbB signaling is essential for heart function", PNAS, vol. 100, No. 6, pp. 3221-3226 (2003).
Minami, I., et al., "A Small Molecule that Promotes Cardiac Differentiation of Human Pluripotent Stem Cells under Defined, Cytokine- and Xeno-free Conditions", Cell Reports, Nov. 29, 2012, d(5), pp. 1448-1460.
Graichen et al., "Enhanced cardiomyogenesis of human embryonic stem cells by a small molecular inhibitor of p38 MAPK", Differentiation (2008) 76:357-370.
Xu et al., "Chemically defined medium supporting cardiomyocyte differentiation of human embryonic stem cells", Differentiation (2008) 76:958-970.
Carlton et al., "Discovery of small molecule agonists for the bombesin receptor subtype 3 (BRS-3) based on an omeprazole lead", Bioorganic & Medicinal Chemistry Letters, 2008, vol. 18, No. 20, pp. 5451-5455.
Bellasio et al., "Substances with potential cardiovascular activity. 2-Acylaminobenzimidazoles with hypotensive activity", Farmaco, Edizione Scientifica, 1973, vol. 28, No. 2, pp. 164-182.
Harsanyi et al., "Reactions of acylcyanamides. I. New synthesis of 2-acylaminobenzoxazoles", Annali di Chimica (Rome, Italy), 1964, vol. 54, No. 11, pp. 1060-1065.
Database Registry [Online] : Chemical Abstracts Service, Columbus, Ohio, [retrieved on Oct. 7, 2011].
Toyama, "ES Saibo×iPS Saibo kara no Shinkin Saibo Bunka×Seisei×Ishoku", Japanese Journal of Transplantation, 2009, vol. 44, No. 3, pp. 219-225.
Thomson et al., "Embryonic Stem Cell Lines Derived from Human Blastocysts", Science, 1998, 282, pp. 1145-1147.
Suemori et al., "Efficient establishment of human embryonic stem cell lines and long-term maintenance with stable karyotype by

(56) References Cited

OTHER PUBLICATIONS enzymatic bulk passage", Biochemical and Biophysical Research Communications, 2006, 345, pp. 926-932.
Thomson et al., "Isolation of a primate embryonic stem cell line", Proc. Natl. Acad. Sci. USA, 1995, vol. 92, pp. 7844-7848.
Thomset al., "Pluripotent Cell Lines Derived from Common Marmoset (*Callithrix jacchus*) Blastocysts1", Biology of Reproduction, 1996, 55, pp. 254-259.
Doetshman et al., "Establishment of Hamster Blastocyst-Derived Embryonic Stem (ES) Cells", Developmental Biology, 1988, 127,224-227.
Evans et al., "Derivation and Preliminary Chabacterization of Pluripotent Cell Lines From Porcine and Bovine Blastocysts", Theriogenology, 1990, vol. 33, No. 1, pp. 125-128.
Piedrahita et al., "On the Isolation of Embryonic Stem Cells: Comparative Behavior of Murine, Porcine and Ovine Embryos", Theriogenology, 1990, vol. 34, No. 5, pp. 879-891.
Saito et al., "Bovine embryonic stem cell-like cell lines cultured over several passages", Roux's Arch Dev Biol, 1992, 201, pp. 134-141 Bovine embryonic stem cell-like cell lines cultured over several passages.
Sukoyan et al., "Isolation and Cultivation of Blastocyst-Derived Stem Cell Lines From American Mink (*Mustela vision*)", Molecular Reproduction and Development, 1992, 33, pp. 418-431.
Kim et al., "Pluripotent stem cells induced from adult neural stem cells by reprogramming with two factors", Nature, 2008, vol. 454, pp. 646-650.
Kim et al., "Oct4-Induced Pluripotency in Adult Neural Stem Cells", Cell, 2009, 136, pp. 411-419.
Huangfu et al., "Induction of pluripotent stem cells from primary human fibroblasts with only Oct4 and Sox2", Nature Biotechnology, 2008, vol. 26, pp. 1269-1275.
Feng et al., "Reprogramming of fibroblasts into induced pluripotent stem cells with orphan nuclear receptor Esrrb", Nature Cell Biology, 2009, vol. 11, pp. 197-203.
Hanna et al., "Direct Reprogramming of Terminally Differentiated Mature B Lymphocytes to Pluripotency", Cell, 2008, 133, pp. 250-264.
Takahashi et al., "Induction of Pluripotent Stem Cells from Adult Human Fibroblasts by Defined Factors", Cell, 2007, 131, pp. 861-872.
Stuckwisch et al., "Some N-Substituted Dimethoxyphenylacetamides and Dimethoxyphenylethylamines", J. Med. Chem. (1965) 8(5): 734-735.
Search result of STN-Registry data base for "RN:308294-59-9", "RN:349132-90-7", "RN:805285-70-5", "RN:349438-98-8","RN:953930-37-5", "RN:953995-50-1" and "RN:953993-61-8", Mar. 2014.
Asai, Y., Tada, M., Otsuji, T.G. & Nakatsuji, N. Combination of functional cardiomyocytes derived from human stem cells and a highly-efficient microelectrode array system: an ideal hybrid model assay for drug development. Curr Stem Cell Res Ther 5, 227-232 (2010).
Berge ten Derk, et al., "Embryonic stem cells require Wnt proteins to prevent differentiation to epiblast stem cells", Nature Cell Biol., 2011, vol. 13, No. 9, p. 1070-1075.
Burridge, P.W. et al. A universal system for highly efficient cardiac differentiation of human induced pluripotent stem cells that eliminates interline variability. PLoS One 6, e18293 (2011).
Chen, B. et al. Small molecule-mediated disruption of Wnt-dependent signaling in tissue regeneration and cancer. Nat Chem Biol 5, 100-107 (2009).
Chien, K.R., Damian, I.J. & Parker, K.K. Cardiogenesis and the complex biology of regenerative cardiovascular medicine. Science 322, 1494-1497 (2008).
Chien, K.R., Moretti, A. & Laugwitz, K.L. Development. ES cells to the rescue. Science 306, 239-240 (2004).
Even, M.S., Sandusky, C.B. & Barnard, N.D. Serum-free hybridoma culture: ethical, scientific and safety considerations. Trends Biotechnol 24, 105-108 (2006).

English Translation of IPRP dated Jul. 29, 2014 issued in corresponding International Application No. PCT/JP2013/051644.
English Translation of IPRP dated Mar. 19, 2013 issued in corresponding International Application No. PCT/JP2011/069054.
English Translation of ISR issued in corresponding International Application No. PCT/JP2013/051644 (2013).
Gonzalez Rodolfo, et al., "Stepwise Chemically Induced Cardiomyocyte Specification of Human Embryonic Stem Cells", Angew. Chem. Int. Ed., 2011, vol. 50, p. 11181-11185.
Gotea, V. & Ovcharenko, I. DiRE: identifying distant regulatory elements of co-expressed genes. Nucleic Acids Res 36, W133-139 (2008).
Hansson, E.M., Lindsay, M.E. & Chien, K.R. Regeneration next: toward heart stem cell therapeutics. Cell Stem Cell 5, 364-377 (2009).
Hao, J. et al. Dorsomorphin, a selective small molecule inhibitor of BMP signaling, promotes cardiomyogenesis in embryonic stem cells. PLoS One 3, e2904 (2008).
Ichida, J.K. et al. A small-molecule inhibitor of tgf-Beta signaling replaces sox2 in reprogramming by inducing nanog. Cell Stem Cell 5, 491-503 (2009).
Irion, S., Nostra, M.C., Kattman, S.J. & Keller, G.M. Directed differentiation of pluripotent stem cells: from developmental biology to therapeutic applications. Cold Spring Harb Symp Quant Biol 73, 101-110 (2008).
Jacot, J.G., Martin, J.C. & Hunt, D.L. Mechanobiology of cardiomyocyte development. J Biomech 43, 93-98 (2010).
Kamisuki, S. et al. A small molecule that blocks fat synthesis by inhibiting the activation of SREBP. Chem Biol 16, 882-892 (2009).
Kattman, S.J. et al. Stage-specific optimization of activin/nodal and BMP signaling promotes cardiac differentiation of mouse and human pluripotent stem cell lines. Cell Stem Cell 8, 228-240 (2011).
Laflamme, M.A. & Murry, C.E. Heart regeneration. Nature 473, 326-335 (2011).
Lluis Frederic, et al., "Periodic Activation of Wnt/beta-Catenin Signaling Enhances Somatic Cell Reprogramming Mediated by Cell Fusion", Cell Stem Cell, 2008, vol. 3, p. 493-507.
Lutolf, M.P., Gilbert, P.M. & Blau, H.M. Designing materials to direct stem-cell fate. Nature 462, 433-441 (2009).
Menasche, P. Stem cell therapy for heart failure: are arrhythmias a real safety concern? Circulation 119, 2735-2740 (2009).
Mignone, J.L., Kreutziger, K.L., Paige, S.L. & Murry, C.E. Cardiogenesis from human embryonic stem cells. Circ J 74, 2517-2526 (2010).
Murakami, G. et al. Chemical library screening identifies a small molecule that downregulates SOD1 transcription for drugs to treat amyotrophic lateral sclerosis. J Biomol Screen 16, 405-414 (2011).
Naito, A.T. et al. Developmental stage-specific biphasic roles of Wnt/beta-catenin signaling in cardiomyogenesis and hematopoiesis. Proc Natl Acad Sci U S A 103, 19812-19817 (2006).
OA dated Apr. 29, 2014 issued in Chinese Patent Application 201180051572.7 along with its English translation.
Otsuji, T.G. et al. Progressive maturation in contracting cardiomyocytes derived from human embryonic stem cells: Qualitative effects on electrophysiological responses to drugs. Stem Cell Res 4, 201-213 (2010).
Paige, S.L. et al. Endogenous Wnt/beta-catenin signaling is required for cardiac differentiation in human embryonic stem cells. PLoS One 5, e11134 (2010).
Passier, R., van Laake, L.W. & Mummery, C.L. Stem-cell-based therapy and lessons from the heart. Nature 453, 322-329 (2008).
Qyang, Y. et al. The renewal and differentiation of Isl1+ cardiovascular progenitors are controlled by a Wnt/beta-catenin pathway. Cell Stem Cell 1, 165-179 (2007).
Rajala, K., Pekkanen-Mattila, M. & Aalto-Setala, K. Cardiac differentiation of pluripotent stem cells. Stem Cells Int 2011, 383709 (2011).
Ren, Y. et al. Small molecule Wnt inhibitors enhance the efficiency of BMP-4-directed cardiac differentiation of human pluripotent stem cells. J Mol Cell Cardiol 51, 280-287 (2011).
Sato, A., Kawazoe, Y., Kamisuki, S. & Uesugi, M. Synthesis of synthetic small molecule transcription factors (STF). Nucleic Acids Symp Ser (Oxf), 29-30 (2006).

(56) References Cited

OTHER PUBLICATIONS

Sato, S., Murata, A., Shirakawa, T. & Uesugi, M. Biochemical target isolation for novices: affinity-based strategies. Chem Biol 17, 616-623 (2010).

Segers, V.F. & Lee, R.T. Stem-cell therapy for cardiac disease. Nature 451, 937-942 (2008).

Smith, K. P. et al., Pluripotency: toward a gold standard for human ES and iPS cells, J Cell Physiol 220, 21-29 (2009).

Srivastava, D. & Ivey, K.N. Potential of stem-cell-based therapies for heart disease. Nature 441, 1097-1099 (2006).

Suemori, H. & Nakatsuji, N. Generation and characterization of monkey embryonic stem cells. Methods Mol Biol 329, 81-89 (2006).

Suemori, H. et al. Establishment of embryonic stem cell lines from cynomolgus monkey blastocysts produced by IVF or ICSI. Dev Dyn 222, 273-279 (2001).

Suessbrich, H., Waldegger, S., Lang, F. & Busch, A.E. Blockade of HERG channels expressed in Xenopus oocytes by the histamine receptor antagonists terfenadine and astemizole. FEBS Lett 385, 77-80 (1996).

Wada Keiki et al., "Hito Tanosei Kansaibo Kabu (ES Oyobi iPS Saibo Kabu) o Mochiita Bunka Yudo Gijutsu Oyobi HTS eno Oyo Tenkai", Medicine and Drug Journal, 2010, vol. 46, S-1, pp. 247-253.

Willems, E. et al. Small-molecule inhibitors of the Wnt pathway potently promote cardiomyocytes from human embryonic stem cell-derived mesoderm. Circ Res 109, 360-364 (2011).

Xu, Y., Shi, Y. & Ding, S. A chemical approach to stem-cell biology and regenerative medicine. Nature 453, 338-344 (2008).

Yamashita, J.K. ES and iPS cell research for cardiovascular regeneration. Exp Cell Res 316, 2555-2559 (2010).

Yoshida, Y. & Yamanaka, S. iPS cells: a source of cardiac regeneration. J Mol Cell Cardiol 50, 327-332 (2011).

Zhu, W. et al. IGFBP-4 is an inhibitor of canonical Wnt signalling required for cardiogenesis. Nature 454, 345-349 (2008).

Office Action dated Aug. 3, 2015 issued in U.S. Appl. No. 14/374,453.

Biechele et al, Porcupine homolog is required for canonical Wnt signaling and gastrulation in mouse embryos, Developmental Biology 355 (2011) 275-285.

Okita et al, Induced pluripotent stem cells: opportunities and challenges, Phil. Trans. R. Soc. B (2011) 366, 2198-2207.

Database Registry [online]:Chemical Abstracts Service, Columbus, Ohio, USA [retrieved on Feb. 19, 2013] Retrieved from STN, Registry No. (Entry Date): 1177562-46-7(Aug. 30, 2009), 1136531-24-2(Apr. 19, 2009), 1136432-3.4-2(.Apr. 19, 2009), 1023259-74-6(May 28, 2008).

Mummery et al., "Differentiation of Human Embryomic Stem Cells to Cardiomyocytes: Role of Coculture With Visceral Endoderm-Like Cells", Circulation, American Heart Association, 2003, 107, pp. 2733-2740.

Notarianni E. et al., "Derivation of pluripotent, embryonic cell lines from the pig and sheep", J. Reprod. Fert. Suppl. 43: 255-260 (1991)).

Notarianni E. et al., "Maintenance and differentiation in culture of pluripotential embryonic cell lines from pig blastocysts", Journals of Reproduction & Fertility 41: 51-56 (1990).

Sci Planner 2013, Chemical Abstracts Service, Columbus, OH,: RN-1118807-13-8 Downloaded Sep. 24, 2013.

Sci Planner 2013, Chemical Abstracts Service, Columbus, OH,: RN-349132-98-5 Downloaded Sep. 27, 2013.

Shamblott, et al., "Derivation of pluripotent stem cells from cultured human primordial germ cells" Proc. Natl. Acad. Sci. USA vol. 95, pp. 13726-13731, Nov. 1998.

Shi et al., "Induction of Pluripotent Stem Cells from Mouse Embryonic Fibroblasts by Oct4 and Klf4 with Small-Molecule Compounds", Cell Stem Cell 3(5): 568-574 (2008).

Talbot N. C. et al., "Culturing the epiblast cells of the pig blastocyst", Cell. Dev. Biol. 29A: 543-554 (1993).

Yu, J. et al. Induced pluripotent stem cell lines derived from human somatic cells. Science 318, 1917-1920 (2007).

Yuasa, S. et al. "Transient inhibition of BMP signaling by Noggin induces cardiomyocyte differentiation of mouse embryonic stem cells" . Nat Biotechnol 23, 607-611 (2005).

Zhao et al., "Two Supporting Factors Greatly Improve the Efficiency of Human iPSC Generation", Cell Stem Cell 3: 475-479 (2008).

Zhou et al., "Generation of Induced Pluripotent Stem Cells Using Recombinant Proteins", Cell Stem Cell 4(5): 381-384 (2009).

Extended European Search Report dated Aug. 7, 2015 issued in the corresponding European Patent Application No. 13740826.6.

Extended European Search Report dated Feb. 17, 2014 issued in the related European application No. 11819954.6.

Takayuki Morisaki, "Shinkinbunka niokeru bunshi kaibogakuteki seigyokiko no kaimei nikansuru kenkyu", Annual report of the research on cardiobascular diseases, Jan. 2005, p. 177.

Wang, Z., et al., "Neuregulin-1 enhances differentiation of cardiomyocytes from embryonic stem cells", Med. Biol. Eng. Comput., 2009, 47, pp. 41-48.

Minami, I., et al., "O-2-3 Shinkiteibunshikagoubutsu wo mochiita hitoES/iPSsaibo no rinsho gread shinkinbunkayudoho no kaihatsu", Saiseiiryo vol. 12 Suppl. 2013, p. 151.

Yamashita, J., "Differentiation of cardiovascular cells from iPS cells", IGAKU no AYUMI, Dec. 31, 2011, vol. 239, No. 14, pp. 1416-1421.

METHOD FOR INDUCING CARDIAC DIFFERENTIATION OF PLURIPOTENT STEM CELL WITH LOW-MOLECULAR COMPOUNDS

TECHNICAL FIELD

The present invention relates to a method for inducing cardiac differentiation of a pluripotent stem cell with low-molecular compounds, and a kit therefor.

BACKGROUND

Cardiovascular diseases are the leading cause of death in the world. Cardiac transplantation, which is currently the sole therapeutic option for severe heart failure patients, suffers from donor shortage. A potential alternative therapeutic option to the cardiac transplantation is transplantation of cardiomyocytes derived from pluripotent stem cells such as iPS and ES cells. Practical use of the alternative therapy is highly desired. However, before practically using cardiomyocytes derived from pluripotent stem cells in tissue engineering, problems of safety and preparation cost must be resolved.

For the transplantation of cardiomyocytes to a human, it is estimated that at least as much as $10^9$ cells are necessary. However, currently available methods for inducing cardiac differentiation of pluripotent stem cells require proteins such as growth factors, cytokines and serum albumin in vast amounts, and are highly expensive. More specifically, for preparing $10^9$ cardiomyocytes, at least ten liters of culture media are necessary, which would cost more than ten million yen. Actually, currently commercially available cardiomyocytes derived from human pluripotent stem cells are as expensive as several hundred thousand yen per $10^6$ cells, which corresponds to that the $10^9$ cells required for a single transplantation procedure cost several hundred million yen. Therefore, if the cost of the culture media necessary for inducing the cardiac differentiation is reduced, the cardiac tissue engineering will become more practical.

The culture media currently used in the induction of cardiac differentiation of pluripotent stem cells comprise cytokines or proteins and is potentially accompanied by safety problems. In particular, the proteins are obtained from animal cells, bacteria or yeast, and are potentially contaminated with viruses, mycoplasmas, prions or the like from the host cells. However, such contamination must be eliminated from the step of inducing cardiac differentiation of pluripotent stem cells, because the cardiomyocytes from this step are directly provided for the transplantation into a patient.

CITATION LIST

Patent Literature

PTL 1: WO 2012/026491 (incorporated herein by reference)
PTL 2: WO 2013/111875 (incorporated herein by reference)
PTL 3: US 2013/0183753 A (incorporated herein by reference)
PTL 4: U.S. Pat. No. 8,658,425 B (incorporated herein by reference)
PTL 5: US 2014/0127807 A (incorporated herein by reference)

Non Patent Literature

NPL 1: Minami, I. et al., Cell reports 2, 1448-1460 (2012) (incorporated herein by reference)

SUMMARY

An object of the present invention is to provide a method for inducing cardiac differentiation of a pluripotent stem cell with low-molecular compounds.

The present invention provides the following embodiments.
1. A method for inducing cardiac differentiation of a pluripotent stem cell, which comprises the steps of (1) culturing a pluripotent stem cell in a medium containing a WNT signaling activator and a PKC activator and (2) culturing the cell after the step (1) in a medium containing a WNT signaling inhibitor, a Src inhibitor, and an EGFR inhibitor. 2. The method of item 1, wherein the WNT signaling inhibitor is a compound of Formula (I):
2.

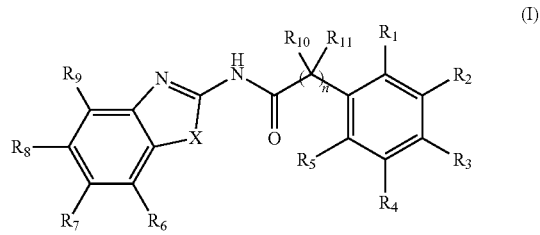

wherein
$R_1$ to $R_5$ are each independently a hydrogen atom; a halogen atom; a hydroxyl group; a linear or branched alkoxy group having 1 to 5 carbon atoms; a linear or branched alkyl group having 1 to 5 carbon atoms which is unsubstituted or substituted with a halogen atom; or a group —$NR_{12}R_{13}$, wherein $R_{12}$ and $R_{13}$ are each independently a hydrogen atom, an oxygen atom, or a linear or branched alkyl group having 1 to 5 carbon atoms which is unsubstituted or substituted with a halogen atom; wherein two adjacent groups among $R_1$ to $R_5$ may join together to form —O—$CH_2$—O— or —O—$(CH_2)_2$—O—;
$R_6$ to $R_9$ are each independently a hydrogen atom; a halogen atom; a hydroxyl group; a linear or branched alkoxy group having 1 to 5 carbon atoms; a linear or branched alkoxy group having 1 to 5 carbon atoms which is substituted with a group —C(O)A, wherein A is a saturated or unsaturated 5- or 6-membered ring which is unsubstituted or substituted with a linear or branched alkyl group having 1 to 5 carbon atoms and the ring may contain 1 or 2 atoms independently selected from a nitrogen atom, an oxygen atom and a sulfur atom; a linear or branched alkyl group having 1 to 5 carbon atoms which is unsubstituted or substituted with a halogen atom; or a group —$NR_{12}R_{13}$, wherein $R_{12}$ and $R_{13}$ are each independently a hydrogen atom, an oxygen atom, or a linear or branched alkyl group having 1 to 5 carbon atoms which is unsubstituted or substituted with a halogen atom; wherein two adjacent groups among $R_6$ to $R_9$ may join together to form —O—$CH_2$—O— or —O—$(CH_2)_2$—O—;
$R_{10}$ to $R_{11}$ are each independently a hydrogen atom; or a linear or branched alkyl group having 1 to 5 carbon atoms;

X is —CR$_{14}$, wherein R$_{14}$ is a hydrogen atom, a halogen atom, a hydroxyl group, a linear or branched alkoxy group having 1 to 5 carbon atoms, or a linear or branched alkyl group having 1 to 5 carbon atoms which is unsubstituted or substituted with a halogen atom; an oxygen atom; a sulfur atom; a selenium atom; or a group —NR$_{15}$, wherein R$_{15}$ is a hydrogen atom, a linear or branched alkyl group having 1 to 5 carbon atoms, or a linear or branched acyl group having 1 to 5 carbon atoms; and n is an integer of 0 to 6;

or a salt thereof.

3. The method of item 2, wherein

R$_1$, R$_4$, R$_5$, R$_6$, R$_9$, R$_{10}$, and R$_{11}$ are a hydrogen atom;

R$_2$ and R$_3$ are each independently a methoxy group, an ethoxy group or a propoxy group;

R$_7$ is a hydrogen atom; a halogen atom; a hydroxyl group; a linear or branched alkoxy group having 1 to 5 carbon atoms; a linear or branched alkoxy group having 1 to 5 carbon atoms which is substituted with a group —C(O)A, wherein A is a saturated or unsaturated 5- or 6-membered ring which is unsubstituted or substituted with a linear or branched alkyl group having 1 to 5 carbon atoms and the ring may contain 1 or 2 atoms independently selected from a nitrogen atom, an oxygen atom and a sulfur atom; a linear or branched alkyl group having 1 to 5 carbon atoms which is unsubstituted or substituted with a halogen atom; or a group —NR$_{12}$R$_{13}$, wherein R$_{12}$ and R$_{13}$ are each independently a hydrogen atom, an oxygen atom, or a linear or branched alkyl group having 1 to 5 carbon atoms which is unsubstituted or substituted with a halogen atom;

R$_8$ is a hydrogen atom; a halogen atom; a hydroxyl group; a linear or branched alkoxy group having 1 to 5 carbon atoms; a linear or branched alkyl group having 1 to 5 carbon atoms which is unsubstituted or substituted with a halogen atom;

or R$_7$ and R$_8$ join together to form —O—CH$_2$—O— or —O—(CH$_2$)$_2$—O—;

X is a sulfur atom, and n is an integer of 0 to 4.

4. The method of Item 2, wherein

R$_1$, R$_4$, R$_5$, R$_6$, R$_8$, R$_9$, R$_{10}$, and R$_{11}$ are a hydrogen atom;

R$_2$ and R$_3$ are each independently a methoxy group, an ethoxy group or a propoxy group;

R$_7$ is a hydrogen atom; a halogen atom; a hydroxyl group; a linear or branched alkoxy group having 1 to 5 carbon atoms; a linear or branched alkoxy group having 1 to 5 carbon atoms which is substituted with a group —C(O)A, wherein A is a saturated or unsaturated 5- or 6-membered ring which is unsubstituted or substituted with a linear or branched alkyl group having 1 to 5 carbon atoms and the ring may contain 1 or 2 atoms independently selected from a nitrogen atom, an oxygen atom and a sulfur atom; a linear or branched alkyl group having 1 to 5 carbon atoms which is unsubstituted or substituted with a halogen atom; or a group —NR$_{12}$R$_{13}$, wherein R$_{12}$ and R$_{13}$ are each independently a hydrogen atom, an oxygen atom, or a linear or branched alkyl group having 1 to 5 carbon atoms which is unsubstituted or substituted with a halogen atom;

X is a sulfur atom, and n is an integer of 0 to 4.

5. The method of item 4, wherein R.sub.7 is a halogen atom.

6. The method of any one of items 3-5, wherein n is an integer of 1 to 4.

7. The method of item 1, wherein the WNT signaling inhibitor is a compound selected from the group consisting of:

KY02111

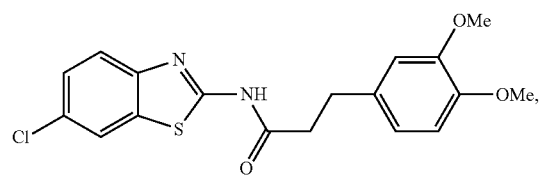

KY01041

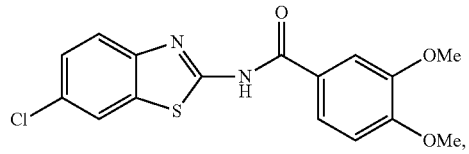

T61164

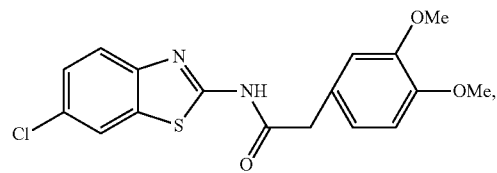

KY02114

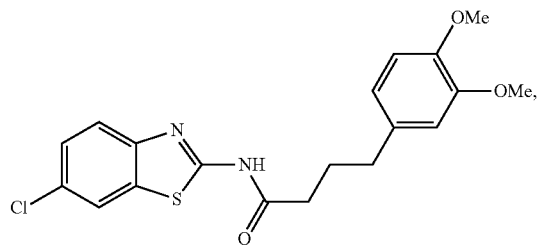

KY01045

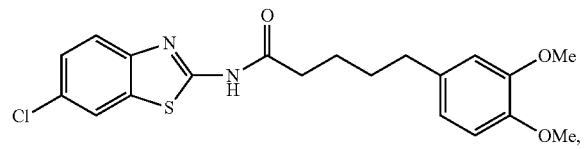

KY01040

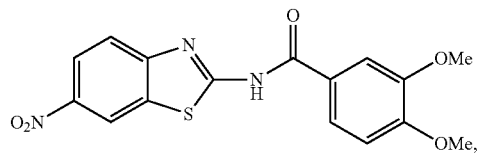

-continued
KY02109
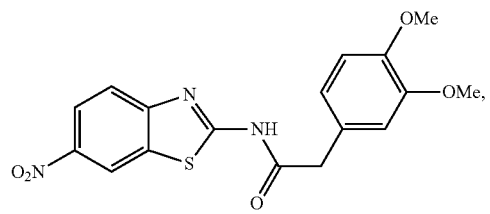
KY01042
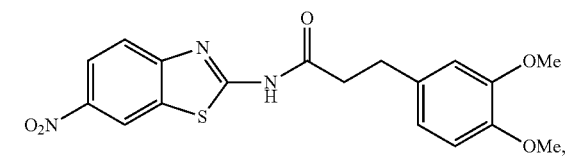
KY01043
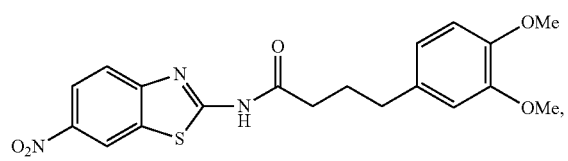
KY01046
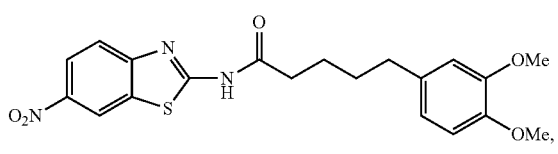
PB2852
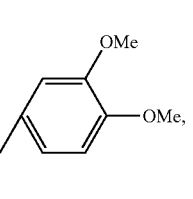
N11474
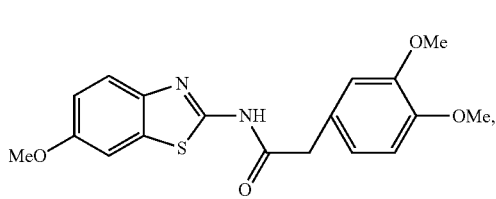
PB2572
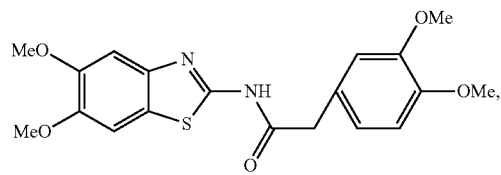
PB2570
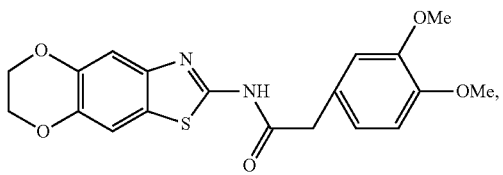
KY02104
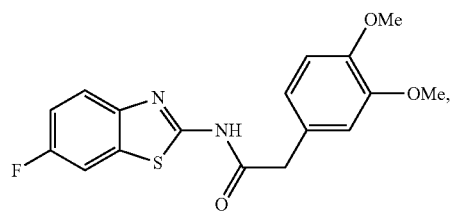
SO087
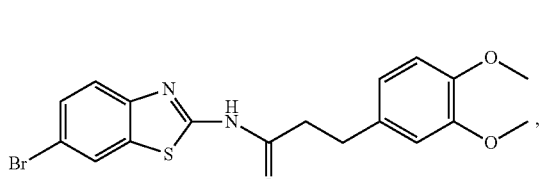
SO102
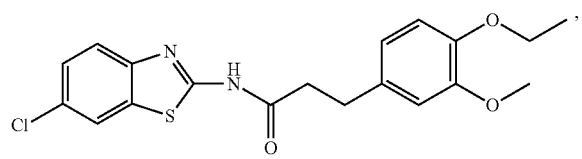
SO096
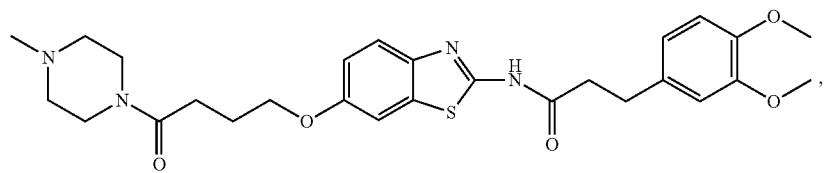
SOO094
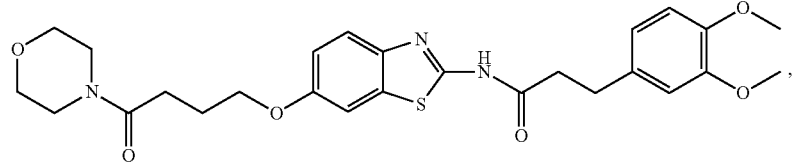

-continued

SO3031 (KY01-I)

SO2031 (KY02-I)

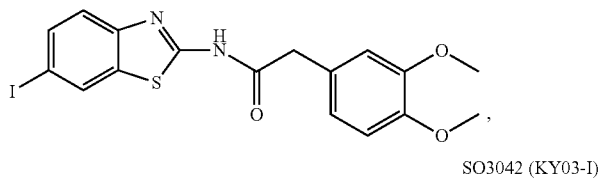

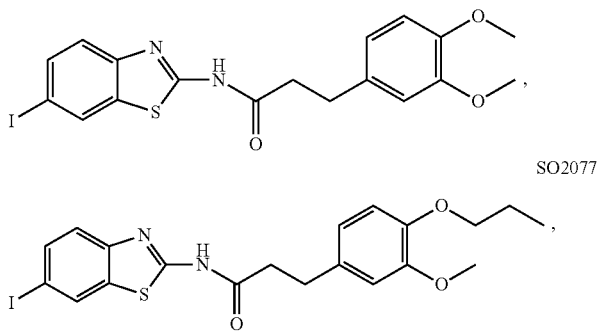

SO3042 (KY03-I)

SO2077

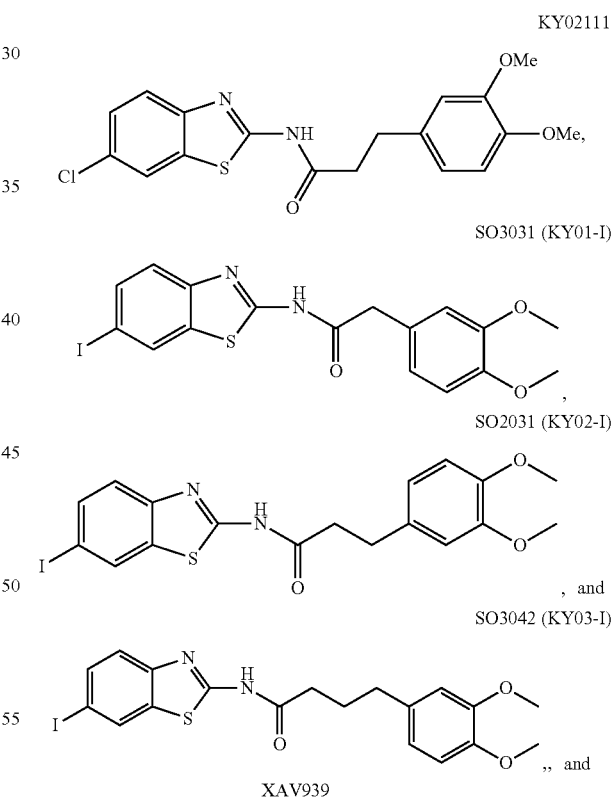

or a salt thereof. 8. The method of item 7, wherein the WNT signaling inhibitor is KY02111, SO3031 (KY01-I), SO2031 (KY02-I) or SO3042 (KY03-I). 9. The method of item 8, wherein the WNT signaling inhibitor is SO3042 (KY03-I). 10. The method of any one of items 1-9, wherein the medium of step (2) comprises two or more WNT signaling inhibitors, and wherein one of the two or more WNT signaling inhibitors is the compound of Formula (I) or a salt thereof as recited in any one of items 2-9, and one or more of the two or more WNT signaling inhibitors are selected from the group consisting of IWP2, XAV939, and IWR1. 11. The method of item 10, wherein the two or more WNT signaling inhibitors are the compound of Formula (I) or a salt thereof as recited in any one of items 2-9 and XAV939. 12. The method of any one of items 1-11, wherein the WNT signaling activator is BIO or CHIR99021. 13. The method of item 12, wherein the WNT signaling activator is CHIR99021. 14. The method of any one of items 1-13, wherein the PKC activator is PMA or prostratin. 15. The method of any one of items 1-14, wherein the PKC activator is PMA. 16. The method of any one of items 1-15, wherein the Src inhibitor is A419259 or SU6656. 17. The method of any one of items 1-16, wherein the Src inhibitor is A419259. 18. The method of any one of items 1-17, wherein the EGFR inhibitor is AG1478 or gefitinib. 19. The method of any one of items 1-18, wherein the EGFR inhibitor is AG1478. 20. The method of any one of items 1-19, wherein
 the WNT signaling activator is CHIR99021,
 the PKC activator is PMA,
 the WNT signaling inhibitor comprises a compound selected from KY02111, SO3031 (KY01-I), SO2031 (KY02-I), and SO3042 (KY03-I), and XAV939,
 the Src inhibitor is A419259, and
 the EGFR inhibitor is AG1478.
21. The method of item 20, wherein the WNT signaling inhibitor comprises SO3042 (KY03-I) and XAV939. 22. The method of any one of items 1-21, wherein the media of the steps (1) and (2) do not contain any protein or peptide component. 23. The method of any one of items 1-22, wherein the culturing of the steps (1) and (2) is in suspension culture. 24. The method of any one of items 1-23, wherein the culturing of the step (1) is for 1 to 3 days and the culturing of the step (2) is for 2 to 13 days. 25. The method of any one of items 1-24, wherein the pluripotent stem cell is a monkey or human pluripotent stem cell. 26. The method of item 25, wherein the pluripotent stem cell is a monkey or human ES cell or iPS cell. 27. The method of any one of items 1-26, which is used to prepare a cardiomyocyte. 28. A cardiomyocyte obtained by the method of any one of items 1-27. 29. A kit for promoting cardiac differentiation comprising a WNT signaling activator, a PKC activator, a WNT signaling inhibitor, a Src inhibitor, and an EGFR inhibitor. 30. The kit of item 29, wherein
 the WNT signaling activator is CHIR99021,
 the PKC activator is PMA,
 the WNT signaling inhibitor comprises a compound selected from the Src inhibitor is A419259, and
 the EGFR inhibitor is AG1478.
31. The kit of item 30, wherein the WNT signaling inhibitor comprises SO3042 (KY03-I) and XAV939.

According to the present invention, cardiac differentiation of pluripotent stem cells is induced with low-molecular compounds efficiently and inexpensively.

DESCRIPTION OF EMBODIMENTS

Figure 1A:
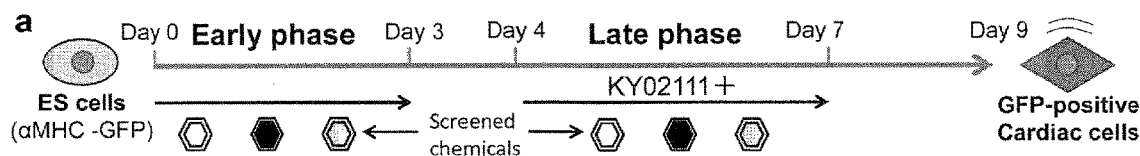
FIG. 1a: A scheme of chemical screening.

The term "pluripotent stem cell" herein used refers to a cell having an ability to differentiate any type of cell constituting an adult body (pluripotency) and self-renewal capacity which is an ability to maintain the pluripotency during cell division. The "pluripotent stem cell" includes an embryonic stem cell (an ES cell), an embryonic germ cell (an EG cell), and an induced pluripotent stem cell (an iPS cell). The "pluripotent stem cell" may be a cell of any species with no limitation, and preferably a mammalian cell, and more preferably a rodent or primate cell. The present invention is particularly suitable for a monkey or human pluripotent stem cell.

An ES cell is a pluripotent stem cell derived from early embryo and may be established from inner cell mass of a blastocyst or post-implantation epiblast in early embryo. Examples of the ES cell include those described in the following references: human (Thomson J. A. et al., Science 282: 1145-1147 (1998), Biochem Biophys Res Commun. 345(3), 926-32 (2006); primates such as rhesus macaque and marmoset (Thomson J. A. et al., Proc. Natl. Acad. Sci. USA 92: 7844-7848 (1995); Thomson J. A. et al., Biol. Reprod. 55: 254-259 (1996)); rabbit (National Publication of International Patent Application No. 2000-508919); hamster (Doetshman T. et al., Dev. Biol. 127: 224-227 (1988)), hog (Evans M. J. et al., Theriogenology 33: 125128 (1990); Piedrahita J. A. et al., Theriogenology 34: 879-891 (1990); Notarianni E. et al., J. Reprod. Fert. 40: 51-56 (1990); Talbot N. C. et al., Cell. Dev. Biol. 29A: 546-554 (1993)), sheep (Notarianni E. et al., J. Reprod. Bert. Suppl. 43: 255-260 (1991)), cow (Evans M. J. et al., Theriogenology 33: 125-128 (1990); Saito S. et al., Roux. Arch. Dev. Biol. 201: 134-141 (1992)), and mink (Sukoyan M. A. et al., Mol. Reorod. Dev. 33: 418-431 (1993)) (these references are herein incorporated by reference). For example, ES cells such as CMK6.4, KhES-1, KhES-3, KhES-4, KhES-5, H1, and H9 may be used as the ES cell.

An EG cell is a pluripotent stem cell derived from a primordial germ cell, and examples include a human EG cell (Shamblott, et al., Proc. Natl. Acad. Sci USA 95: 13726-13731 (1998)) (the reference is herein incorporated by reference).

The term "iPS cell" herein used refers to a pluripotent stem cell induced from a cell other than a pluripotent stem cell such as a somatic cell and a tissue stem cell. Methods for preparing the iPS cell are described in the following references, for example: WO2007/069666, WO2009/006930, WO2009/006997, WO2009/007852, WO2008/118820, Cell Stem Cell 3(5): 568-574 (2008), Cell Stem Cell 4(5): 381-384 (2009), Nature 454: 646-650 (2008), Cell 136(3):411-419 (2009), Nature Biotechnology 26: 1269-1275 (2008), Cell Stem Cell 3: 475-479 (2008), Nature Cell Biology 11: 197-203 (2009), Cell 133(2): 250-264 (2008), Cell 131(5): 861-72 (2007), Science 318 (5858): 1917-20 (2007) (these references are herein incorporated by reference). In addition, any cell prepared by any method is included in the "iPS cell" of the present invention as long as it is an artificially-induced pluripotent stem cell. iPS cells such as IMR90-1, IMR90-4, 201B7, and 253G1 may be used.

The "WNT signaling activator" as used herein refers to a substance that activates the WNT signaling pathway. Examples of the WNT signaling activator include a GSK3β inhibitor such as BIO, CHIR99021, and TWS119. In one embodiment, the WNT signaling activator is CHIR99021 or BIO, and preferably CHIR99021. In the present invention, two or more WNT signaling activators may be used in combination, for example both of CHIR99021 and BIO may be used.

The "WNT signaling inhibitor" as used herein refers to a substance that inhibits the WNT signaling pathway. Examples of the WNT signaling inhibitor include the compound of formula (I) or a salt thereof as described in WO2012/026491, compounds such as IWP2, IWP4, XAV939, and IWR1. In the present invention, two or more WNT signaling inhibitors may be used in combination. In one embodiment, one of the two or more WNT signaling inhibitors is the compound of formula (I) or a salt thereof as described in WO2012/026491, and the other is one or more compounds selected from IWP2, XAV939, and IWR1, and preferably XAV939. All of the two or more WNT signaling inhibitors may be the compounds of formula (I) or salts thereof as described in WO2012/026491.

The compound of formula (I) as described in WO2012/026491 (the reference is herein incorporated by reference) is as follows:

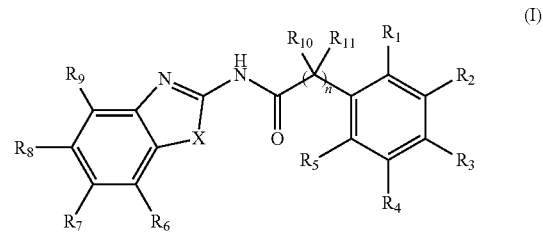

wherein $R_1$ to $R_5$ are each independently a hydrogen atom; a halogen atom; a hydroxyl group; a linear or branched alkoxy group having 1 to 5 carbon atoms; a linear or branched alkyl group having 1 to 5 carbon atoms which is unsubstituted or substituted with a halogen atom; or a group —$NR_{12}R_{13}$, wherein $R_{12}$ and $R_{13}$ are each independently a hydrogen atom, an oxygen atom, or a linear or branched alkyl group having 1 to 5 carbon atoms which is unsubstituted or substituted with a halogen atom; wherein two adjacent groups among $R_1$ to $R_5$ may join together to form —O—$CH_2$—O— or —O—$(CH_2)_2$—O—, $R_6$ to $R_9$ are each independently a hydrogen atom; a halogen atom; a hydroxyl group; a linear or branched alkoxy group having 1 to 5 carbon atoms; a linear or branched alkoxy group having 1 to 5 carbon atoms which is substituted with a group —C(O)A, wherein A is a saturated or unsaturated 5- or 6-membered ring which is unsubstituted or substituted with a linear or branched alkyl group having 1 to 5 carbon atoms and the ring may contain 1 or 2 atoms independently selected from a nitrogen atom, an oxygen atom and a sulfur atom; a linear or branched alkyl group having 1 to 5 carbon atoms which is unsubstituted or substituted with a halogen atom; or a group —$NR_{12}R_{13}$, wherein $R_{12}$ and $R_{13}$ are each independently a hydrogen atom, an oxygen atom, or a linear or branched alkyl group having 1 to 5 carbon atoms which is unsubstituted or substituted with a halogen atom; wherein two adjacent groups among $R_6$ to $R_9$ may join together to form —O—$CH_2$—O— or —O—$(CH_2)_2$—O—, $R_{10}$ to $R_{11}$ are each independently a hydrogen atom; or a linear or branched alkyl group having 1 to 5 carbon atoms, X is —$CR_{14}$, wherein $R_{14}$ is a hydrogen atom, a halogen atom, a hydroxyl group, a linear or branched alkoxy group having 1 to 5 carbon atoms, or a linear or branched alkyl group having 1 to 5 carbon atoms which is unsubstituted or substituted with a halogen atom; an oxygen atom; a sulfur atom; a selenium atom; or a group —$NR_{15}$, wherein $R_{15}$ is a hydrogen atom, a linear or branched alkyl group having 1 to 5 carbon atoms, or a linear or branched acyl group having 1 to 5 carbon atoms, and n is an integer of 0 to 6.

Examples of the linear or branched alkoxy group having 1 to 5 carbon atoms include a methoxy group, an ethoxy group, a propoxy group, an isopropoxy group, a butoxy group, an isobutoxy group, a sec-butoxy group, a tert-butoxy group and a pentyloxy group.

Examples of the linear or branched alkyl group having 1 to 5 carbon atoms include a methyl group, an ethyl group, a propyl group, an isopropyl group, a butyl group, an isobutyl group, a sec-butyl group, a tert-butyl group and a pentyl group.

Examples of the linear or branched acyl group having 1 to 5 carbon atoms include a formyl group, an acetyl group, a propionyl group, a butyryl group, an isobutyryl group, a valeryl group and an isovaleryl group.

Examples of the halogen atom include Cl, Br, I or F.

In a preferred embodiment, $R_1$ to $R_5$ are each independently a hydrogen atom; a halogen atom; a hydroxyl group; a linear or branched alkoxy group having 1 to 5 carbon atoms; or a linear or branched alkyl group having 1 to 5 carbon atoms which is unsubstituted or substituted with a halogen atom; wherein two adjacent groups among $R_1$ to $R_5$ may join together to form —O—$CH_2$—O— or —O—$(CH_2)_2$—O—.

$R_2$ and $R_3$ are preferably a linear or a branched alkoxy group having 1 to 5 carbon atoms or join together to form —O—$CH_2$—O— or —O—$(CH_2)_2$—O—. More preferably, $R_2$ and $R_3$ are each independently a methoxy group, an ethoxy group or a propoxy group, and further preferably a methoxy group.

$R_1$, $R_4$ and $R_5$ are preferably a hydrogen atom.

In one embodiment, $R_6$ to $R_9$ are each independently a hydrogen atom; a halogen atom; a hydroxyl group; a linear or branched alkoxy group having 1 to 5 carbon atoms; a linear or branched alkyl group having 1 to 5 carbon atoms which is unsubstituted or substituted with a halogen atom; or a group —$NR_{12}R_{13}$, wherein $R_{12}$ and $R_{13}$ are each independently a hydrogen atom, an oxygen atom, or a linear or branched alkyl group having 1 to 5 carbon atoms which is unsubstituted or substituted with a halogen atom; wherein two adjacent groups among $R_6$ to $R_9$ may join together to form —O—$CH_2$—O— or —O—$(CH_2)_2$—O—.

$R_6$ and $R_9$ are preferably each independently a hydrogen atom; a halogen atom; a hydroxyl group; a linear or branched alkoxy group having 1 to 5 carbon atoms; or a linear or branched alkyl group having 1 to 5 carbon atoms which is unsubstituted or substituted with a halogen atom, more preferably a hydrogen atom.

In a preferred embodiment, $R_7$ is a hydrogen atom; a halogen atom; a hydroxyl group; a linear or branched alkoxy group having 1 to 5 carbon atoms; a linear or branched alkoxy group having 1 to 5 carbon atoms which is substituted with a group —C(O)A, wherein A is a saturated or unsaturated 5- or 6-membered ring which is unsubstituted or substituted with a linear or branched alkyl group having 1 to 5 carbon atoms and the ring may contain 1 or 2 atoms independently selected from a nitrogen atom, an oxygen atom and a sulfur atom; a linear or branched alkyl group having 1 to 5 carbon atoms which is unsubstituted or substituted with a halogen atom; or a group —$NR_{12}R_{13}$, wherein $R_{12}$ and $R_{13}$ are each independently a hydrogen atom, an oxygen atom, or a linear or branched alkyl group having 1 to 5 carbon atoms which is unsubstituted or substituted with a halogen atom; $R_8$ is a hydrogen atom; a halogen atom; a hydroxyl group; a linear or branched alkoxy group having 1 to 5 carbon atoms; or a linear or branched alkyl group having 1 to 5 carbon atoms which is unsubstituted or substituted with a halogen atom; or $R_7$ and $R_8$ join together to form —O—$CH_2$—O— or —O—$(CH_2)_2$—O—.

In one embodiment, $R_7$ is a linear alkoxy group having 1 to 5 carbon atoms which is substituted with a group —C(O)A, and the group —C(O)A binds to the terminal carbon atom of the alkoxy group.

In a preferred embodiment, A contains at least one nitrogen atom, and examples of such A include a pyrrolidinyl, imidazolidinyl, pyrazolidinyl, pyrrolyl, imidazolyl, pyrazolyl, thiazolyl, isothiazolyl, oxazolyl, isooxazolyl, piperidinyl, piperazinyl, morpholinyl, pyridyl, pyrimidinyl, pyrazinyl and pyridazinyl groups which are unsubstituted or substituted with a linear or branched alkyl group having 1 to 5 carbon atoms. In a more preferred embodiment, A is a piperidinyl group, a piperazinyl group or a morpholinyl group which is unsubstituted or substituted with a linear or branched alkyl group having 1 to 5 carbon atoms. In a further preferred embodiment, A is a piperidin-1-yl group, a piperazin-1-yl group or a morpholin-4-yl group which is unsubstituted or substituted with a linear or branched alkyl group having 1 to 5 carbon atoms.

$R_{10}$ and $R_{11}$ are preferably a hydrogen atom.

In one embodiment, n is an integer of 0 to 4, 1 to 4, or 1 to 3, or n is 2 or 3.

In one embodiment, X is an oxygen atom; a sulfur atom; or a group —$NR_{15}$, wherein $R_{15}$ is a hydrogen atom, a linear or branched alkyl group having 1 to 5 carbon atoms, a linear or branched acyl group having 1 to 5 carbon atoms. X is preferably a sulfur atom.

In one embodiment, the compound of formula (I) is the one:
wherein $R_1$, $R_4$, $R_5$, $R_6$, $R_9$, $R_{10}$ and $R_{11}$ are a hydrogen atom, $R_2$ and $R_3$ are each independently a methoxy group, an ethoxy group or a propoxy group, $R_7$ is a hydrogen atom; a halogen atom; a hydroxyl group; a linear or branched alkoxy group having 1 to 5 carbon atoms; a linear or branched alkoxy group having 1 to 5 carbon atoms which is substituted with a group —C(O)A, wherein A is a saturated or unsaturated 5- or 6-membered ring which is unsubstituted or substituted with a linear or branched alkyl group having 1 to 5 carbon atoms and the ring may contain 1 or 2 atoms independently selected from a nitrogen atom, an oxygen atom and a sulfur atom; a linear or branched alkyl group having 1 to 5 carbon atoms which is unsubstituted or substituted with a halogen atom; or a group —$NR_{12}R_{13}$, wherein $R_{12}$ and $R_{13}$ are each independently a hydrogen atom, an oxygen atom, or a linear or branched alkyl group having 1 to 5 carbon atoms which is unsubstituted or substituted with a halogen atom, $R_8$ is a hydrogen atom; a halogen atom; a hydroxyl group; a linear or branched alkoxy group having 1 to 5 carbon atoms; or a linear or branched alkyl group having 1 to 5 carbon atoms which is unsubstituted or substituted with a halogen atom, or $R_7$ and $R_8$ may join together to form —O—$CH_2$—O— or —O—$(CH_2)_2$—O—, X is a sulfur atom, and n is an integer of 0 to 4, preferably 1 to 4.

In one embodiment, the compound of formula (I) is the one:
wherein $R_1$, $R_4$, $R_5$, $R_6$, $R_8$, $R_9$, $R_{10}$ and $R_{11}$ are a hydrogen atom, $R_2$ and $R_3$ are each independently a methoxy group, an ethoxy group or a propoxy group, $R_7$ is a hydrogen atom; a halogen atom; a hydroxyl group; a linear or branched alkoxy group having 1 to 5 carbon atoms; a linear or branched alkoxy group having 1 to 5 carbon atoms which is substituted with a group —C(O)A, wherein A is a saturated or unsaturated 5- or 6-membered ring which is unsubstituted or substituted with a linear or branched alkyl group having 1 to 5 carbon atoms and the ring may contain 1 or 2 atoms independently selected from a nitrogen atom, an oxygen atom and a sulfur atom; a linear or branched alkyl group having 1 to 5 carbon atoms which is unsubstituted or substituted with a halogen atom; or a group —$NR_{12}R_{13}$, wherein $R_{12}$ and $R_{13}$ are each independently a hydrogen atom, an oxygen atom, or a linear or branched alkyl group having 1 to 5 carbon atoms which is unsubstituted or substituted with a halogen atom, X is a sulfur atom, and n is an integer of 0 to 4, preferably 1 to 4.

In one embodiment, the compound of formula (I) is the one:
wherein $R_1$, $R_4$, $R_5$, $R_6$, $R_8$, $R_9$, $R_{10}$ and $R_{11}$ are a hydrogen atom, R7 is a halogen atom, $R_2$ and $R_3$ are each independently a methoxy group, an ethoxy group or a propoxy group, X is a sulfur atom, n is an integer of 0 to 4, preferably 1 to 4.

In one embodiment, the compound of formula (I) is the one:
wherein $R_1$, $R_4$, $R_5$, $R_6$, $R_8$, $R_9$, $R_{10}$ and $R_{11}$ are a hydrogen atom, R7 is a halogen atom, $R_2$ and $R_3$ are a methoxy group, X is a sulfur atom, and n is an integer of 0 to 4, preferably 1 to 4.

In one embodiment, the compound of formula (I) is selected from the following group:

KY02111

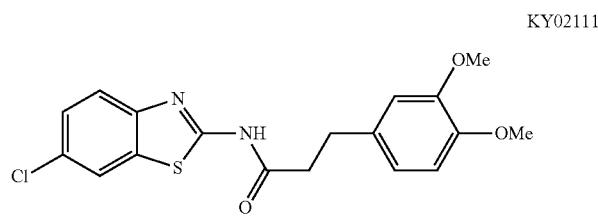

KY01041

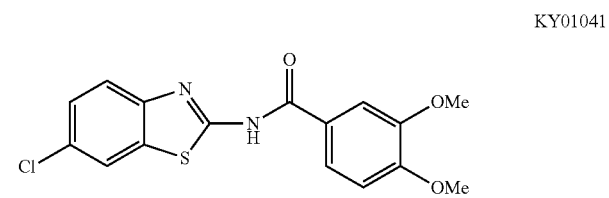

T61164

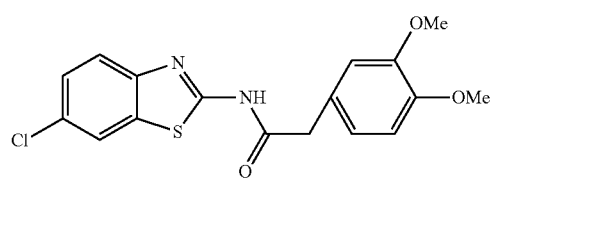

KY02114

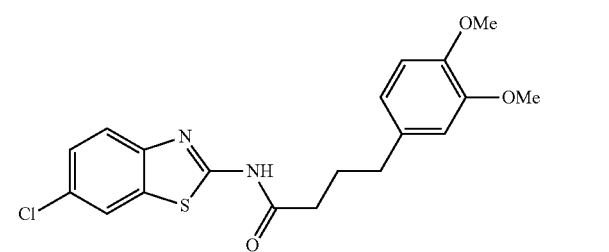

KY01045

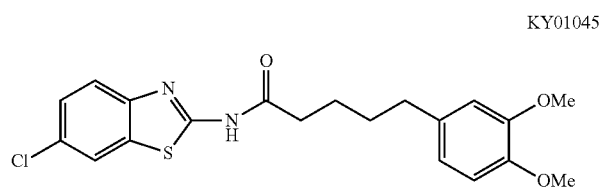

KY01040

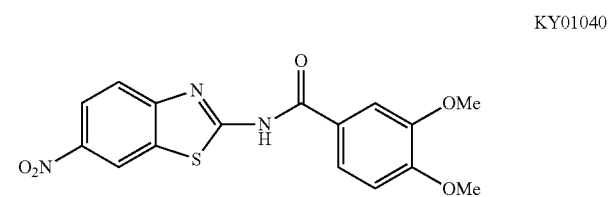

KY02109

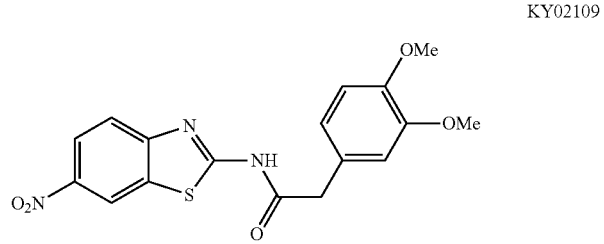

KY01042

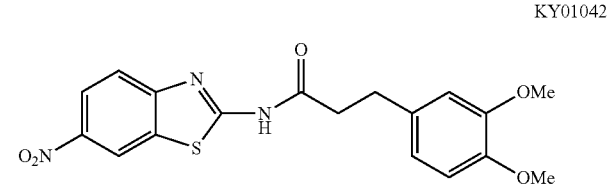

-continued
KY01043
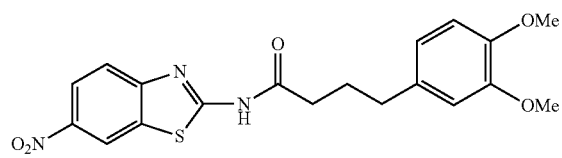
KY01046
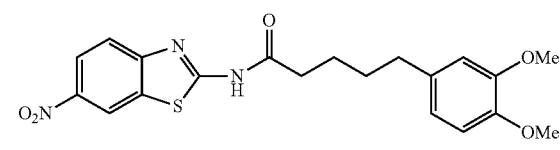
PB2852
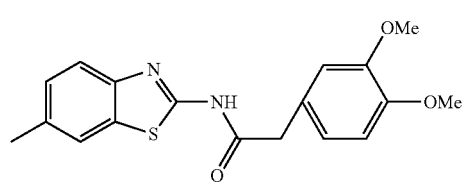
N11474
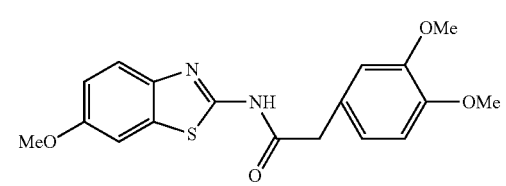
PB2572
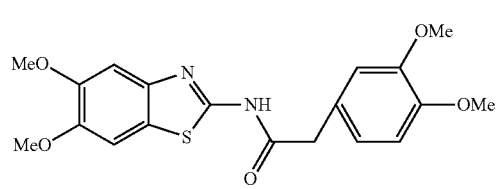
PB2570
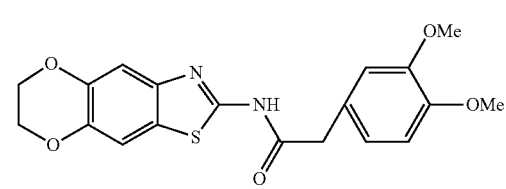
KY02104
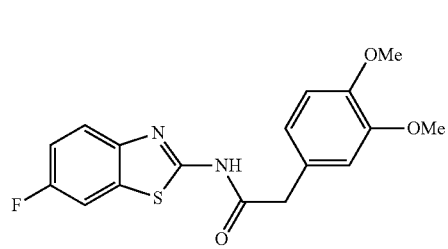
SO087
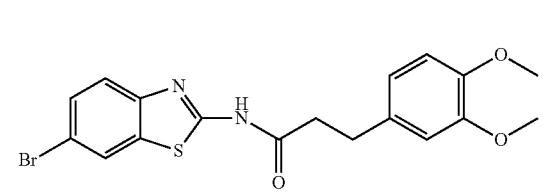
SO102
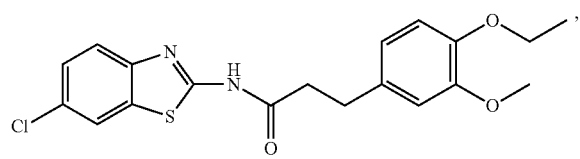
SO096
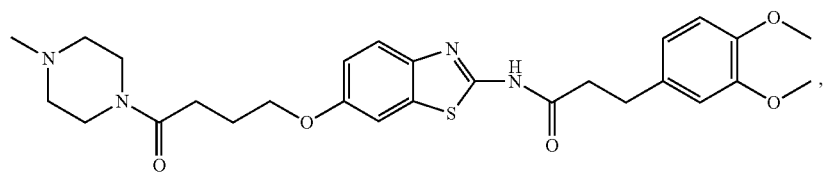
SOO094
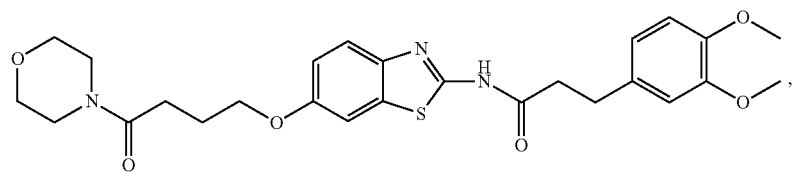
SO3031 (KY01-I)
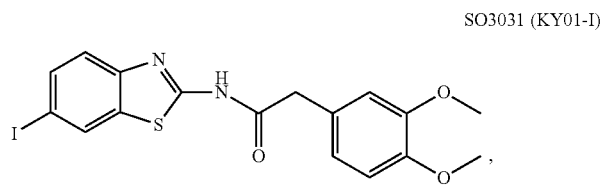
SO2031 (KY02-I)
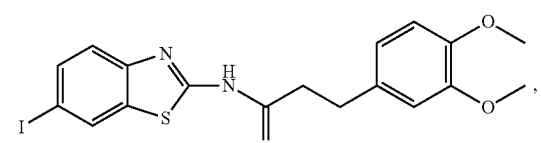

-continued

SO3042 (KY03-I)

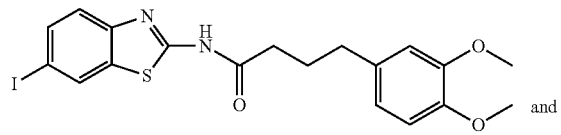

and

SO2077

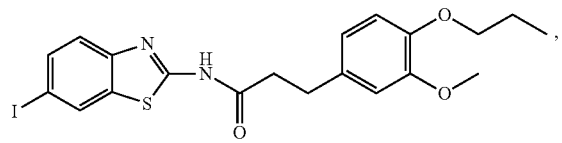

The compound of formula (I) is preferably KY02111, SO3031 (KY01-I), SO2031 (KY02-I), or SO3042 (KY03-I), more preferably KY02111 or SO3042 (KY03-I), even more preferably SO3042 (KY03-I).

The compound of Formula (I) may be synthesized by a known method (J. Med. Chem., 1965, 8 (5), pp 734-735) (incorporated herein by references) or in accordance with the methods described in WO2012/026491 (incorporated herein by references). Also, they are available, for example, from UkrOrgSynthesis Ltd. (PB2852, PB2572, and PB2570) and ENAMINE (161164). Alternatively, they are available, for example, from UkrOrgSynthesis Ltd. (PB2852, PB2572, and PB2570) and ENAMINE (T61164).

The "PKC activator" refers to a substance that activates the signaling pathway of protein kinase C (PKC) or downstream therefrom. Examples of the PKC activator include Phorbol 12-myristate 13-acetate (PMA), prostratin, Bryostatin 1, Bryostatin 2, FR236924, (−)-Indolactam V, PEP005, Phorbol 12,13-dibutyrate, SC-9, SC-10, 1-Oleoyl-2-acetyl-sn-glycerol, 1-O-Hexadecyl-2-O-arachidonyl-sn-glycerol, 1-O-Hexadecyl-2-O-arachidonyl-sn-glycerol, 1,2-Dioctanoyl-sn-glycerol, PIP2, Resiniferatoxin, Phorbol 12,13-Dihexanoate, Mezerein, Ingenol 3-Angelate, RHC-80267, DCP-LA and Lipoxin A4. In one embodiment, the PKC activator is a phorbol ester-type PKC activator such as PMA, prostratin, PEP005, Phorbol 12,13-dibutyrate, Resiniferatoxin, Phorbol 12,13-Dihexanoate, Mezerein, or Ingenol 3-Angelate. In the invention, two or more PKC activators may be used in combination. In a preferred embodiment, the PKC activator is PMA or prostratin, more preferably PMA.

The "Src inhibitor" refers to a substance that inhibits the signaling pathway of protein Src or downstream therefrom. Examples of the Src inhibitor include A419259, SU6656, PP1, 1-Naphthyl PP1, PP2, Indirubin-3'-(2,3-dihydroxypropyl)-oximether, TX-1123, Src Kinase Inhibitor I (CAS 179248-59-0), AZM475271, Bosutinib, Herbimycin A, KB SRC 4, MNS, PD166285 and TC-S7003. In one embodiment, the Src inhibitor is A419259, KB SRC 4, SU6656, or Indirubin-3'-(2,3-dihydroxypropyl)-oximether. In the invention, two or more Src inhibitors may be used in combination. In a preferred embodiment, the Src inhibitor is A419259 or SU6656, more preferably A419259.

The "EGF receptor inhibitor" (also described as EGFR inhibitor) refers to a substance that inhibits signaling from EGF receptor. Examples of the EGF receptor inhibitor include AG1478, gefitinib, afatinib, ARRY334543, AST1306, AZD8931, BIBU1361, BIBX1382, BPDQ, BPIQ-I, BPIQ-II, canertinib, CL-387,785, CUDC101, dacomitinib, vandetanib, EGFR inhibitor III (N-(4-((3,4-dichloro-6-fluorophenyl)amino)-quinazoline-6-yl)-2-chloroacetamide, CAS 733009-42-2), EGFR/ErbB-2 inhibitor (4-(4-benzyloxyanilino)-6,7-dimethoxyquinazoline, CAS 179248-61-4), erlotinib, GW583340, GW2974, HDS029, lapatinib, WHI-P154, OSI-420, PD153035, PD168393, PD174265, pelitinib, Compound 56, XL657, PP3, AG-490, AG555, tyrphostin B42, tyrphostin B44, AG556, AG494, AG825, RG-13022, DAPH, EGFR Inhibitor (cyclopropanecarboxylic acid (3-(6-(3-trifluoromethyl-phenylamino)-pyrimidin-4-ylamino)-phenyl)-amide, CAS 879127-07-8), erbstatin analog (methyl 2,5-dihydroxycinnamate, CAS 63177-57-1), JNJ28871063, tyrphostin 47, lavendustin A, lavendustin C, lavendustin C methylate, LFM-A12, TAK165, TAK285, tyrphostin 51, tyrphostin AG183, tyrphostin AG528, tyrphostin AG99, tyrphostin RG14620, WZ3146, WZ4002, WZ8040, butein, and tyrphostin AG112. In one embodiment, the EGF receptor inhibitor is an EGF receptor inhibitor having quinazoline structure, such as AG1478, gefitinib, afatinib, ARRY334543, AST1306, AZD8931, BIBU1361, BIBX1382, BPDQ, BPIQ-I, BPIQ-II, canertinib, CL-387,785, CUDC101, dacomitinib, vandetanib, EGFR inhibitor III (CAS 733009-42-2), EGFR/ErbB-2 inhibitor (CAS 179248-61-4), erlotinib, GW583340, GW2974, HDS029, lapatinib, WHI-P154, OSI-420, PD153035, PD168393, PD174265, pelitinib, Compound 56, or XL657. In an preferred embodiment, the EGF receptor inhibitor is AG1478 or gefitinib, more preferably AG1478. EGF receptor inhibitors may be obtained, for example, from Santa Cruz Biotech.

The method for inducing cardiac differentiation of a pluripotent stem cell provided by the present invention is carried out in vitro. The medium used in the method of the present invention may be any conventional medium used for cardiac differentiation (i.e., "cardiac differentiation medium") of pluripotent stem cells and the medium is not limited to those having specific composition. The medium preferably does not contain protein or peptide components although the medium may contain such components. The medium in the present invention contains, for example, IMDM medium and/or DMEM medium, MEM non-essential amino acid solution, and L-glutamine. In one embodiment, the medium contains IMDM medium and DMEM medium (preferably IMDM:DMEM=1:1), MEM non-essential amino acid solution, and L-Glutamine. The medium may contain L-carnitine, ascorbic acid, and/or creatine in addition to IMDM medium and/or DMEM medium, MEM non-essential amino acid solution, and L-glutamine. In a preferable embodiment, the medium contains IMDM medium and DMEM medium (preferably IMDM:DMEM=1:1), MEM non-essential amino acid solution, L-glutamine, L-carnitine, ascorbic acid, and creatine. The medium also may contain antibiotics, such as penicillin-streptomycin as required. Examples of the medium include IMDM and DMEM-based medium used in the examples (containing 242 ml IMDM, 242 ml DMDM, 5 ml MEM non-essential amino acid solution (×100), 5 ml penicillin-streptomycin (×100), 5 ml 0.2 M L-glutamine, 100 μl 1M L-carnitine, 50 mg ascorbic acid and 1 ml 0.5 M creatine).

Also, the method of the present invention may use other types of medium, such as a known cardiac differentiation medium based on IMDM medium (for example, a medium containing 200 ml IMDM medium, 50 ml bovine fetal serum, 2.5 ml MEM non-essential amino acid solution (×100), 2.5 ml of 200 mM L-glutamine, 2 µl 2-mercaptoethanol, 255 µl 5N NaOH), a known cardiac differentiation medium based on DMEM medium (for example, a medium containing 200 ml DMEM/F12 medium, 50 ml bovine fetal serum, 2.5 ml MEM non-essential amino acid solution (×100), 2.5 ml 200 mM L-glutamine and 2-mercaptoethanol), or StemPro®-34SFM (GIBCO)+BMP4 (10 ng/ml).

In the method of the invention, any conventional culture method suitable for cardiac differentiation of a pluripotent stem cell may be used. Examples of the culture method include adhesion (attachment) culture, floating culture, and suspension culture. In a preferable embodiment, the culturing of the method of the invention is in suspension culture. The cell number of pluripotent stem cells on the start of culture may be appropriately determined by factors such as culture methods, culture vessels and types of cells, the cells may be plated at about $1 \times 10^5$ cells/ml to $10 \times 10^5$ cells/ml. The medium may be replaced once in one to three days, for example once in two days.

In the method of the present invention, the period of each of the steps (1) and (2), and the period from the end of the step (1) to the start of the step (2) may be appropriately determined depending on factors such as types of cells. The step (2) may start just after the end of the step (1), or after a certain period from the end of the step (1). For example, after the end of the step (1), the cell may be cultured in a medium that does not contain a WNT signaling activator, a PKC activator, a WNT signaling inhibitor, a Src inhibitor nor an EGF receptor inhibitor for one or two days, preferably for one day, and then the medium may be replaced with a medium containing a WNT signaling inhibitor, a Src inhibitor and an EGF receptor inhibitor to start the step (2).

For example, in the method of the present invention, the culturing of the step (1) may be for 1 to 3 days, and the step (2) starts just after the end of the step (1), or after 1 or 2 days from the end of the step (1) and the culturing of the step (2) may be for 2 to 13 days, preferably for 3 to 10 days, more preferably for 4 to 10 days, even more for 4 to 8 days. For example, when the first day of the step (1) is Day 0, the step (1) may be from Day 0 to Day 1, Day 0 to Day 2 or Day 0 to Day 3, and the step (2) may be from Day 2 to Day 10 (for 8 days), Day 2 to Day 9 (for 7 days), Day 2 to Day 8 (for 6 days), Day 2 to Day 7 (for 5 days), Day 2 to Day 6 (for 4 days), Day 3 to Day 10 (for 7 days), Day 3 to Day 9 (for 6 days), Day 3 to Day 8 (for 5 days), Day 3 to Day 7 (for 4 days), Day 4 to Day 10 (for 6 days), Day 4 to Day 9 (for 5 days) or Day 4 to Day 8 (for 4 days) just after the end of the step (1), or after 1 or 2 days from the end of the step (1).

Since the step (1) corresponds to early phase of cardiac differentiation at which pluripotent stem cells are differentiated into mesoderm, the period of the step (1) may be determined based on the expression of a mesoderm-related gene. Examples of the mesoderm-related gene include T, MIXL1, and NODAL. The step (2) corresponds to late phase of cardiac differentiation at which the mesoderm is differentiated into cardiomyocytes, and the period may be determined by detecting the differentiation into cardiomyocytes. Differentiation into cardiomyocytes may be detected from, for example, the number of beating cardiac colonies, expression of a cardiac marker, expression of an ion channel, or a response to an electrophysiological stimulus. Examples of the cardiac marker include α-MHC, β-MHC, cTnT, α-actinin, and NKX2.5. Also, examples of the ion channel include HCN4, Nav1.5, Cav1.2, Cav3.2 HERG1b and KCNQ1.

Concentrations of the WNT signaling activator and WNT signaling inhibitor may be appropriately determined depending on the cell and agent used. When the WNT signaling activator is BIO or CHIR99021, for example, the WNT signaling activator may be used at a final concentration of 100 nM to 100 µM, preferably 1 µM to 10 µM. When the WNT signaling inhibitor is IWP2, XAV939, or IWR1, the WNT signaling inhibitor may be used, for example, at a final concentration of 0.5 to 20 µM, preferably 0.5 to 10 µM, more preferably 1 to 10 µM. When the WNT signaling inhibitor is a compound of Formula (I) or a salt thereof, the WNT signaling inhibitor may be used, for example, at a final concentration of 0.1 to 20 µM, preferably 0.1 to 10 µM, more preferably 1 to 10 µM, depending on the compound or salt used.

Concentrations of the PKC activator may be appropriately determined depending on the cell and agent used. When the PKC activator is PMA, for example, the PKC activator may be used at a final concentration of 0.01 µM to 10 µM, preferably 0.03 to 1 µM, more preferably 0.1 to 1 µM. When the PKC activator is prostratin, for example, the PKC activator may be used at a final concentration of 0.1 µM to 100 µM, preferably 1 to 10 µM.

Concentrations of the Src inhibitor may be appropriately determined depending on the cell and agent used. When the Src inhibitor is A419259 or SU6656, for example, the Src inhibitor may be used at a final concentration of 0.1 µM to 10 µM, preferably 0.1 to 3 µM, more preferably 0.3 to 3 µM.

Concentrations of the EGF receptor inhibitor may be appropriately determined depending on the cell and agent used. When the EGF receptor inhibitor is gefitinib or AG1478, for example, the EGF receptor inhibitor may be used at a final concentration of 100 nM to 100 µM, preferably 1 to 20 µM. When the EGF receptor inhibitor is PP3, for example, the EGF receptor inhibitor may be used at a final concentration of 1 µM to 1 mM, preferably 10 µM to 100 µM.

The method of the invention may be used to prepare a cardiomyocyte. Production of a cardiomyocyte may be detected from, for example, the number of beating cardiac colonies, expression of a cardiac marker, expression of an ion channel, or a response to an electrophysiological stimulus. The cardiomyocyte prepared by the method of the invention may be used for evaluation of drug safety in vitro or as a cardiomyocyte for transplant to treat heart diseases.

The kit for cardiac differentiation provided by the present invention comprises a WNT signaling activator, a PKC activator, a WNT signaling inhibitor, a Src inhibitor and an EGF receptor inhibitor, further may comprise components such as medium and culture vessel used in the method of the present invention. The WNT signaling inhibitor, the PKC activator, the WNT signaling inhibitor, the Src inhibitor, and the EGF receptor inhibitor in the kit of the present invention are as described for the method for inducing cardiac differentiation of the invention. In a preferable embodiment, the kit provided by the invention comprise CHIR99021 as a WNT signaling activator, PMA as a PKC activator, SO3042 (KY03-I) and XAV939 as WNT signaling inhibitors, A419259 as a Src inhibitor, and AG1478 as an EGF receptor inhibitor.

The present invention also provides a composition for promoting cardiac differentiation of a pluripotent stem cell containing a PKC activator; use of a PKC activator for manufacturing a composition for promoting cardiac differentiation of a pluripotent stem cell; and a method for inducing cardiac differentiation of a pluripotent stem cell comprising culturing the pluripotent stem cell in a medium containing an PKC activator. The PKC activator may be used in the early phase of cardiac differentiation, for example, for 1 to 3 days from the start of culture in a cardiac differentiation medium. The present invention also provides a composition for promoting cardiac differentiation of a pluripotent stem cell containing a Src inhibitor; use of a Src inhibitor for manufacturing a composition for promoting cardiac differentiation of a pluripotent stem cell; and a method for inducing cardiac differentiation of a pluripotent stem cell comprising culturing the pluripotent stem cell in a medium containing an Src inhibitor. The Src inhibitor may be used in the late phase of inducing cardiac differentiation, for example, for 2 to 13 days from Day 2, Day 3, or Day 4 of culture in a cardiac differentiation medium, preferably for 3 to 10 days, more preferably for 4 to 10 days, even more preferably for 4 to 8 days. In these embodiments, a pluripotent stem cell and medium as previously described may be used.

The present invention is described further in detail with reference to the following examples. The present invention is not limited by the examples in any sense.

Examples

Screening of Compounds

Twenty compounds were tested for the ability of inducing cardiac differentiation of pluripotent stem cell (Table 1). Pluripotent stem cells were cultured in culture media to which the test compounds were added in different concentrations (0.3 μM, 1 μM, 3 μM and 10 μM) in early phase and late phase of differentiation of the cells. Cells from the culture were subjected to GFP fluorometry in accordance with the cardiac differentiation protocol shown in FIG. 1a. Besides the test compounds, 10 μM KY02111 was included in the culture media for the late phase differentiation. The intensity of GFP fluorescence determined in the cells from the control culture, which was cultured with no test compound other than KY02111, was assigned to one. The test compounds which achieved threefold increase or more of the fluorescence intensity compared with the control (i.e., achieved an additive increase of cardiac differentiation compared with KY02111 only) are shown by underlined cells in Table 1. It was found that the cardiac differentiation was promoted by a PKC activator prostratin, a Src inhibitor A419259, and an EGF inhibitor AG1478 under appropriate conditions.

Promotion of Cardiac Differentiation by PKC Activators, EGFR Inhibitors, and Src Inhibitors The scheme of chemical screening is illustrated in FIG. 1a. Compounds were screened for the ability of increasing GFP fluorescence compared with the control (KY02111 alone) using a monkey ES cell line transfected with an αMHC promoter-driven GFP gene (Minami et al., Cell Reports 2, 1448-1460, 2012, which is incorporated herein by reference). The ES cell line was derived from a monkey ES cell line (cynomolgus monkey CMK6.4) by transfecting the cells with a vector which expresses green fluorescent protein (GFP) under control by a promoter of α-MHC gene (a marker of cardiac differentiation). The cells were plated at $4.0 \times 10^5$ cells per well in 6 well plates (Asahi Glass/5816-006: Ezview culture plates) and cultured for nine days in an IMDM-based medium for cardiac differentiation (200 ml IMDM medium (Sigma 13390), with 50 ml calf serum (GIBCO 10099-141), 2.5 ml MEM non-essential amino acid solution (Sigma M7145), 2.5 ml penicillin-streptomycin (DISCO 15140), 2.5 ml 200 mM L-glutamine, 2 ul 2-mercaptoethanol (Sigma M7522), and 255 ul 5N NaOH). Each test compound was added to the medium at different concentrations in the early phase (day 0 to day 3) and the late phase (day 4 to day 7) of cardiac differentiation. Cells obtained from the culture on day 9 were subjected to GFP fluorometry with a Metamorph imaging system.

Figure 1B:
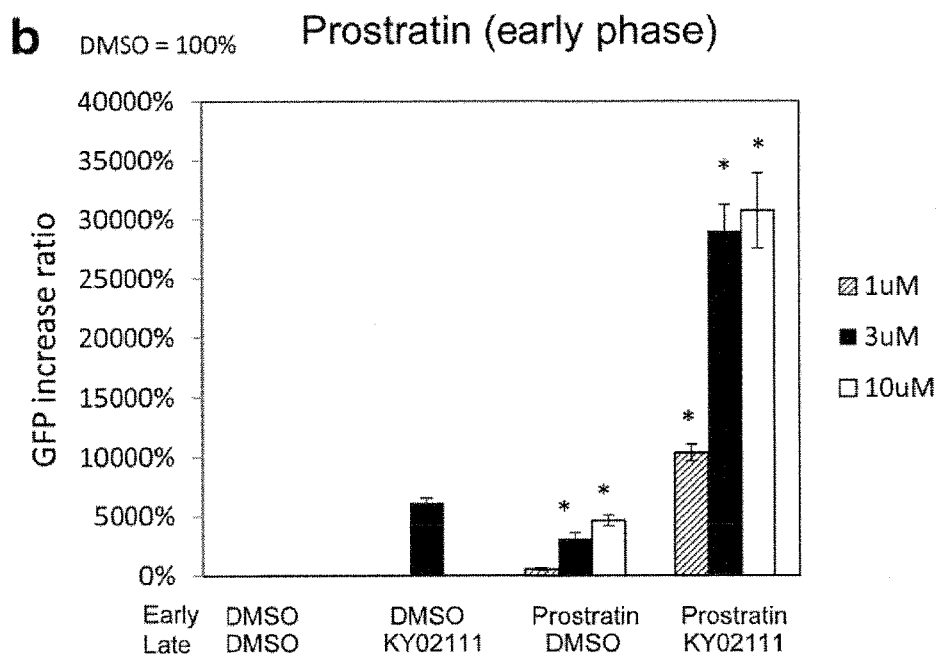
FIG. 1b: The effect of a PKC activator prostratin on cardiac differentiation. *P<0.05 (t-test). Every value was obtained with n=3.
Figure 1C:
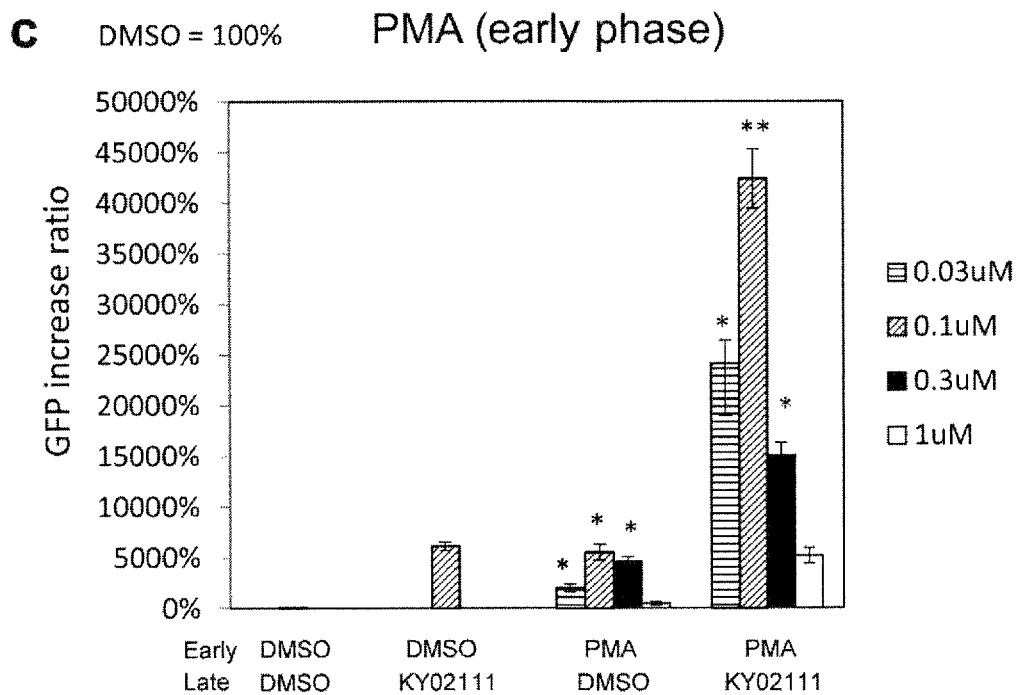
FIG. 1c: The effect of a PKC activator PMA on cardiac differentiation. *P<0.05 (t-test). **P<0.01 (t-test). Every value was obtained with n=3.

PKC Inhibitors prostratin (FIG. 1b) and PMA (FIG. 1C) increased the cardiac differentiation in concentration-dependent manner in the early phase of differentiation. Prostratin (3 to 10 μM) and PMA (0.03 to 0.3 μM) increased the cardiac differentiation three- to eight-fold, alone or in combination with KY02111 (10 μM in the late phase of differentiation) (KY+Prost, and KY+PMA).

Figure 1D:
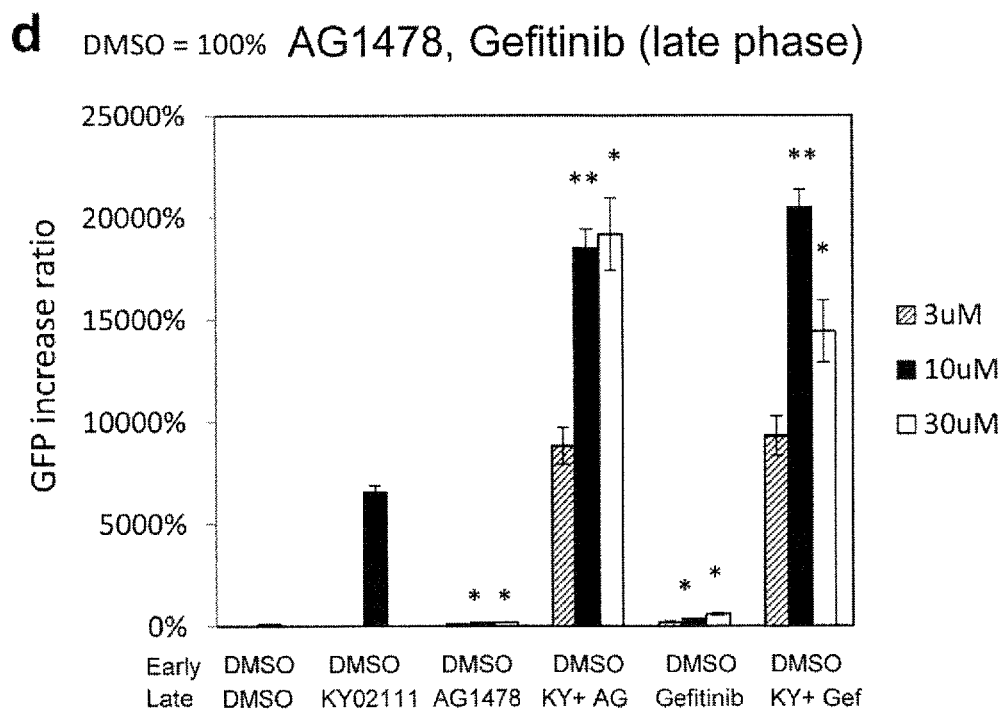
FIG. 1d: The effect of EGF inhibitors AG1478 and gefitinib on cardiac differentiation. *P<0.05 (t-test). **P<0.01 (t-test). Every value was obtained with n=3.
Figure 1E:
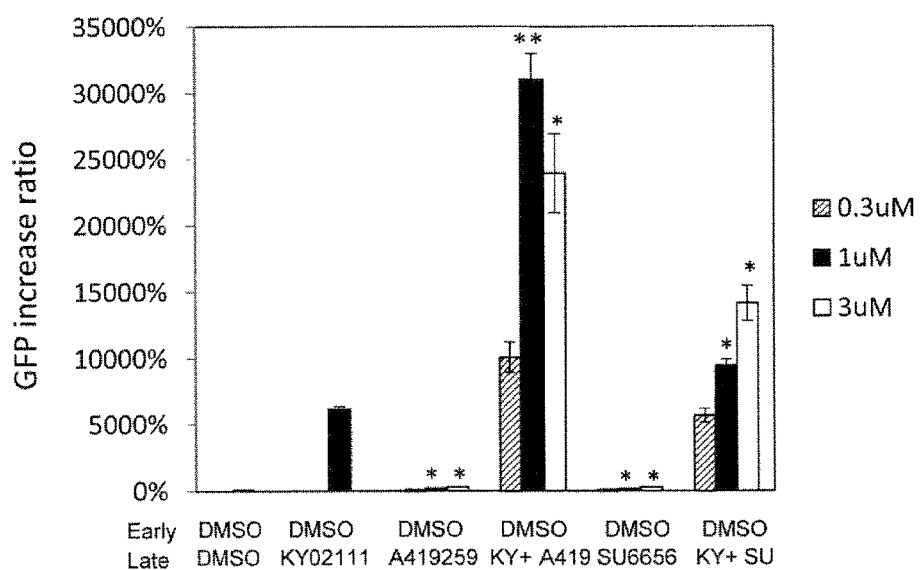
FIG. 1e: The effect of Src inhibitors A419259 and SU6656 on cardiac differentiation. *P<0.05 (t-test). **P<0.01 (t-test). Every value was obtained with n=3.

EGF Inhibitors AG1478 and gefitinib increased the cardiac differentiation in concentration-dependent manner in the late phase of differentiation (FIG. 1d). AG1478 (10 to 30 μM) and gefitinib (10 to 30 μM) increased the cardiac differentiation two- to three-fold, alone or in combination with KY02111 (10 μM in the late phase of differentiation) (KY+AG, and KY+Gef).

Src Inhibitors A419259 and SU6656 increased the cardiac differentiation in concentration-dependent manner in the late

TABLE 1

| Chemical | Function | Phase | 0.3 μM | 1 μM | 3 μM | 10 μM | Phase | 0.3 μM | 1 μM | 3 μM | 10 μM |
| --- | --- | --- | --- | --- | --- | --- | --- | --- | --- | --- | --- |
| PD173074 | FGFR inhibitior | Early | 0.02 | 0 | 0 | 0 | Late | 0.23 | 0.08 | 0 | 0 |
| AS605240 | PI3K inhibitior | Early | 0.65 | 0.84 | 0.32 | 0 | Late | 1.31 | 0.9 | 1.22 | 0.55 |
| Axitinib | VEGFR inhibitor | Early | 0.64 | 0.02 | 0 | 0 | Late | 0.95 | 0.25 | 0.05 | 0 |
| Akt inhibitor 8 | Akt inhibitor | Early | 1.2 | 0.96 | 0.11 | 0 | Late | 1.11 | 1.57 | 1.33 | 1.11 |
| SU5402 | FGFR/VEGFR inhibitor | Early | 0.09 | 0 | 0 | 0 | Late | 0.89 | 1 | 0.46 | 0.06 |
| K00063794 | mTOr inhibitor | Early | 0.18 | 0.01 | 0 | 0 | Late | 0.95 | 0.85 | 0.21 | 0 |
| AG1478 | EGFR inhibitor | Early | 0.97 | 0.89 | 0.35 | 0.05 | Late | 1.24 | 1.53 | 2.03 | <u>3.24</u> |
| SC-1 | Ras/ERK inhibitor | Early | 0.16 | 0 | 0 | 0 | Late | 0.14 | 0 | 0 | 0 |
| 5B431542 | TGF-βR inhibitor | Early | 0.61 | 0.1 | 0 | 0 | Late | 1.2 | 1.52 | 1.44 | 1.58 |
| BIRB796 | P38 MAPK inhibitor | Early | 1.2 | 0.9 | 0.95 | 0.08 | Late | 1.05 | 0.81 | 0.55 | 0.29 |
| PPP | IGFR inhibitor | Early | 0.2 | 0 | 0 | 0 | Late | 0.39 | 0.2 | 0 | 0 |
| A419259 | Src inhibitor | Early | 0.15 | 0.01 | 0 | 0 | Late | 1.7 | <u>5.56</u> | <u>4.8</u> | 0.32 |
| PDGFRiV | PDGFR inhibitor | Early | 0.94 | 1.22 | 1.54 | 2.21 | Late | 0.95 | 0.58 | 1.33 | 0.02 |
| AG490 | JAK inhibitor | Early | 1.5 | 0.59 | 0.79 | 0.72 | Late | 0.92 | 1 | 1.1 | 1.33 |
| PF04217903 | c-Met inhibitor | Early | 1.02 | 0.99 | 0.91 | 0.62 | Late | 1.09 | 1.3 | 0.82 | 0.78 |
| Prostratin | PKC activator | Early | 0.79 | 2.31 | <u>5.42</u> | <u>6.88</u> | Late | 0.72 | 0.3 | 0.01 | 0 |
| ISCK03 | c-Kit inhibitor | Early | 0.08 | 0 | 0 | 0 | Late | 1.23 | 0.8 | 0.79 | 0.88 |
| Go6983 | PKC inhibitor | Early | 1.1 | 0.98 | 2.31 | 2.12 | Late | 1.12 | 0.62 | 0.45 | 0.13 |
| Dorsomorphin | BMPR inhibitor | Early | 0.13 | 0.03 | 0 | 0 | Late | 0.96 | 1.67 | 1.22 | 0.89 |
| Cucurbitaonl | JAK2/STAT3 inhibitor | Early | 0.11 | 0 | 0 | 0 | Late | 1.62 | 0 | 0 | 0 | phase of differentiation. A419259 (1 to 3 µM) and SU6656 (1 to 3 µM) increased the cardiac differentiation two- to five-fold, alone or in combination with KY02111 (10 µM in the late phase of differentiation) (KY+A419, and KY+SU66).

Figure 1F:
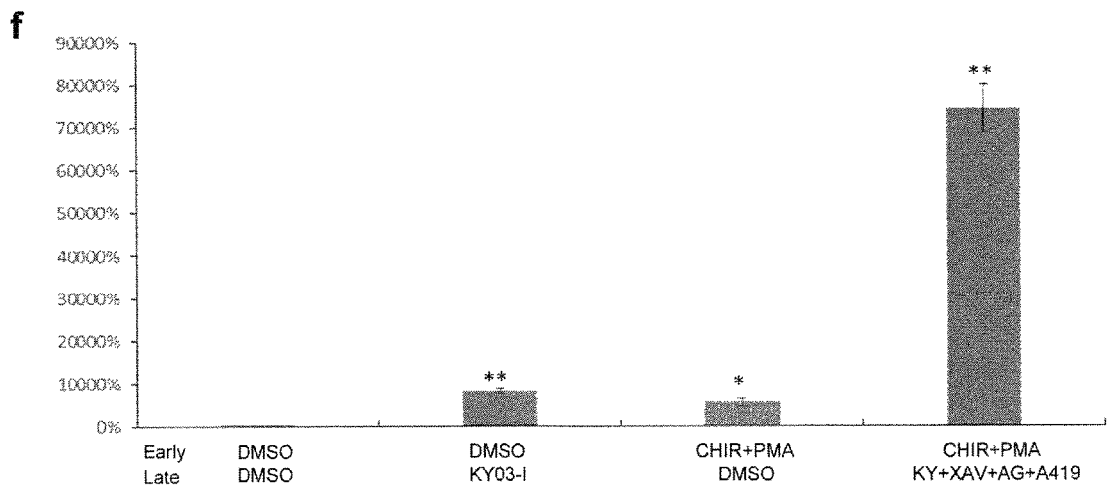
FIG. 1f: The cardiac differentiation of monkey ES cells with the six compounds of CHIR99021, PMA, KY03-I, XAV939, AG1478 and A419259. CHIR: CHIR99021, KY: KY03-I, XAV: XAV939, AG: AG1478, A419: A419259. *P<0.05 (t-test). **P<0.01 (t-test). Every value was obtained with n=3.

The monkey ES cell line (CMK6.4) transfected with GFP gene was cultured in media to which the six compounds CHIR99021, PMA, KY03-I, XAV939, AG1478 and A419259 were added. In particular, 1 µM CHIR99021 and 0.1 µM PMA were added to the culture media for early phase of differentiation (day 0 to day 2), and 3 µM KY03-I, 1 µM XAV939, 10 µM AG1478 and 0.3 µM A419259 were added to the culture media for late phase of differentiation (day 3 to day 7). The GFP fluorometry on the cultured cells suggested that the cardiac differentiation was highly stimulated by the use of the six compounds in combination (approximately 750 times higher compared with cells from culture with DMSO in place of the test compounds) (FIG. 1f).

Protein-Free Cardiac Differentiation of Human Pluripotent Stem Cells

Figure 2A:
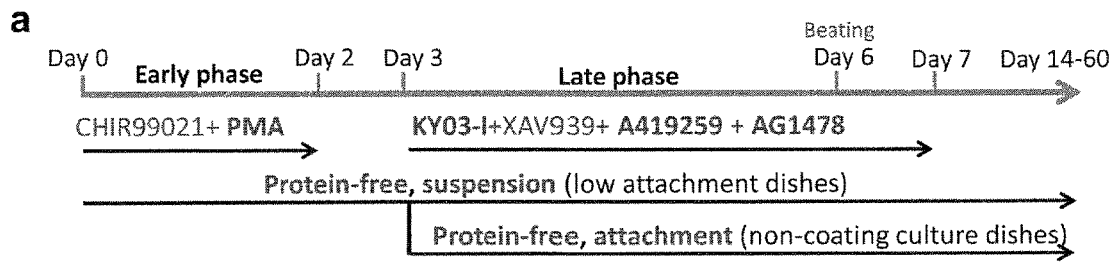
FIG. 2a: A protocol for inducing protein-free cardiac differentiation (PFCD) with the six compounds.

A protocol for testing the six compounds for the ability of inducing protein-free cardiac differentiation (PFCD) is illustrated in FIG. 2a. In particular, floating colonies of pluripotent stem cells (prepared by the procedure as described in Minami, I. et al., Cell reports 2, 1448-1460 (2012) or WO 2013/111875; the references are incorporated herein by reference) were suspension cultured in a PFCD medium (Table 2), to which a GSK3β inhibitor (2 µM CHIR99021) and a PKC activator (either 0.3 µM PMA or 3 µM prostratin) were added in the early phase (day 0 to day 2) of cardiac differentiation. The medium was then replaced with a PFCD medium with no test compound added, and cultured for one day (day 2 to day 3). In the following late phase of differentiation (day 3 to day 7), the cells were suspension cultured or adhesion cultured in the PFCD medium, to which Wnt signaling inhibitors (3 µM KY03-I and 1 µM XAV939), an EGFR inhibitor (10 µM AG1478) and an Src inhibitor (0.3 µM A419259) were added. For the suspension culture, low attachment plates (Waco 641-07391 or Corning YO-01835-24) were used. For the adhesion culture, usual plates (Falcon 353004) were used without coating so that the protein-free condition is ensured. Beating colonies generally began to appear on day 7 to day 9. The differentiated cardiomyocytes could be maintained for one to two months in the PFCD medium under suspension or adhesion culture condition.

Shown in Table 2 below is a list of formulations of culture media for PFCD and their purchase prices. These media comprise low-molecule synthetic compounds and amino acids, and are free from any protein or peptide. They are available at such a low cost as at most 1,200 yen per 500 ml.

TABLE 2

| Formulation | Cat. No. | Amount | Cost (Yen) |
| --- | --- | --- | --- |
| IMDM | Sigma I3390 | 242 ml | 420 |
| DMEM | Sigma D5796 | 242 ml | 310 |
| MEM non-essential amino acid | Sigma M7145 | 5 ml | 130 |
| Penicillin-Streptomycin | GIBCO 15140 | 5 ml | 200 |
| 0.2M L-glutamine | Sigma G7513 | 5 ml | 94 |
| 1M L-carnitine | Sigma C0283 | 100 µl | 20 |
| Ascorbic acid | Sigma A5960 | 50 mg | 10 |
| 0.5M creatine | Sigma C0780 | 1 ml | 12 |
| Total | | 500 ml | 1196 (≈10$) |

Figure 2B:
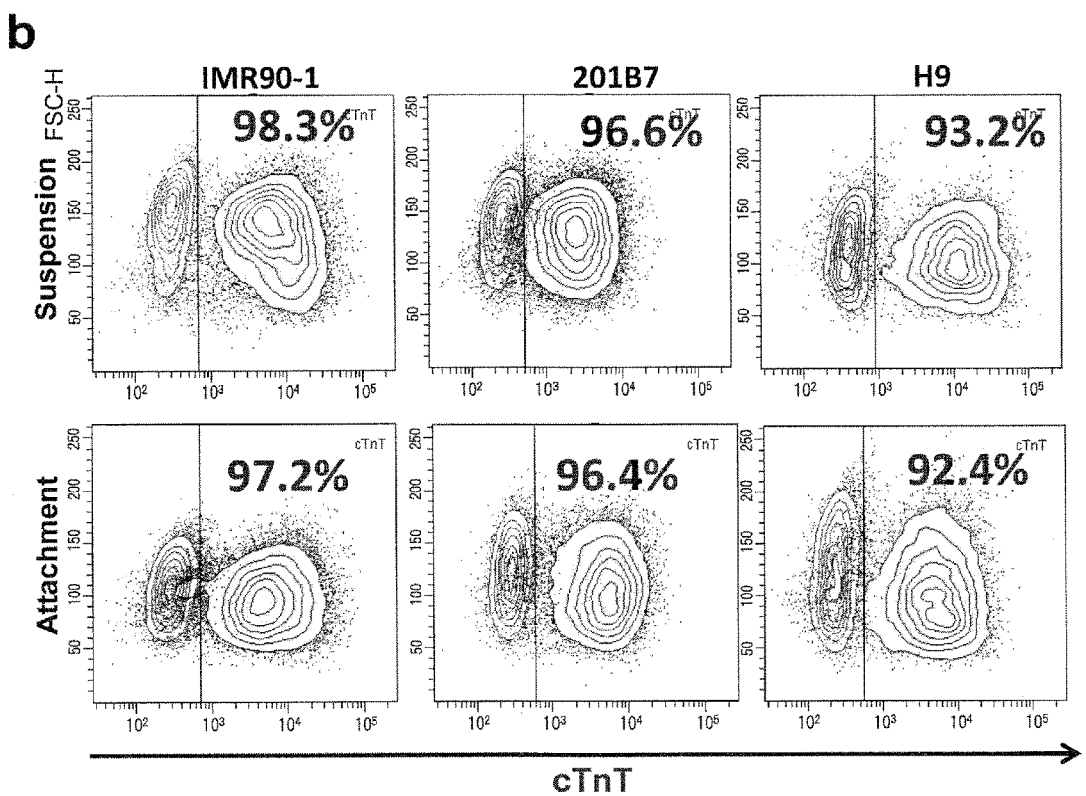
FIG. 2b: Dot plots from flow cytometry showing the percentages of cardiomyocytes in the cell populations from suspension culture or adhesion culture under PFCD condition of a human pluripotent stem cell line obtained from culture on MEF feeder. An antibody to a cardiac marker cTnT was used for staining.
Figure 2C:
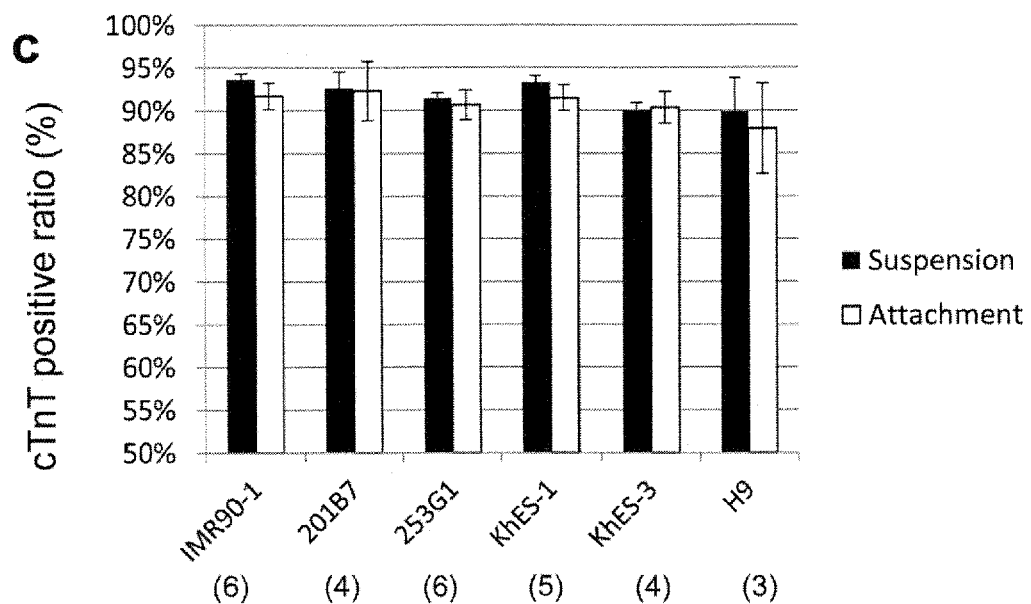
FIG. 2c: A graph summarizing the data of FIG. 2b. The numbers in parentheses are the numbers of n.

The cells from suspension or adhesion culture under PFCD condition of human pluripotent stem cells, which are from culture on MEF feeder, were analyzed for the percentage of cardiomyocytes therein by flow cytometry (FIG. 2b). An antibody to a cardiac marker cTnT was used for staining. A part of the cultured cells were not treated with the primary antibody to serve as a negative control. Thirty thousand cells from each sample were loaded to a flow cytometer FACSCantoII. It was determined that cardiomyocytes comprised around 90% in average of the cell population from culture of any of the human iPS cell lines IMR90-1, 201B7 and 253G1 and human ES cell lines KhES-1, KhES-3 and H9 (n=3 or more) (FIG. 2c).

Figure 2D:
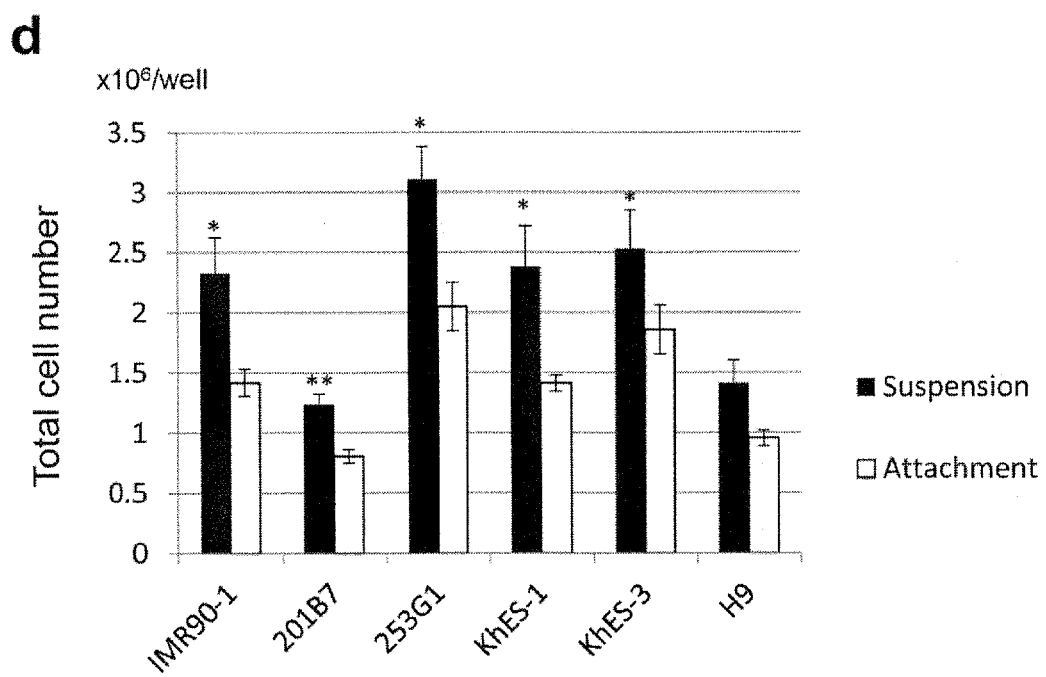
FIG. 2d: Counts of cardiomyocytes differentiated from a human pluripotent stem cell line from culture on MEF feeder; per $2 \times 10^6$ of the undifferentiated cells. For inducing the differentiation, the undifferentiated cells were suspension cultured or adhesion cultured under PFCD condition. *P<0.05 (t-test). **P<0.01 (t-test). Every value was obtained with n=3.

The differentiated cardiomyocytes was counted in the cell population from suspension or adhesion culture under PFCD condition of the pluripotent stem cell lines. The counts of differentiated cells per $2 \times 10^6$ undifferentiated cells are shown in the graph of FIG. 2d. The differentiation was more induced by suspension culture than adhesion culture in most of the stem cell lines. The cell count, as well as the flow cytometry, was taken on day 14.

Figure 3A:
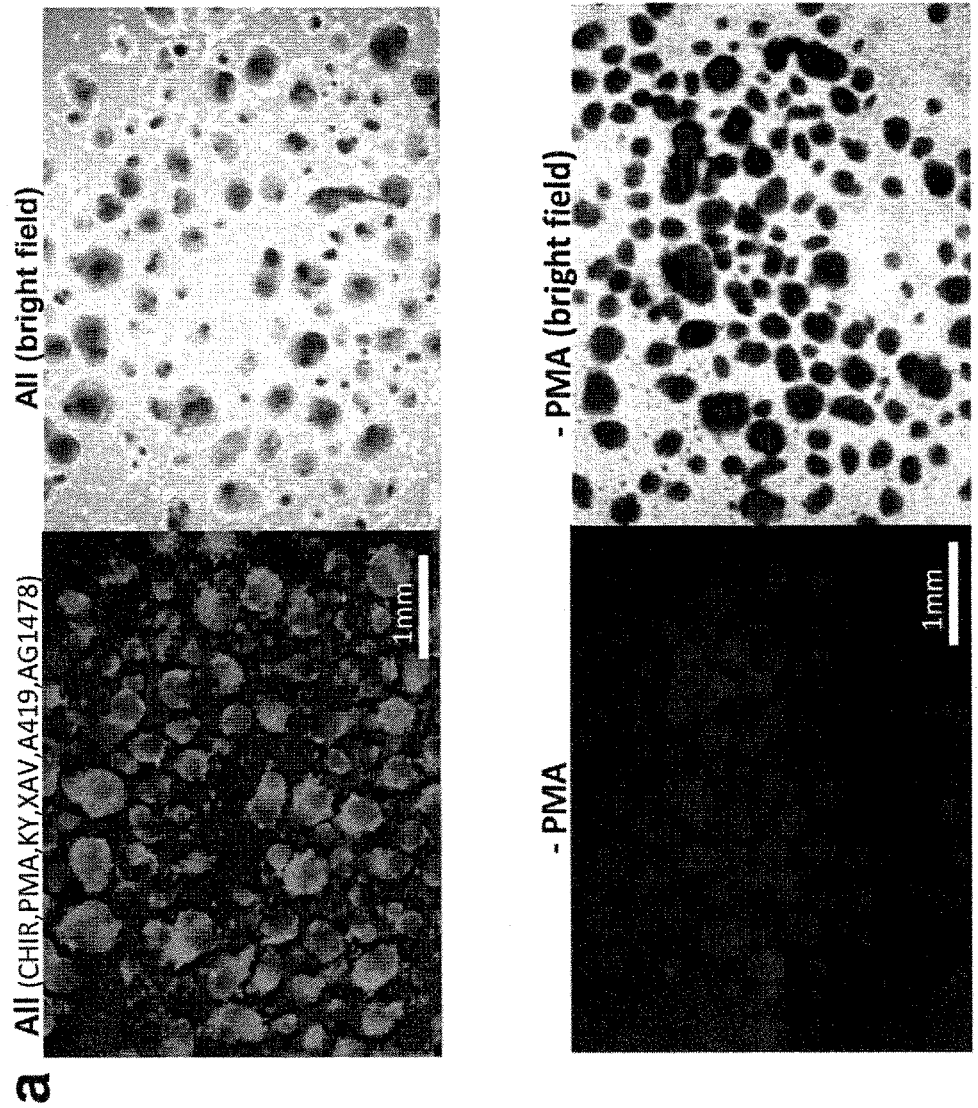
FIG. 3a: GFP Fluorescence micrographs of the cells from suspension culture under PFCD condition of a monkey ES cell line transfected with an α-MHC promoter-driven GFP gene (FIG. 2a) in the presence of PMA (that is, all the six compounds were added; the left-hand micrographs) or in the absence of PMA (that is, only the other five compounds were added; the right-hand micrographs).

Contribution of WNT Signaling Activators, PKC Activator, WNT Signaling Inhibitor, Src Inhibitor and EGFR Inhibitor to Cardiac Differentiation Under Protein-Free Condition A monkey ES cell line transfected with an α-MHC promoter-driven GFP gene was suspension cultured under PFCD condition in culture media with PMA (with all the six compounds added) or without PMA (with the five compounds other than PMA added) (FIG. 2a). GFP Fluorescence micrographs of the cultured cells are shown in FIG. 3a. The cells from the culture with PMA are shown in the left-hand micrographs, and the cells from the culture without PMA are shown in the right-hand micrographs. As shown, the colonies from the culture with PMA were mostly GFP-positive. In contrast, only weak fluorescence was detected in the cells from the culture without PMA.

Figure 3B:
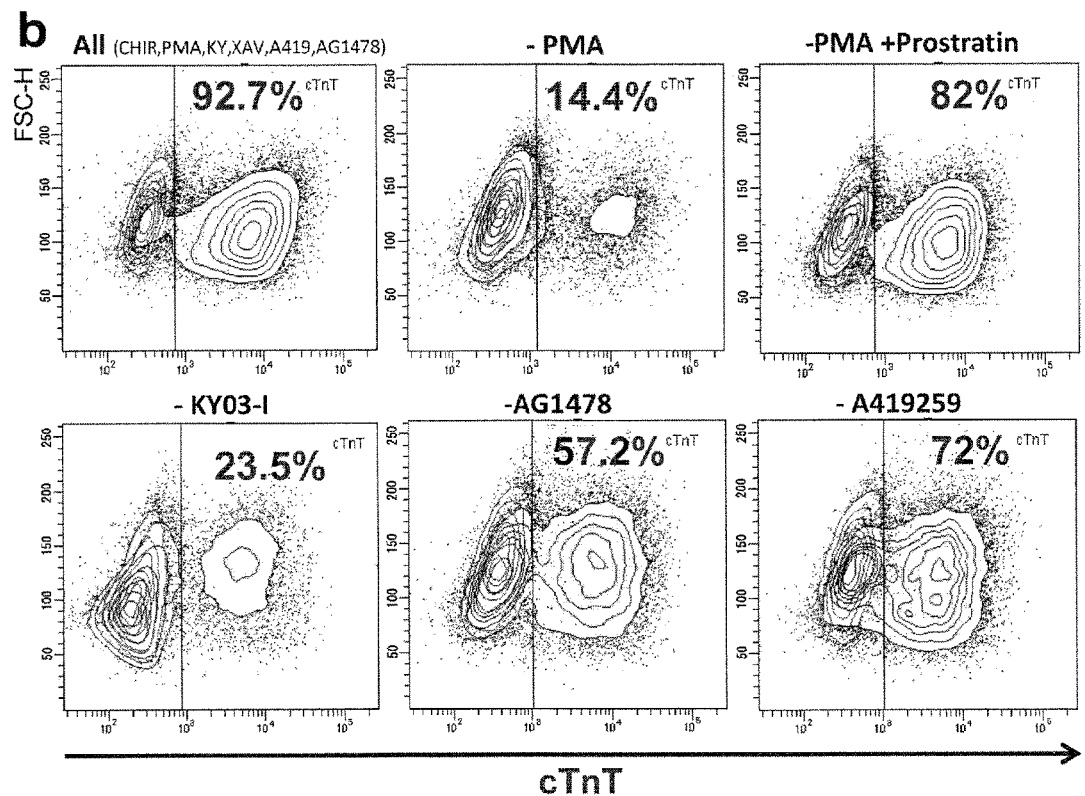
FIG. 3b: Dot plots from flow cytometry showing the percentages of cardiomyocytes in the cell populations from culture under PFCD conditions with different combinations of five compounds from the six compounds of CHIR99021, PMA, KY03-I, XAV939, AG1478 and A419259. An antibody to a cardiac marker cTnT was used for staining.

To determine the contribution of each of the six compounds (CHIR99021, PMA, KY03-I, XAV939, AG1478, and A419259) to PFCD under suspension culture condition, IMR90-1 (from culture on MEF feeder) was cultured in media to which different combinations of five of the compounds were added. Cells from the culture were analyzed by flow cytometry using a cTnT antibody for staining. A part of the cells from culture were not treated with the primary antibody to serve as a negative control. Thirty thousand cells from each sample were loaded to a flow cytometer FACSCantoII. It was found that the percentage of cTnT positive cells in the cells from culture was reduced when any one of the compounds was omitted from the culture (FIGS. 3b and 3c).

Figure 3C:
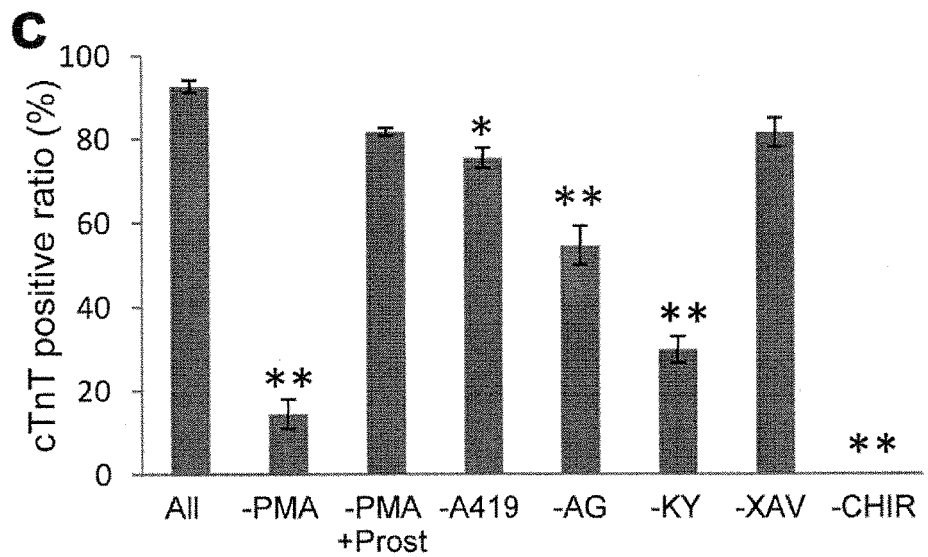
FIG. 3c: A graph summarizing the data of FIG. 3b. *P<0.05 (t-test). **P<0.01 (t-test). Every value was obtained with n=3.
Figure 3D:
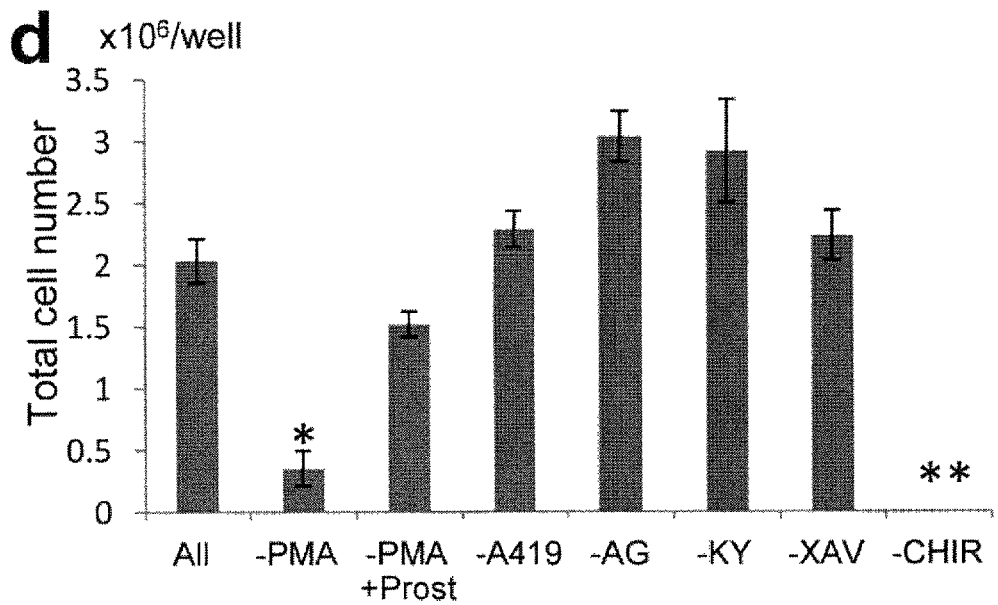
FIG. 3d: Counts of cardiomyocytes from culture under PFCD condition corresponding to the cells of FIG. 3c. *P<0.05 (t-test). **P<0.01 (t-test). Every value was obtained with n=3.

The differentiated cardiomyocytes was counted in a cultured cell population corresponding to that of FIG. 3c. It was found that the omission of CHIR99021 or PMA resulted in the significant reduction in the cardiomyocyte count. The cell count, as well as the flow cytometry, was taken on day 14.

Figure 3E:
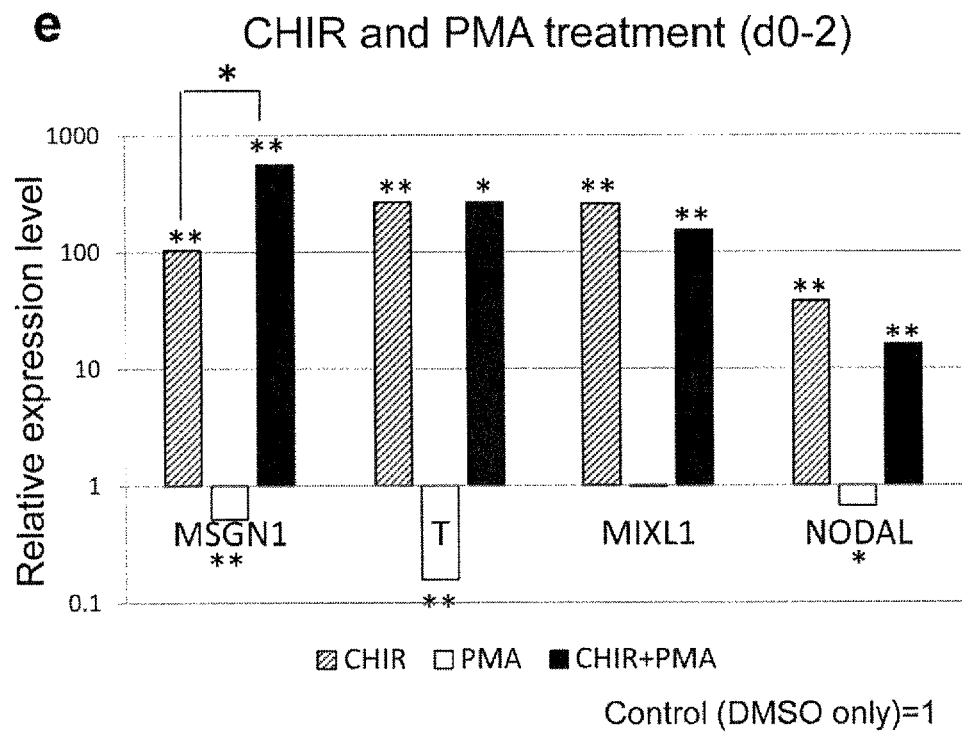
FIG. 3e: Expression of mesoderm-related genes (MSGN1, T, MIXL1 and NODAL) in the cells from culture under PFCD conditions with CHIR99021 and/or PMA added in the early phase of cardiac differentiation (day 0 to day 2). The expression levels are expressed relative to the expression level in control cells (assigned to one). The control cells were similarly cultured, but with DMSO in place of CHIR99021 and PMA. *P<0.05 (t-test). **P<0.01 (t-test). Every value was obtained with n=3.

A human iPS cell line (IMR90-1 cultured on MEF feeder) was cultured in PFCD culture media, to which 2 µM CHIR99021 or 0.3 µM PMA or the both (CHIR99021+PMA) were added for early phase of cardiac differentiation (day 0 to day 2). On day 2, mRNA was extracted the cultured cells and analyzed by quantitative PCR for the expression of mesoderm-related genes (MSGN1, T, MIXL1 and NODAL) (FIG. 3e). As a control, cells were cultured similarly, but with DMSO in place of the test compounds. The gene expression level in the control cells was assigned to one. It was found that the addition of CHIR99021 significantly increased the expression of the mesoderm-related genes. In contrast, the expression of the genes was reduced when PMA was added to the culture. However, the reduction in gene expression by PMA was counteracted and reversed when CHIR99021 was added in combination with PMA (in accordance with the optimal PFCD condition). In fact, the MSGN1 expression level in the cells cultured with both CHIR99021 and PMA was about six times as much as that in the cells cultured with CHIR99021 alone. The results suggest that the increase in the MSGN1 expression by the combination of CHIR99021 and PMA may be a primary factor contributing to the efficient PFCD.

Figure 3F:
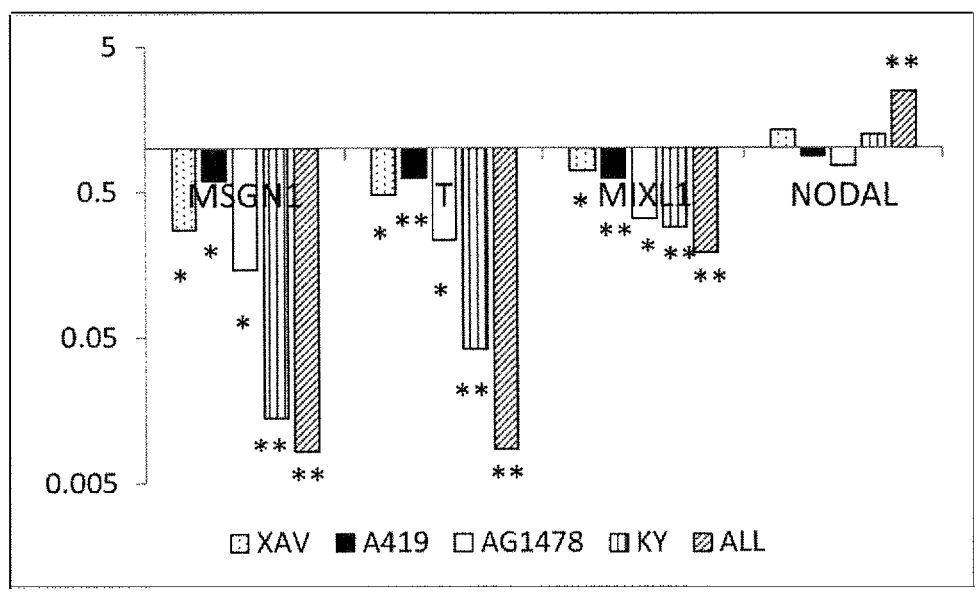
FIG. 3f: Expression of mesoderm-related genes (MSGN1, T, MIXL1 and NODAL) in the cells from culture under PFCD condition with XAV939, A419259, AG1478 and/or KY03-I added in the late phase of cardiac differentiation (day 3 to day 4). *P<0.05 (t-test). **P<0.01 (t-test). Every value was obtained with n=3.

A human iPS cell line (IMR90-1 from culture on MEF feeder) was cultured in PFCD media with one of 1 µM XAV939, 0.3 µM A419259, 10 µM AG1478 or 3 µM KY03-I, or all of them (XAV939+A419259+AG1478+KY03-I) in late phase of cardiac differentiation (day 3 to day 4). On day 4, mRNA was extracted from the cultured cells and analyzed by quantitative PCR for the expression of mesoderm-related genes (MSGN1, T, MIXL1 and NODAL) (FIG. 3f). It was found that each of the four compounds reduced the expression of MSGN1, T and MIXL1; the reduction was more significant when the four compounds were used in combination. The expression level of NODAL was not significantly different among the cells from culture with each of the four compounds, but was significantly increased when the four compounds were used in combination. The results suggest that the four compounds would synergistically affect the expression of the mesoderm-related genes in late phase of cardiac differentiation, and contribute to efficient PFCD. This is notable, because the expression of mesoderm-related genes is generally reduced in late phase of cardiac differentiation compared with early phase of differentiation.

Figure 4A:
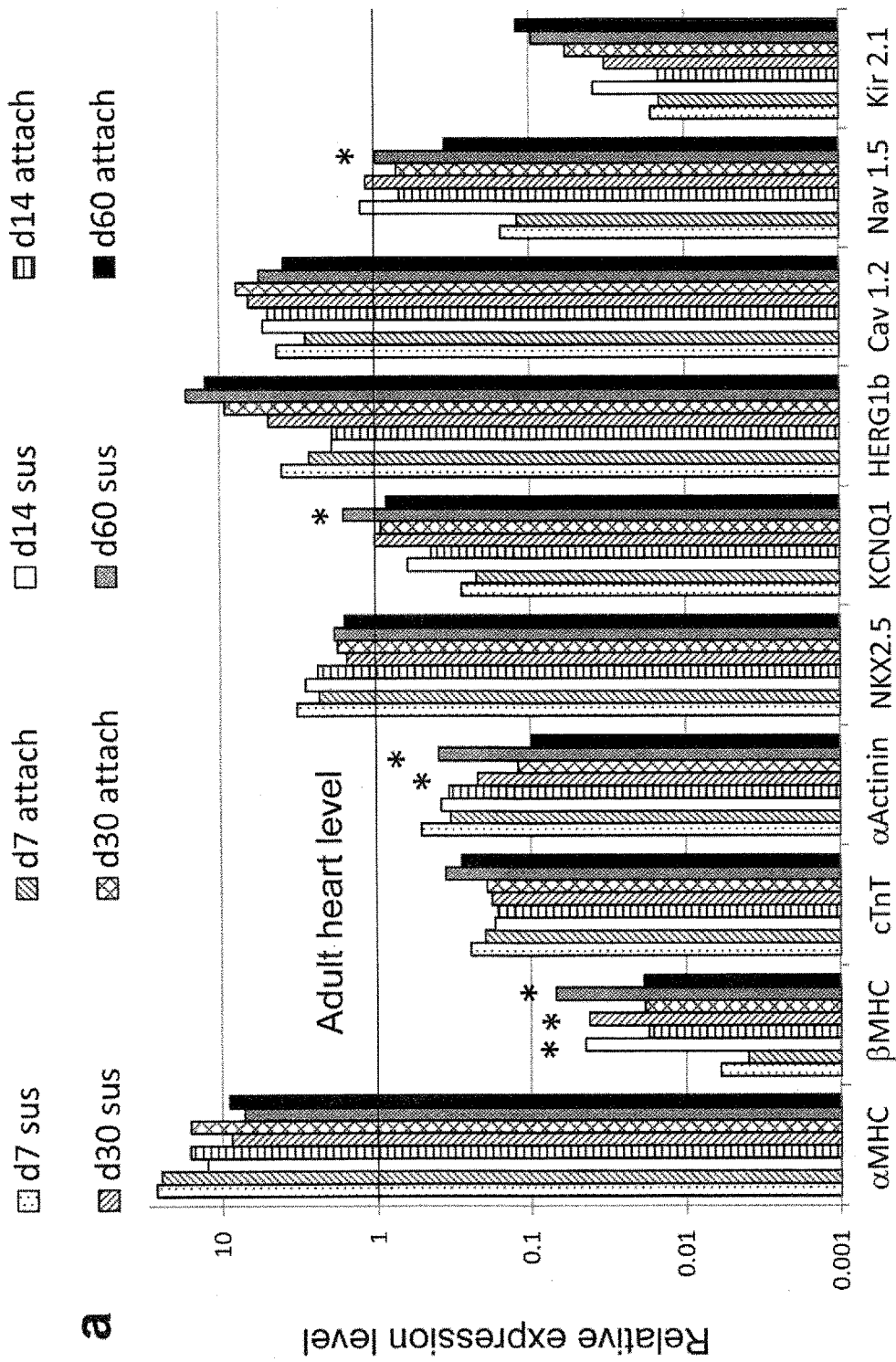
FIG. 4a: Gene expression determined by quantitative PCR in the cells from culture under PFCD condition. *P<0.05 (t-test). Every value was obtained with n=3.

Expression of Cardiac Markers and Channels in PFCD Cardiomyocytes from Human Pluripotent Stem Cells Cells from culture under PFCD condition were analyzed for expression of cardiac marker and channel genes by quantitative PCR. In particular, IMR90-1 (from culture on MEF feeder) was suspension cultured or adhesion cultured under PFCD condition. Total mRNA was extracted from cells harvested from the culture on day 7, day 14, day 30 and day 60, and subjected to quantitative PCR to determine the expression of genes of cardiac markers ($\alpha$MHC, $\mu$MHC, cTnT, $\alpha$Actinin and NKX2.5) and cardiac channels (KCNQ1, HERG1b, Nav1.5, Cav1.2 and Kir2.1). As a control, gene expression level in mRNA from human adult heart tissue was assigned to one. The expression of the genes was observed in every sample of cells from culture under PFCD condition (FIG. 4a). In these cells, the expression levels of $\beta$MHC (a marker of mature human cardiomyocytes) and Kir2.1 (involved in the generation of resting membrane potential) were only around one-tenth of those in the control, which suggests that the PFCD cardiomyocytes were not matured as fully as the adult heart cells. However, since the gene expression tended to increase over the course of culturing, maturation of the PFCD cardiomyocytes was considered to progress over time. The expression levels of $\beta$MHC, $\alpha$Actinin and KCNQ1 were higher in the cells from suspension culture than the cells from adhesion culture, which suggests that suspension culture condition would be more suitable for the maturation of PFCD cardiomyocytes than adhesion culture condition.

Figure 4B:
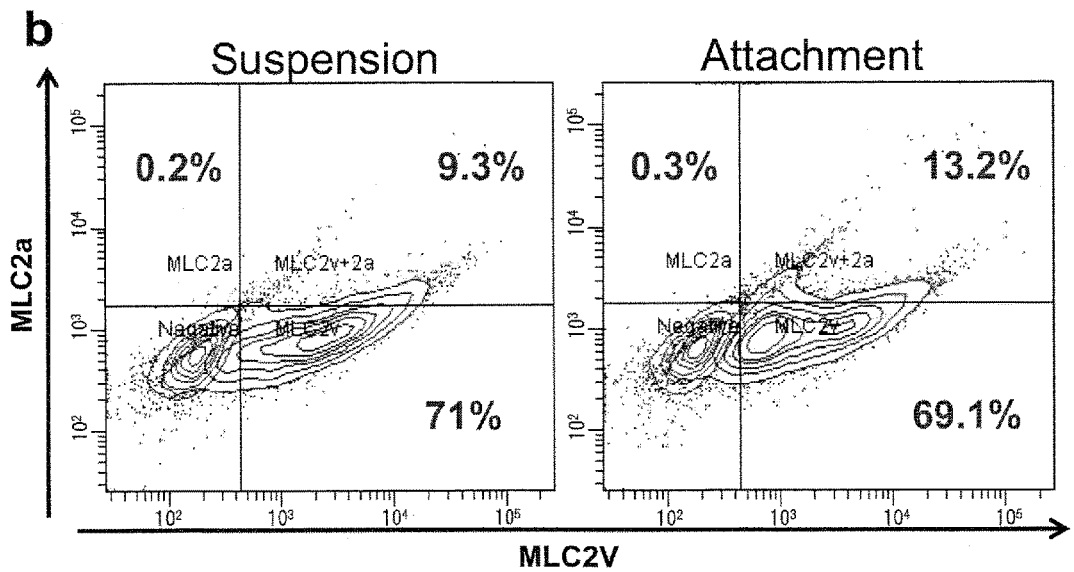
FIG. 4b: Differentiated cells having a marker of ventricular muscle MLC2v and a marker of atrial muscle MLC2a detected by flow cytometry with immunostaining.
Figure 4C:
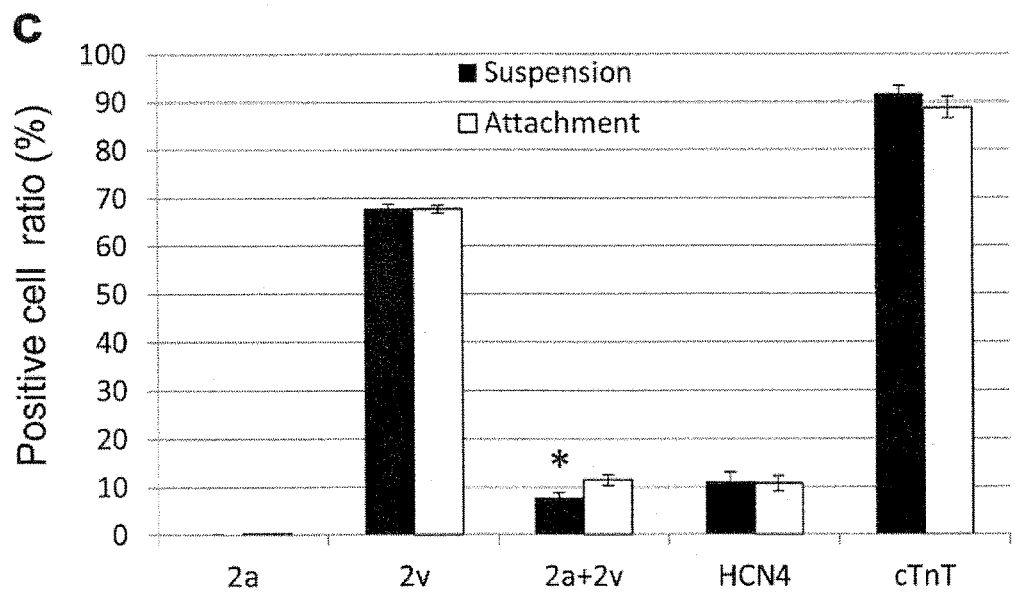
FIG. 4c: A graph summarizing dot plot data from flow cytometry with immunostaining for differentiated cells having a marker of ventricular muscle MLC2v, a marker of atrial muscle MLC2a, and a cardiac marker cTnT. *P<0.05 (t-test). Every value was obtained with n=4.

For comparing PFCD effect of suspension culture with PFCD effect of adhesion culture, IMR90-1 (from culture on MEF feeder) was suspension or adhesion cultured under PFCD condition. Cells were harvested on day 30 and analyzed by flow cytometry with immunostaining for the expression of MLC2v (a marker of ventricular muscle), MLC2a (a marker of atrial muscle), HCN4 (a marker of pacemaker), and cTnT (a marker of cardiac cell). The plots based on double staining for MLC2v and MLC2a (FIG. 4b) revealed that suspension culture and adhesion culture were almost equivalent in terms of the induction of differentiation to MLC2v-single-positive cells (approximately 70%) and MLC2a-single-positive cells (approximately 0.2% to 0.3%), but suspension culture was significantly less effective than adhesion culture in the induction of differentiation to MLC2v/MLC2a-double-positive cells (approximately 9% by suspension culture, and approximately 13% by adhesion culture) (FIGS. 4b and 4c). The MLC2v/MLC2a-double-positive cells are known as immature ventricular muscle cells. Therefore, suspension culture is considered to be more useful for PFCD to give fewer immature ventricular muscle cells than adhesion culture. Around 10% of the cultured cell population were HCN4-positive (pacemaker) and around 90% were cTnT-positive (FIG. 4c). A part of the cultured cells were not treated with the primary antibodies to serve as a negative control. For the analysis, thirty thousand cells from each sample were loaded to a flow cytometer FACSCantoII.

Figure 4D:
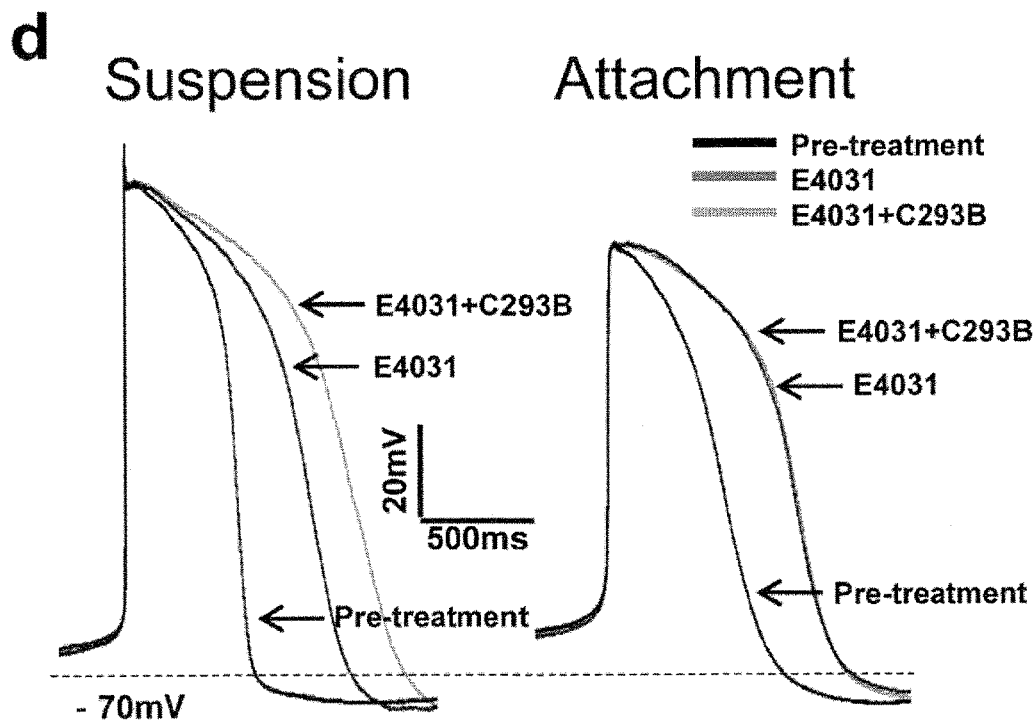
FIG. 4d: Electrophysiology of cells from adhesion culture or suspension culture under PFCD conditions, determined by a whole-cell patch claim technique.
Figure 4E:
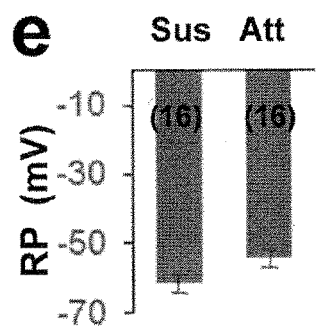
FIG. 4e: Resting Potential (RP) in the cells from adhesion culture or suspension culture under PFCD condition.
Figure 4F:
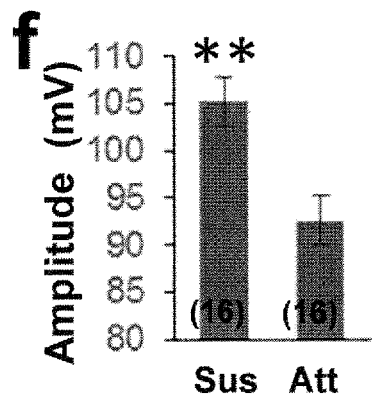
FIG. 4f: Action potential amplitude (Amplitude) in the cells from adhesion culture or suspension culture under PFCD condition. *P<0.01 (t-test).
Figure 4G:
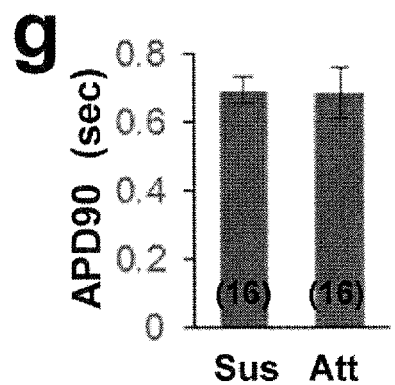
FIG. 4g: Action potential duration (APD90) in the cells from adhesion culture or suspension culture under PFCD condition.
Figure 4H:
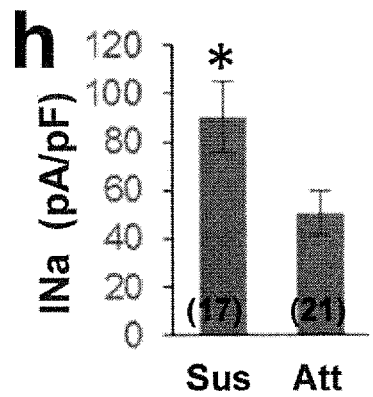
FIG. 4h: Voltage-gated Na channel current (INa) in the cells from adhesion culture or suspension culture under PFCD condition. *P<0.05 (t-test).
Figure 4I:
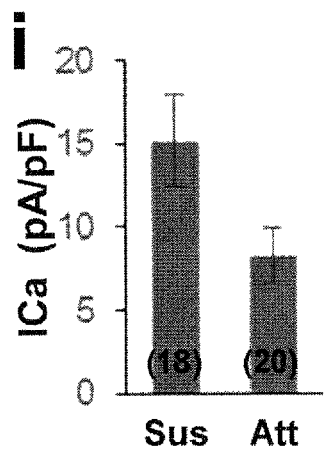
FIG. 4i: Voltage-gated Ca channel current (ICa) in the cells from adhesion culture or suspension culture under PFCD condition.
Figure 4J:
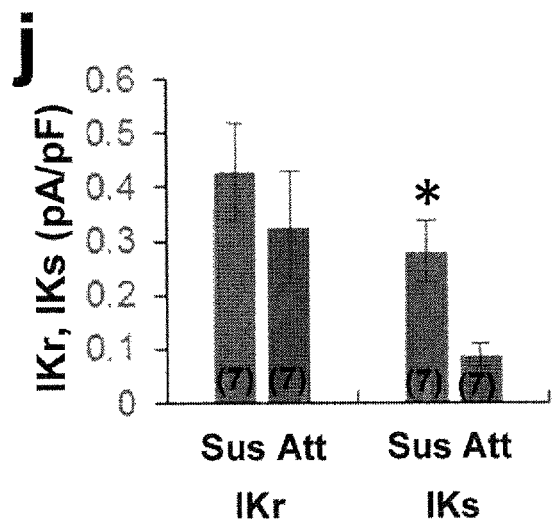
FIG. 4j: HERG Channel current (IKr) and KCQN1 channel current (IKs) in the cells from adhesion culture or suspension culture under PFCD condition. *P<0.05 (t-test).
Figure 4K:
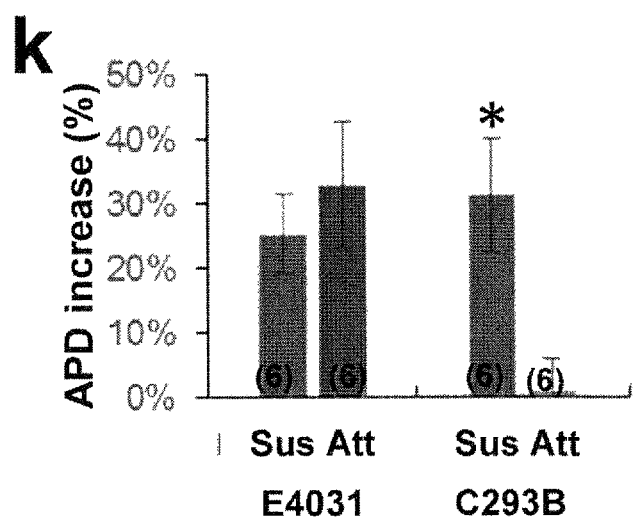
FIG. 4k: Increase in APD90 in the cells from adhesion culture or suspension culture under PFCD condition, compared with control cells. C293B: Chromanol293B. *P<0.05 (t-test).

Comparison was made between cells from suspension culture and cells from adhesion culture in terms of electrophysiology of cells by using a whole-cell patch clamp technique. For this purpose, IMR90-1 (from culture on MEF feeder) was suspension or adhesion cultured under PFDC condition. Cells were harvested on day 30 for the analysis. In action potential waveforms in the cells from suspension culture and the cells from adhesion culture, there was no significant difference between the cell populations in terms of RP (resting potential; around −60 mV) (FIGS. 4d and 4e) and APD90 (action potential duration; about 0.7 sec) (FIGS. 4d and 4g). However, Amplitude (action potential amplitude) in the cells from suspension culture was about 105 mV which was significantly higher than about 90 mV in the cells from adhesion culture (FIGS. 4d and 4f). INa (Voltage-gated Na channel current) was significantly higher in the cells from suspension culture than the cells from adhesion culture (FIG. 4h). ICa (Voltage-gated Ca channel current) was also higher in the cells from suspension culture than the cells from adhesion culture, but the difference was not significant (FIG. 4i). IKr (HERG channel current) was not significantly different between the two cell populations. IKs (KCQN1 channel current) was higher in the cells from suspension culture than the cells from adhesion culture (FIG. 4j). The effect of E4031 (a HERG channel inhibitor) on the increase in APD90 (APD increase 6) was not significantly different between suspension culture and adhesion culture. On the other hand, the increase in APD90 in cells cultured in the presence of a KCNQ1 channel inhibitor Chromanol293B (C2938) was significantly higher in the cells from suspension culture than the cells from adhesion culture (FIG. 4k).

Amplitude and INa, which were higher in the cells from suspension culture, were thought to depend on the expression of voltage-gated Na channel. Actually, the expression of Nav1.5 channel (a subtype of voltage-gated Na channel) tended to be higher in the cells from suspension culture (FIG. 4a). IKs And APD increase (C293B) were also higher in the cells from suspension culture. IKs Is KCQN1 channel current, and APD increase (C293) would be a result of the KCNQ1 inhibition by C293B. Actually, the expression of KCNQ1 was higher in the cells from suspension culture (FIG. 4a). Mature human adult ventricular muscle cells have an RP of from −80 to −90 mV. In contrast, the PFCD ventricular muscle cells were immature having a shallower RP of around −60 mV, in accordance with the relatively low expression of Kir2.1 which is involved in the generation of RP (approximately one-tenth of the expression in the mature human ventricular tissue) (FIG. 4a). It was concluded that suspension culture would be more effective in the induction of cardiomyocyte maturation under PFCD condition than adhesion culture, although the cells from the culture are still not matured as fully as human adult cardiomyocytes as reflected in the shallower RP.

Sarcomere Structure in PFCD Cardiomyocytes

Figure 5A:
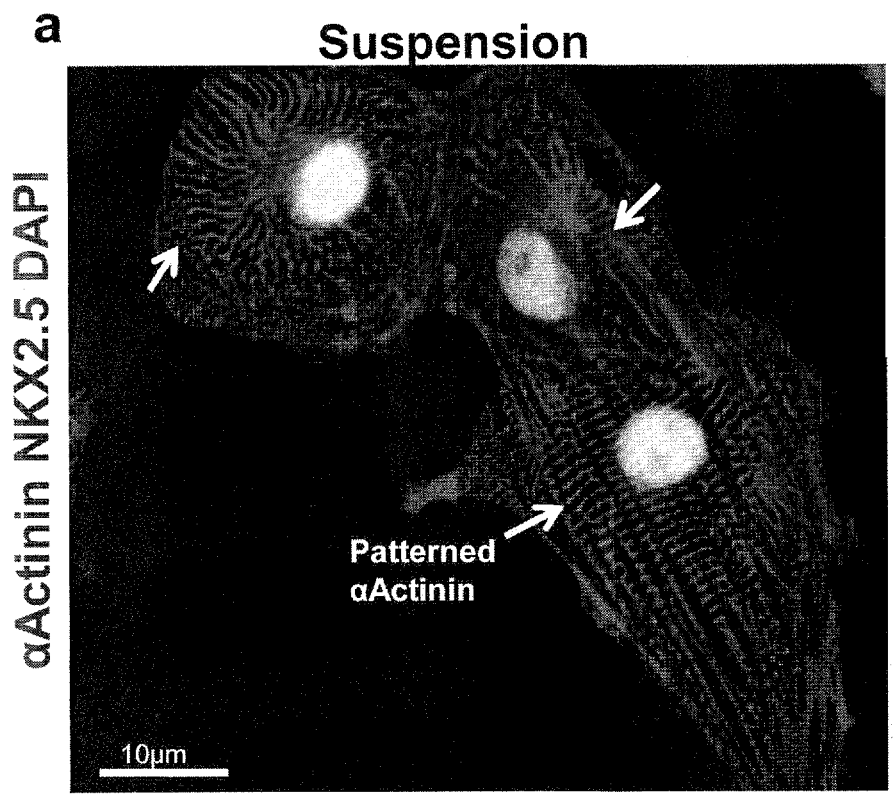
FIG. 5a: A micrograph of cells from suspension culture under PFCD condition, with immunostained αActinin and NKX2.
Figure 5B:
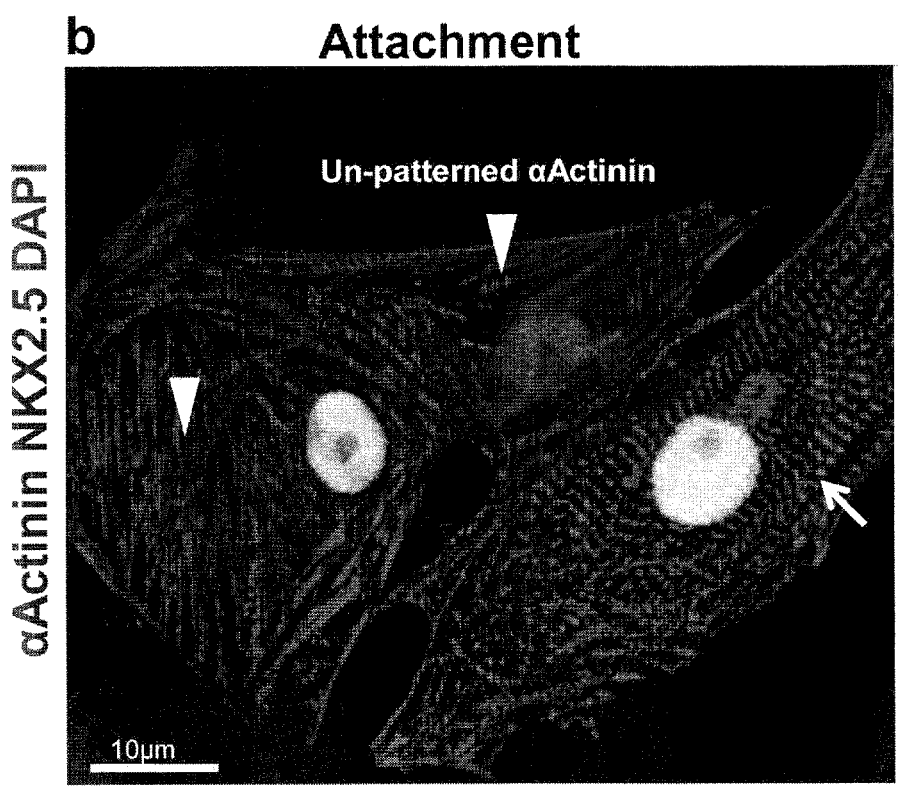
FIG. 5b: A micrograph of cells from adhesion culture under PFCD condition, with immunostained αActinin and NKX2.

Cells were harvested from suspension culture and adhesion culture under PFCD condition of IMR90-1 (from culture on MEF feeder) at day 30 and subjected to the immunostaining for αActinin (a Z disc marker of sarcomeres), and NKX2.5 (a transcription factor specific to cardiomyocyte), and the DAPI staining for nuclei. As shown in FIGS. 5a and 5b, two types of cardiomyocytes were observed; that is, the cardiomyocytes having a clear striped staining pattern of αActinin (patterned αActinin; shown by arrows), and the cardiomyocytes not having such clear pattern (un-patterned αActinin; shown by arrowheads). A larger number of the cells with patterned αActinin were observed in the cells from suspension culture than the cells from adhesion culture, in which the cells with un-patterned αActinin dominated.

Figure 5C:
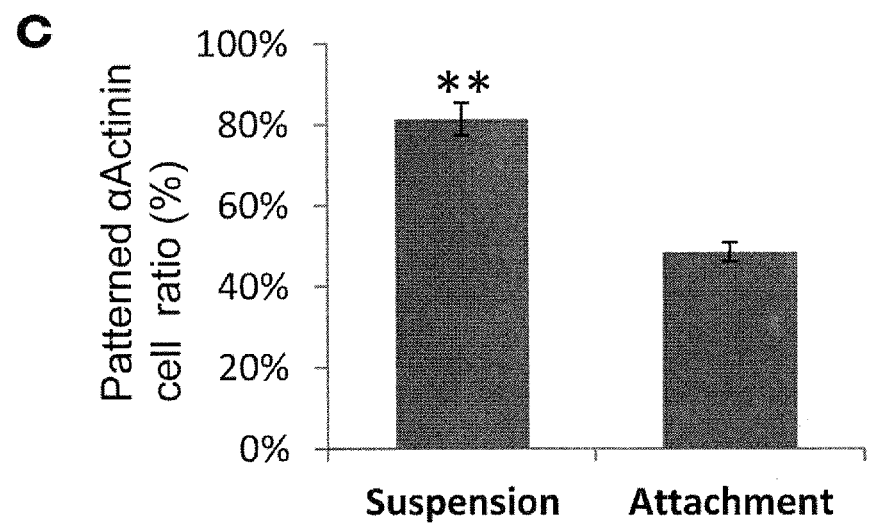
FIG. 5c: Percentages of cells having clear striped pattern of αActinin (patterned cells) in the cell populations from suspension culture or adhesion culture under PFCD condition. The determination was made in triplicate. Pattern of stained αActinin was evaluated in 30 to 50 cells each time in accordance with the definitions of cells shown in FIGS. 5a and 5b. **P<0.01 (t-test).

The percentage of the PFCD cardiomyocytes with pattered αActinin was determined in the cell population from suspension culture and the cell population from adhesion culture (FIG. 5c). The percentage of cells with pattered αActinin was around 80% in the cell population from suspension culture, and only about 50% in the cell population from adhesion culture.

Figure 5D:
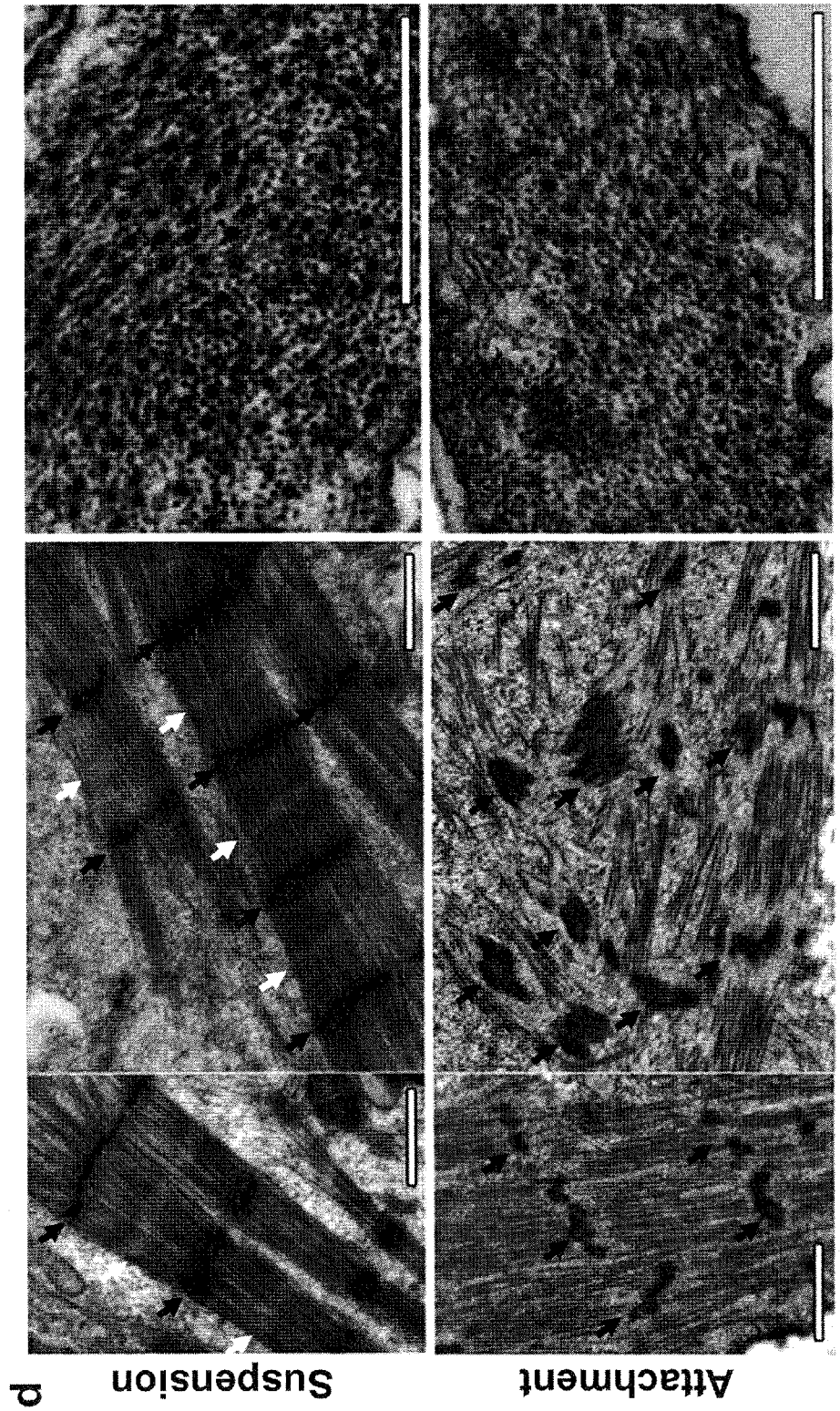
FIG. 5d: Electron micrographs of cells from adhesion culture under PFCD condition.

FIG. 5d shows electron micrographs of the PFCD cardiomyocyte with sarcomere structures. The Z discs (black arrows), the M bands (white arrows) and the myofilaments (in the right-hand panels) are seen more clearly and as more aligned structure in the cells from suspension culture (FIG. 5d). The structures confirmed with electron micrographs are consistent with the analytic data from the immunostaining of αActinin.

The formation of clear sarcomere structure is an indicator of the maturation of myocardial fibers. Therefore, the clearer sarcomere structure as confirmed in the PFCD cardiomyocytes from suspension culture suggests that suspension culture would be more effective for the maturation of myocardial fiber structure in the cells than adhesion culture. The maturation of sarcomere structure would be accompanied by the expression of αActinin, because the expression of αActinin was higher in the cells from suspension culture than the cells from adhesion culture.

Protein-Free Cardiac Differentiation of Human Pluripotent Stem Cells from Culture Under Feeder- and Xeno-Free Condition Human iPS cell lines (IMR90-1 and 253G1) were subcultured under a condition of feeder-free (adhesion on laminin fragments) (Miyazaki, T. et al. Laminin E8 fragments support efficient adhesion and expansion of dissociated human pluripotent stem cells. Nat Commun 3, 1236 (2012), which is incorporated herein by reference) and, at the same time, xeno-free (Essential8 medium, Chen, G. et al. Chemically defined conditions for human iPSC derivation and culture. Nat Methods 8, 424-429 (2011), which is incorporated herein by reference). The cells were then suspension cultured under PFCD condition. The percentage of cardiomyocytes was determined in the cell population from the suspension culture under PFCD condition (FIGS. 6a and 6b). Thirty thousand cells from each sample were loaded on a flow cytometer FACSCantoII with using an antibody to cTnT for staining. Cardiomyocytes constituted as high as above 85% of the cell population from culture. Thus, it was found that PFCD was efficiently induced on the undifferentiated iPS cell line prepared as described above from the feeder- and xeno-free culture. Although the feeder- and xeno-free culturing uses five proteins in the culture medium (Chen, G. et al, supra) and is not protein free, it is still the best mode of culturing at present for preparing undifferentiated pluripotent stem cells for use as a material for tissue engineering. Accordingly, iPS cells from feeder- and xeno-free culture may be differentiated under PFCD condition according to the present invention, and the cardiomyocytes thus obtained must be more suited for clinical use than cardiomyocytes from any conventional culture.

Figure 6:
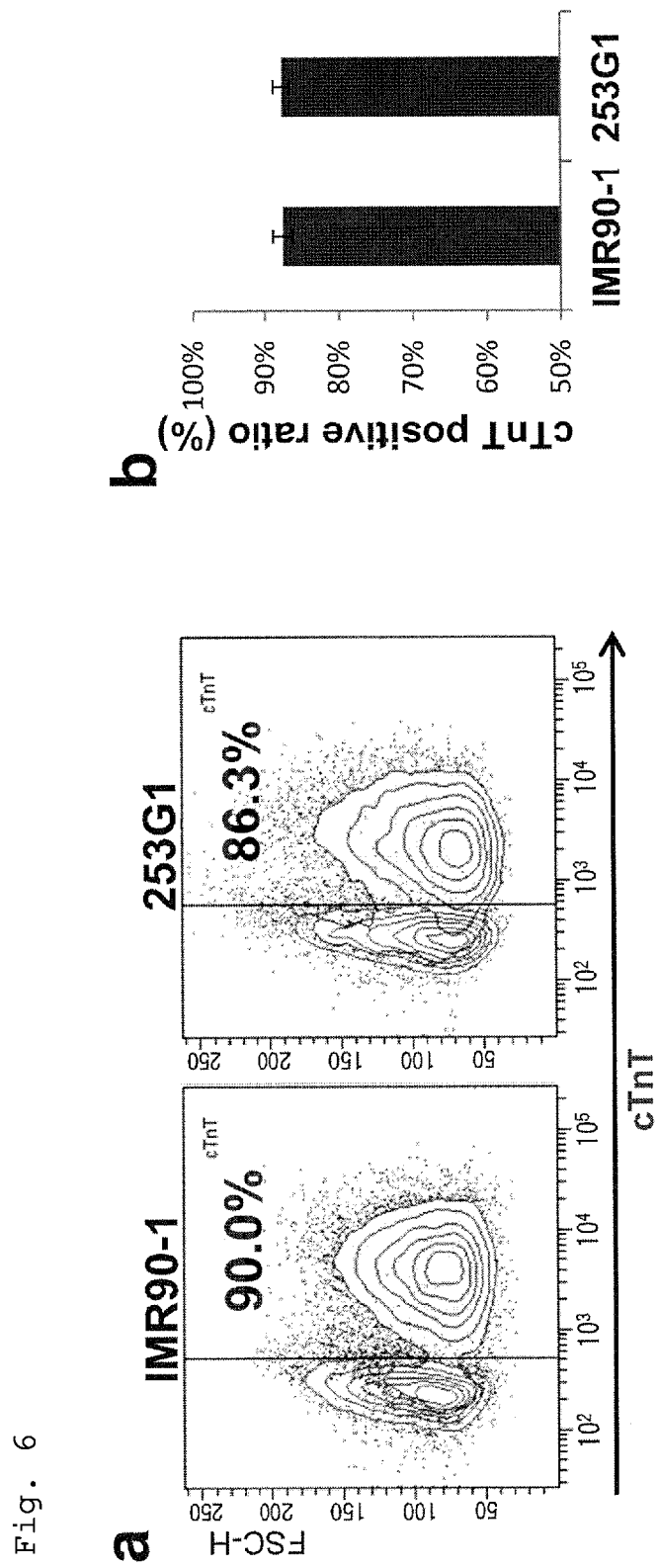
FIG. 6: Percentages of cardiomyocytes in the cell populations from suspension culture under PFCD condition of human iPS cell lines (IMR90-1 and 253G1) subcultured under feeder- and xeno-free condition, shown by dot plots from flow cytometry (a) and a graph (b) summarizing the dot data. An antibody to cTnT was used for staining. Cells not treated with the primary antibody served as negative control. Every value was obtained with n=3.
Figure 7:
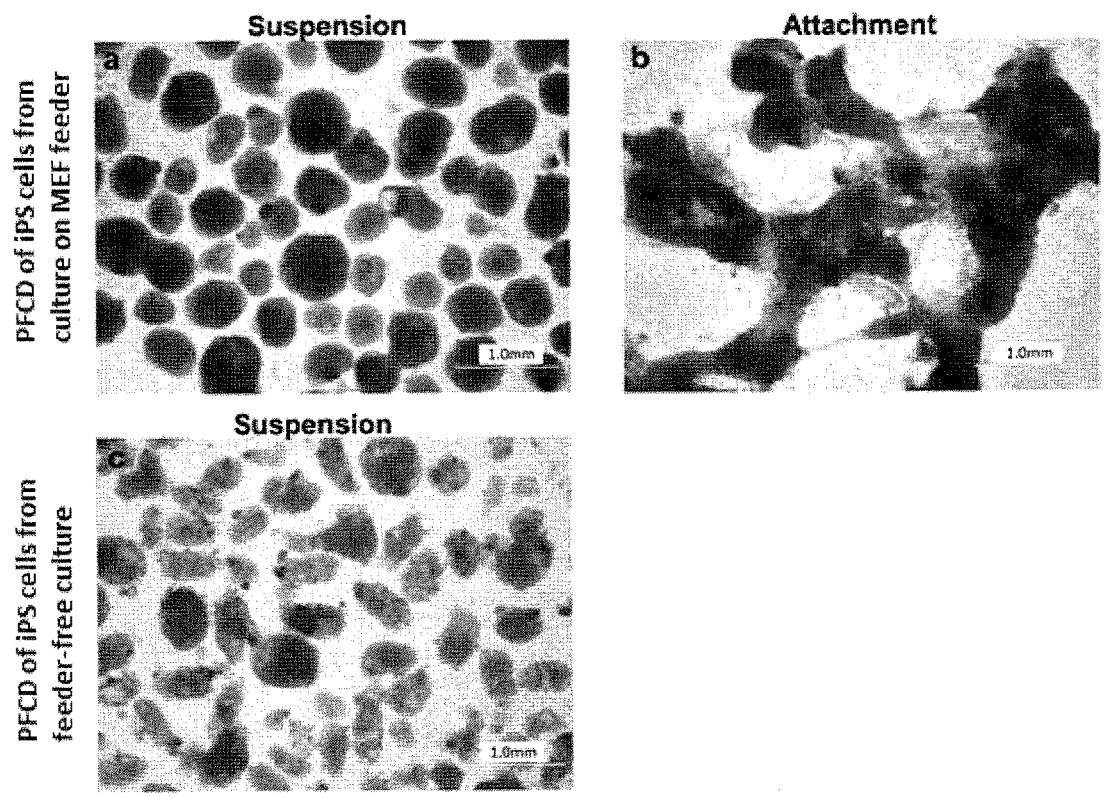
FIG. 7: Micrographs of cells from day 14 of suspension culture (a) or adhesion culture (b) under PFCD condition of a human iPS cell line (IMR90-1) from culture on MEF feeder, and a micrograph of cells from day 14 of suspension culture under PFCD condition of a human iPS cell line (253G1) from culture under feeder- and xeno-free condition (c) (corresponding to FIG. 6).

FIGS. 7a and 7b are micrographs of cardiomyocytes harvested on day 14 of suspension culture (FIG. 7a) and adhesion culture (FIG. 7b) under PFCD condition of the human iPS cell line IMR90-1 from culture on feeder. FIG. 7c is a micrograph of cardiomyocytes harvested on day 14 of suspension culture under PFCD condition of the human iPS cell line 253G1 from culture under feeder- and xeno-free condition (FIG. 6).

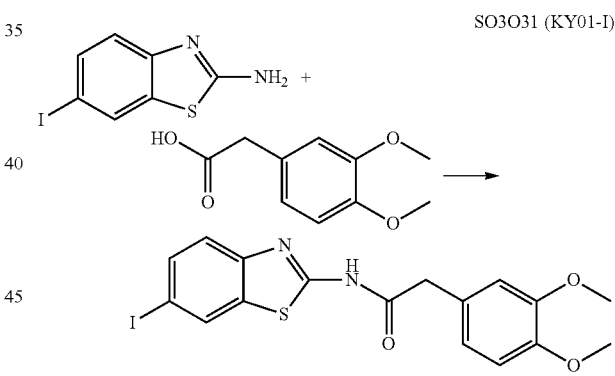

SO3O31 (KY01-I)

To a solution of 2-amino-6-iodobenzothiazole (200 mg, 0.73 mmol) and 3,4-dimethoxyphenylacetic acid (157 mg, 0.795 mmol) in N,N-dimethylformamide (3 ml), N,N-diisopropylethylamine (139 ul, 0.803 mmol) and O-(6-chlorobenzotriazol-1-yl)-N,N,N',N'-tetramethyluronium hexafluorophosphate (360 mg, 0.870 mmol) were added and stirred overnight at room temperature. Once the reaction was completed, the reaction was diluted with ethyl acetate, washed with saturated aqueous sodium hydrogen carbonate and saturated aqueous sodium chloride, and dried over anhydrous sodium sulfate. Then, the solvent was evaporated off under vacuum. The residue was recrystallized from ethanol to give 167 mg 2-(2-(3,4-dimethoxyphenyl)acetamido)-6-iodobenzothiazole (yield: 50%).

$^1$H NMR (DMSO-d$_6$): δ 12.61 (s, 1H), 8.37 (s, 1H), 7.73-7.69 (m, 1H), 7.54 (d, J=8.0 Hz, 1H), 6.97-6.84 (m, 3H), 3.75-3.72 (m, 8H).

MS (ESI) Found; 455 [M+H]$^+$

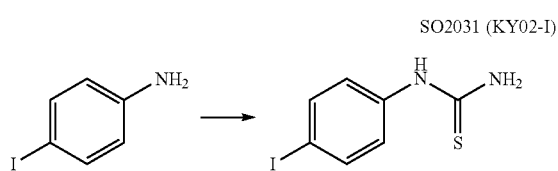 [SMILES: Nc1ccc(I)cc1 ; NC(=S)Nc1ccc(I)cc1]

To a solution of 4-iodoaniline (1.00 g, 4.57 mol) in dichloromethane (3 ml), thiocarbonyldiimidazole (976 mg, 5.47 mmol) was added and stirred for 1.5 hours at room temperature. Then, 25% aqueous ammonia (3 ml) was added, and the reaction was stirred overnight at room temperature. Once the reaction was completed, the solvent was evaporated off under vacuum, and the residue was filtrated to obtain 889 mg 1-(4-iodophenyl)thiourea (yield: 59%).

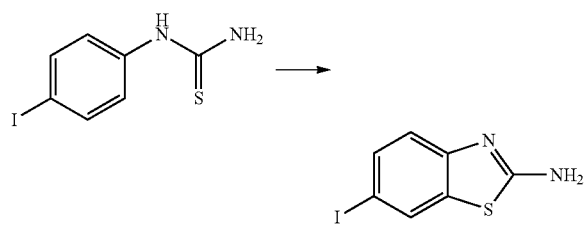

Bromine (328 ul, 6.40 mmol) was added to a suspension of 1-(4-iodopheyl)thiourea (889 mg, 3.19 mmol) in chloroform (7 ml) and heated to reflux for six hours. Once the reaction was completed, the solvent was evaporated off. After addition of dichloromethane, the reaction was washed with saturated aqueous sodium hydrogen carbonate and saturated aqueous sodium chloride, and dried over anhydrous sodium sulfate. The solvent was evaporated off under vacuum, and the residue was filtrated to obtain 650 mg 2-amino-6-iodobenzothiazole (yield: 73%).

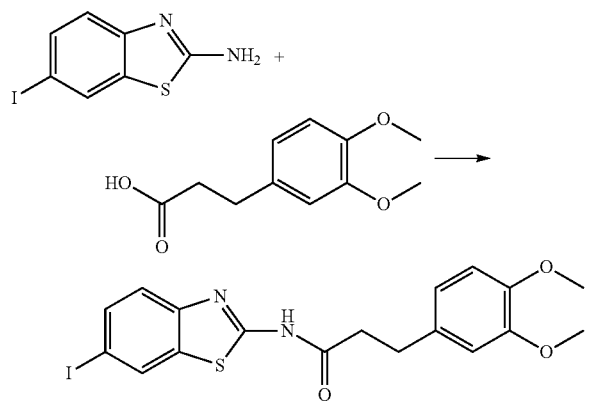

To a solution of 2-amino-6-iodobenzothiazole (100 mg, 0.362 mmol) and 3-(3,4-dimethoxyphenyl)propionic acid (94.1 mg, 0.435 mmol) in N,N-dimethylformamide (2 ml), N,N-diisopropylethylamine (69.4 ul, 0.398 mmol), O-(6-chlorobenzotriazol-1-yl)-N,N,N',N'-tetramethyluronium hexafluorophosphate (180 mg, 0.435 mmol) were added and stirred overnight at room temperature. Once the reaction was completed, the reaction mixture was diluted in ethyl acetate, washed with saturated aqueous sodium hydrogen carbonate and saturated aqueous sodium chloride, and dried over anhydrous sodium sulfate. Then, the solvent was evaporated off under vacuum. The residue was recrystallized from ethanol to give 83 mg 2-(3-(3,4-dimethoxyphenyl)propanamido)-6-iodobenzothiazole (yield: 48%).

$^1$H NMR (DMSO-d$_6$): δ 12.42 (s, 1H), 8.37 (s, 1H), 7.72-7.69 (m, 1H), 7.52 (d, J=8.4 Hz, 1H), 6.85-6.83 (m, 2H), 6.75-6.72 (m, 1H), 3.71 (s, 3H), 3.69 (s, 3H), 2.90-2.76 (m, 4H).

MS (ESI) Found; 469 [M+H]$^+$

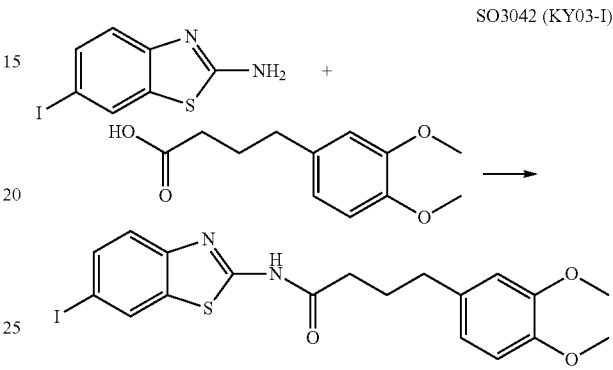

To a solution of 2-amino-6-iodobenzothiazole (250 mg, 0.905 mmol) and 4-(3,4-dimethoxyphenyl)butanoic acid (224 mg, 0.995 mmol) in N,N-dimethylformamide (3 ml), N,N-diisopropylethylamine (174 ul, 0.995 mmol), O-(6-chlorobenzotriazol-1-yl)-N,N,N',N'-tetramethyluronium hexafluorophosphate (450 mg, 1.09 mmol) were added and stirred overnight at room temperature. Once the reaction was completed, the reaction was diluted with ethyl acetate, washed with saturated aqueous sodium hydrogen carbonate and saturated aqueous sodium chloride, and dried over anhydrous sodium sulfate. Then, the solvent was evaporated off under vacuum. The residue was recrystallized from ethanol to give 131 mg 2-(4-(3,4-dimethoxyphenyl)propanamido)-6-iodobenzothiazole (yield: 30%).

$^1$H NMR (DMSO-d$_6$): δ 12.37 (s, 1H), 8.37 (s, 1H), 7.72-7.69 (m, 1H), 7.52 (d, J=8.4 Hz, 1H), 6.86-6.79 (m, 2H), 6.70 (d, J=8.0 Hz, 1H), 3.73 (s, 3H), 3.70 (s, 3H), 2.58-2.48 (m, 4H), 1.96-1.86 (m, 2H).

MS (ESI) Found; 483 [M+H]$^+$

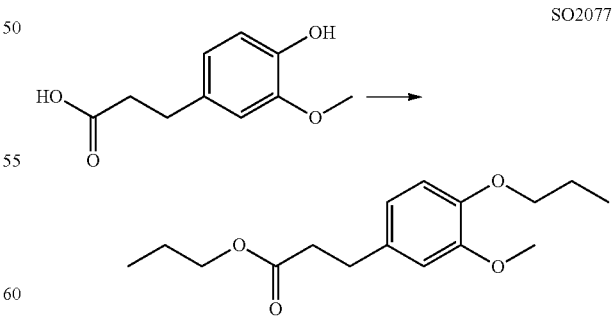

To a solution of 4-hydroxy-3-methoxyphenylpropionic acid (500 mg, 2.54 mmol) in N,N-dimethylformamide (5 ml), potassium carbonate (881 mg, 6.37 mmol) and 1-bromopropane 692 ul, 7.65 mmol) were added and stirred overnight at room temperature. Once the reaction was completed, the reaction was diluted with ethyl acetate, washed with water followed by saturated aqueous sodium chloride, and dried over anhydrous sodium sulfate. Then, the solvent was evaporated off under vacuum. The residue was subjected to the purification by chromatography in a silica gel column (4:1 n-hexane/ethyl acetate) to obtain 590 mg propyl 3-(3-methoxy-4-propoxyphenyl)propanoate (yield: 82%).

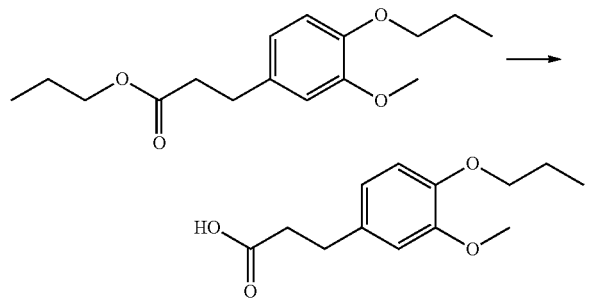

To a solution of 3-(3-methoxy-4-propoxyphenyl)propanoate (590 mg, 2.10 mmol) in 1,4-dioxane, an aqueous sodium hydroxide (5 mol/l, 1.68 ml) was added and stirred overnight at room temperature. Once the reaction was completed, the reaction was acidified with a 6 mol/l hydrochloride. Ethyl acetate was added for extraction, and the organic phase was washed with saturated aqueous sodium chloride and dried over anhydrous sodium sulfate. Then, the solvent was evaporated off under vacuum to give 438 mg 3-(3-methoxy-4-propoxyphenyl)propionic acid (yield: 87%).

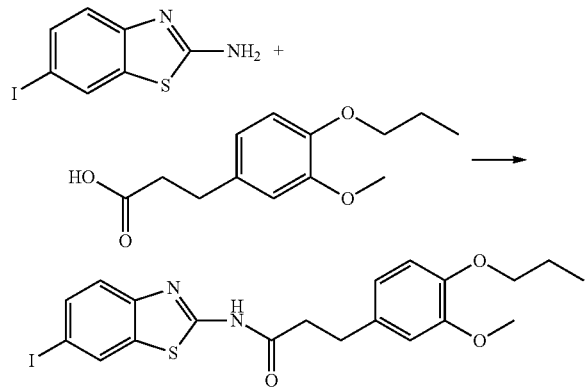

To a solution of 2-amino-6-iodobenzothiazole (200 mg, 0.723 mmol) and 3-(3-methoxy-4-propoxyphenyl)propionic acid (200 mg, 0.839 mmol) in N,N-dimethylformamide (3 ml), N,N-diisopropylethylamine (140 ul, 0.803 mmol), 0-(6-chlorobenzotriazol-1-yl)-N,N,N',N'-tetramethyluronium hexafluorophosphate (360 mg, 0.870 mmol) were added and stirred overnight at room temperature. Once the reaction was completed, the reaction was diluted with ethyl acetate, washed with saturated aqueous sodium hydrogen carbonate and saturated aqueous sodium chloride, and dried over anhydrous sodium sulfate. Then, the solvent was evaporated off under vacuum. The residue was recrystallized from ethanol to give 217 mg 2-(3-(3-methoxy-4-propoxyphenyl)propanamido)-6-iodobenzothiazole (yield: 60%).

$^1$H NMR (DMSO-d$_6$): δ 12.42 (s, 1H), 8.38-8.37 (m, 1H), 7.72-7.69 (m, 1H), 7.54-7.51 (m, 1H), 6.85-6.82 (m, 2H), 6.72 (d, J=8.0 Hz, 1H), 3.86-3.82 (m, 2H), 3.72 (s, 3H), 2.87-2.78 (m, 4H), 1.72-1.65 (m, 2H), 094 (t, J=7.3 Hz, 3H).

MS (ESI) Found; 497 [M+H]$^+$

SO3031 (KY01-I), SO2031 (KY02-I), SO3042 (KY03-I) and SO2077 were tested by a procedure as described in the Examples in WO 2012/026491 which is incorporated herein by reference, and found to have the effect of inducing cardiac differentiation.

The invention claimed is:

1. A method for inducing cardiac differentiation of a pluripotent stem cell, which comprises the steps of:
   (1) culturing a pluripotent stem cell in a medium containing a WNT signaling activator and a PKC activator and
   (2) culturing the cell after the step 91) in a medium containing a WNT signaling inhibitor, a Src inhibitor, and an EGFR inhibitor.

2. The method of claim 1, wherein the WNT signaling inhibitor is a compound of Formula (I):

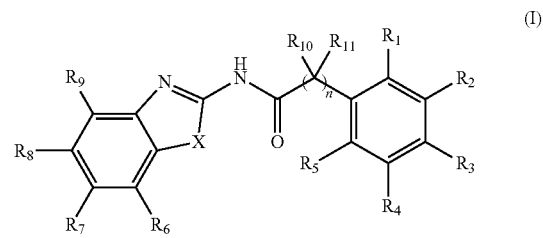

wherein
R$_1$ to R$_5$ are each independently a hydrogen atom; a halogen atom; a hydroxyl group; a linear or branched alkoxy group having 1 to 5 carbon atoms; a linear or branched alkyl group having 1 to 5 carbon atoms which is unsubstituted or substituted with a halogen atom; or a group —NR$_{12}$R$_{13}$, wherein R$_{12}$ and R$_{13}$ are each independently a hydrogen atom, an oxygen atom, or a linear or branched alkyl group having 1 to 5 carbon atoms which is unsubstituted or substituted with a halogen atom; wherein two adjacent groups among R$_1$ to R$_5$ may join together to form —O—CH$_2$—O— or —O—(CH$_2$)$_2$—O—;

R$_6$ to R$_9$ are each independently a hydrogen atom; a halogen atom; a hydroxyl group; a linear or branched alkoxy group having 1 to 5 carbon atoms; a linear or branched alkoxy group having 1 to 5 carbon atoms which is substituted with a group —C(O)A, wherein A is a saturated or unsaturated 5- or 6-membered ring which is unsubstituted or substituted with a linear or branched alkyl group having 1 to 5 carbon atoms and the ring may contain 1 or 2 atoms independently selected from a nitrogen atom, an oxygen atom and a sulfur atom; a linear or branched alkyl group having 1 to 5 carbon atoms which is unsubstituted or substituted with a halogen atom; or a group —NR$_{12}$R$_{13}$, wherein R$_{12}$ and R$_{13}$ are each independently a hydrogen atom, an oxygen atom, or a linear or branched alkyl group having 1 to 5 carbon atoms which is unsubstituted or substituted with a halogen atom; wherein two adjacent groups among R$_6$ to R$_9$ may join together to form —I—CH$_2$—O— or —O—(CH$_2$)$_2$—O—;

R$_{10}$ to R$_{11}$ are each independently a hydrogen atom; or a linear or branched alkyl group having 1 to 5 carbon atoms;

X is —$CR_{14}$, wherein $R_{14}$ is a hydrogen atom, a halogen atom, a hydroxyl group, a linear or branched alkoxy group having 1 to 5 carbon atoms, or a linear or branched alkyl group having 1 to 5 carbon atoms which is unsubstituted or substituted with a halogen atom; an oxygen atom; a sulfur atom; a selenium atom; or a group —$NR_{15}$, wherein $R_{15}$ is a hydrogen atom, a linear or branched alkyl group having 1 to 5 carbon atoms, or a linear or branched acyl group having 1 to 5 carbon atoms; and n is an integer of 0 to 6;

or a salt thereof.

3. The method of claim 2, wherein $R_1$, $R_4$, $R_5$, $R_6$, $R_7$, $R_8$, $R_9$, $R_{10}$, and $R_{11}$ are a hydrogen atom;

$R_2$ and $R_3$ are each independently a methoxy group, an ethoxy group or a propoxy group;

$R_7$ is a hydrogen atom; a halogen atom; a hydroxyl group, a linear or branched alkoxy group having 1 to 5 carbon atoms; a linear or branched alkoxy group having 1 to 5 carbon atoms which is substituted with a group —C(O)A, wherein A is a saturated or unsaturated 5- or 6-membered ring which is unsubstituted or substituted with a linear or branched alkyl group having 1 to 5 carbon atoms and the ring may contain 1 or 2 atoms independently selected from a nitrogen atom, an oxygen atom and a sulfur atom; a linear or branched alkyl group having 1 to 5 carbon atoms which is unsubstituted or substituted with a halogen atom; or a group —$NR_{12}R_{13}$, wherein $R_{12}$ and $R_{13}$ are each independently a hydrogen atom, an oxygen atom, or a linear or branched alkyl group having 1 to 5 carbon atoms which is unsubstituted or substituted with a halogen atom;

X is a sulfur atom, and n is an integer of 0 to 4.

4. The method of claim 3, wherein $R_7$ is a halogen atom.

5. The method of claim 1, wherein the WNT signaling inhibitor is a compound selected from the group consisting of:

KY02111

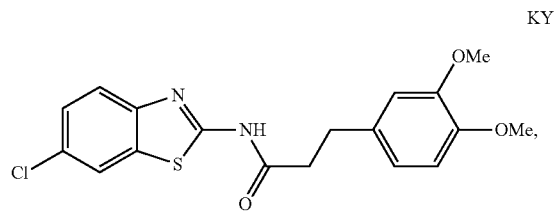

KY01041

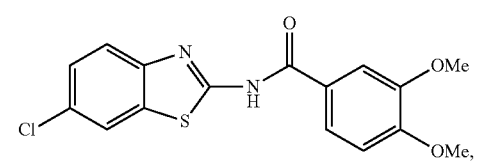

T61164

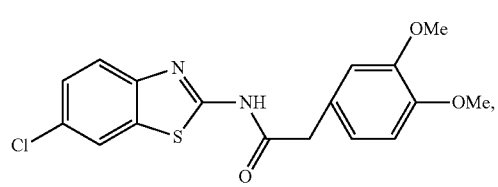

KY02114

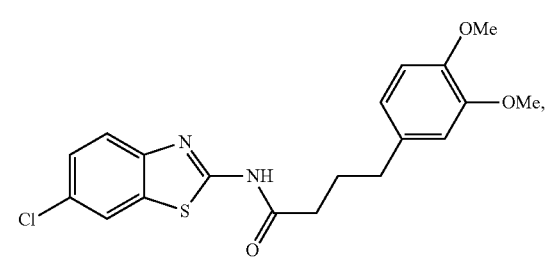

KY01045

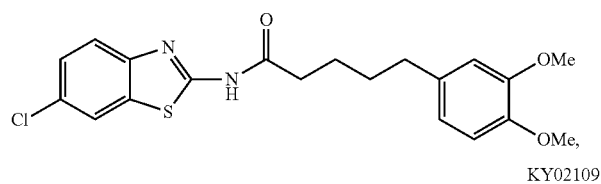

KY01040

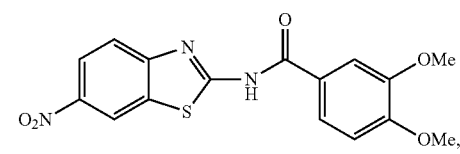

KY02109

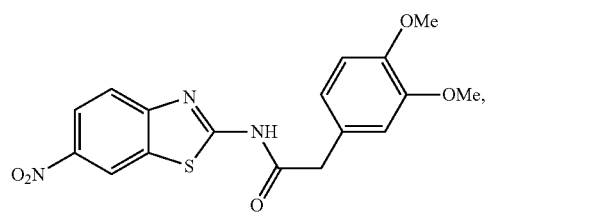

KY01042

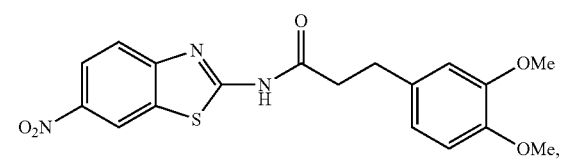

KY01043

KY01046

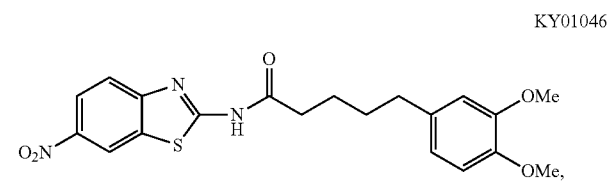

-continued

PB2852
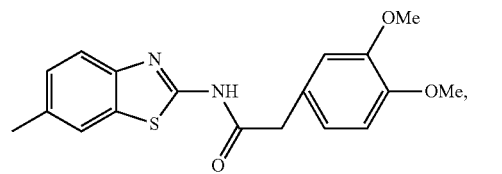

N11474
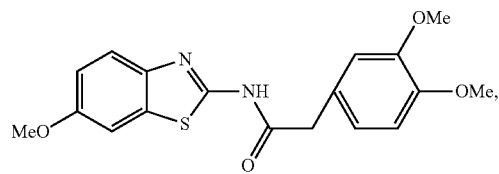

PB2572
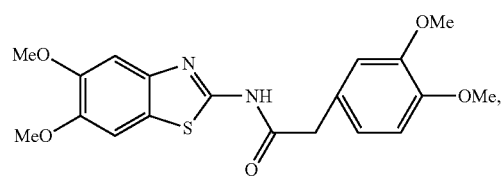

PB2570
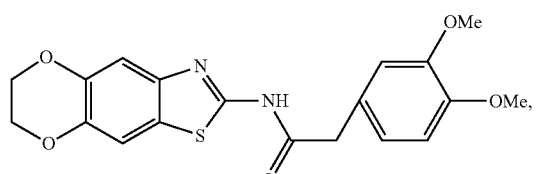

KY02104
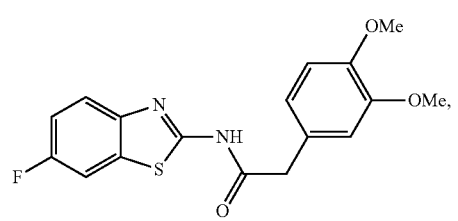

SO087
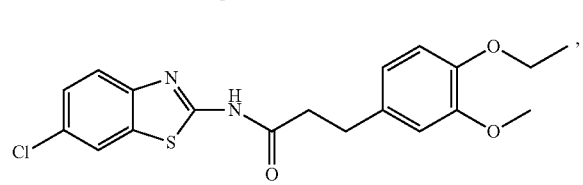

SO102
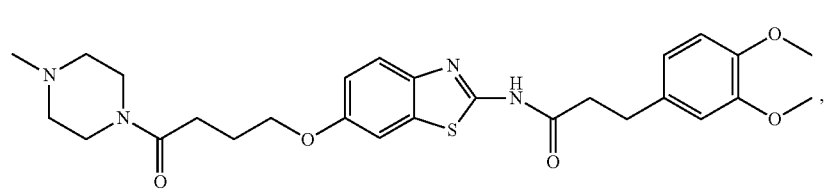

SO096
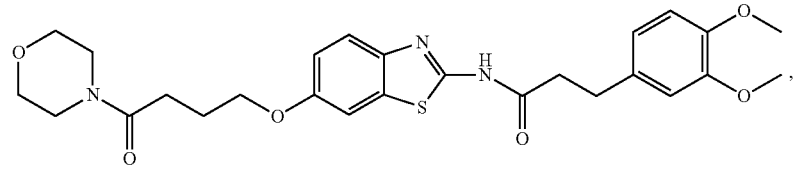

SOO094
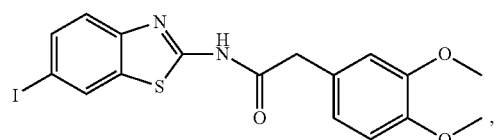

SO3031 (KY01-I)
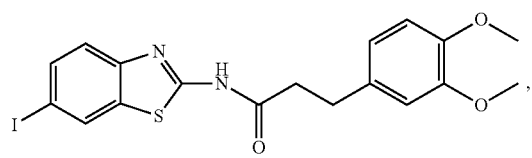

SO2031 (KY02-I)
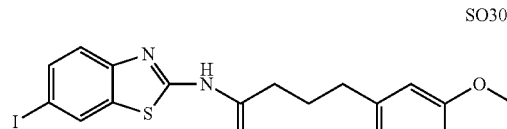

SO3042 (KY03-I)
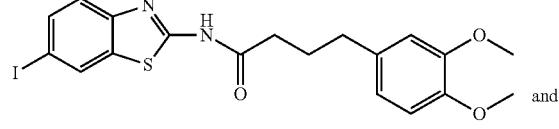 and

SO2077
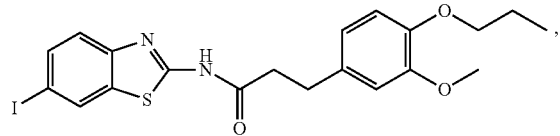

or a salt thereof.

6. The method of claim 5, wherein the WNT signaling inhibitor is KY02111, SO3031 (KY01-I), SO2031 (KY02-I) or SO3042 (KY03-I).

7. The method of claim 1, wherein the medium of step (2) comprises two or more WNT signaling inhibitors, and wherein one of the two or more WNT signaling inhibitors is the compound of Formula (I) or a salt thereof as recited in any one of claims 2, 3-4, and 5-6, and one or more of the two or more WNT signaling inhibitors are selected from the group consisting of IWP2, XAV939, and IWR1.

8. The method of claim 1, wherein the WNT signaling activator is BIO or CHIR99021.

9. The method of claim 1, wherein the PKC activator is PMA or prostratin.

10. The method of claim 1, wherein the Src inhibitor is A419259 or SU6656.

11. The method of claim 1, wherein the EGFR inhibitor is AG1478 or gefitinib.

12. The method of claim 1, wherein
the WNT signaling activator is CHIR99021,
the PKC activator is PMA,
the WNT signaling inhibitor comprises a compound selected from KY02111, SO3031 (KY01-I), SO2031 (KY02-I), and SO3042 (Ky03-I), and XAV939,
the Src inhibitor is A419259, and
the EGFR inhibitor is AG1478.

13. The method of claim 1, wherein the media of the steps (1) and (2) do not contain any protein or peptide component.

14. The method of claim 1, wherein the culturing of the steps (1) and (2) is in suspension culture.

15. The method of claim 1, wherein the culturing of the step (1) is for 1 to 3 days and the culturing of the step (2) is for 2 to 13 days.

16. The method of claim 1, wherein the pluripotent stem cell is a monkey or human pluripotent stem cell.

17. The method of claim 1, which is used to prepare a cardiomyocyte.

18. A kit for promoting cardiac differentiation comprising a WNT signaling activator, a PKC activator, a WNT signaling inhibitor, a Src inhibitor, and an EGFR inhibitor, wherein
the WNT signaling activator is CHIR99021,
the PKC activator is PMA,
the WNT signaling inhibitor comprises a compound selected from

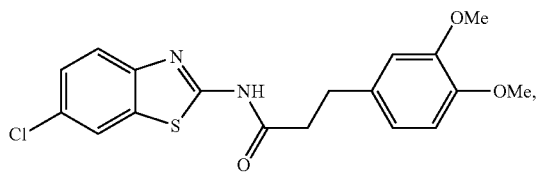
KY02111

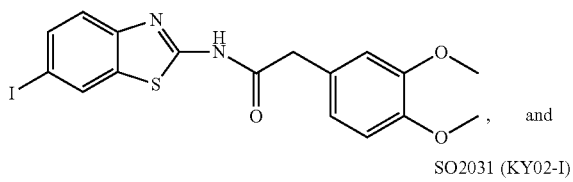
SO3031 (KY01-I)

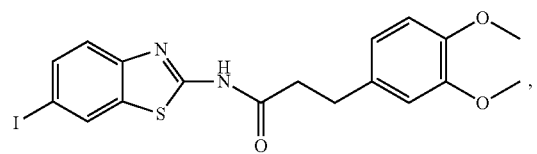
SO2031 (KY02-I), and

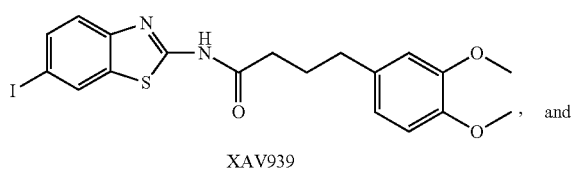
SO3042 (KY03-I)

XAV939, the Src inhibitor is A419259, and
the EGFR inhibitor is AG1478.

* * * * *